United States Patent [19]

Bacus

[11] 4,097,845

[45] Jun. 27, 1978

[54] METHOD OF AND AN APPARATUS FOR AUTOMATIC CLASSIFICATION OF RED BLOOD CELLS

[75] Inventor: James W. Bacus, Hinsdale, Ill.

[73] Assignee: Rush-Presbyterian-St. Luke's Medical Center, Chicago, Ill.

[21] Appl. No.: 825,673

[22] Filed: Aug. 18, 1977

Related U.S. Application Data

[63] Continuation-in-part of Ser. No. 737,531, Nov. 1, 1976, abandoned.

[51] Int. Cl.$^2$ .............................................. G06K 9/00
[52] U.S. Cl. ......................... 340/146.3 CA; 128/2 G; 235/92 PC; 356/39; 364/416; 364/515
[58] Field of Search .......... 340/146.3 AC, 146.3 CA; 235/92 PC, 151.3; 250/201, 202, 204, 222 PC; 356/39, 102, 125, 244; 350/92; 23/230 B, 258.5; 128/2 A, 2 G; 324/71 CP

[56] References Cited

U.S. PATENT DOCUMENTS

| | | | |
|---|---|---|---|
| 3,315,229 | 4/1967 | Smithline | 235/92 PC |
| 3,733,136 | 5/1973 | Porath-Furedi | 356/39 |
| 3,832,687 | 8/1974 | Miller et al. | 340/146.3 AC |
| 3,851,156 | 11/1974 | Green | 356/39 |
| 3,851,972 | 12/1974 | Smith et al. | 356/39 |
| 3,873,974 | 3/1975 | Bouton et al. | 340/146.3 AC |
| 3,883,852 | 5/1975 | Cotter | 364/900 |
| 3,893,767 | 7/1975 | Fulwyler et al. | 356/39 |
| 3,916,205 | 10/1975 | Kleinerman | 356/39 |
| 3,919,530 | 11/1975 | Cheng | 128/2 G |
| 4,000,417 | 12/1976 | Adkisson et al. | 250/201 |

OTHER PUBLICATIONS

Ward et al., "Coherent Optical Rec. & Counting of Reticulated Red Blood Cells," IEEE Trans. on Biomedical Eng., vol. BME-21, No. 1, Jan. 1974, pp. 12-20.

Primary Examiner—Leo H. Boudreau
Attorney, Agent, or Firm—Fitch, Even, Tabin & Luedeka

[57] ABSTRACT

A method and apparatus for automatically classifying abnormal and normal red blood cells is disclosed. The abnormal cells may be differentiated into mutually exclusive subpopulations. The individual hemoglobin characteristic for each red blood cell is measured and a hemoglobin parameter may be reported for each subpopulation of cells. Additionally, cell sizes are measured and the mean cell size and Wintrobe indices may be reported. The interior cell structures for red blood cells are analyzed and the cells are classified based on the presence or lack of a central pallor, their shape, size, and hemoglobin content.

18 Claims, 15 Drawing Figures

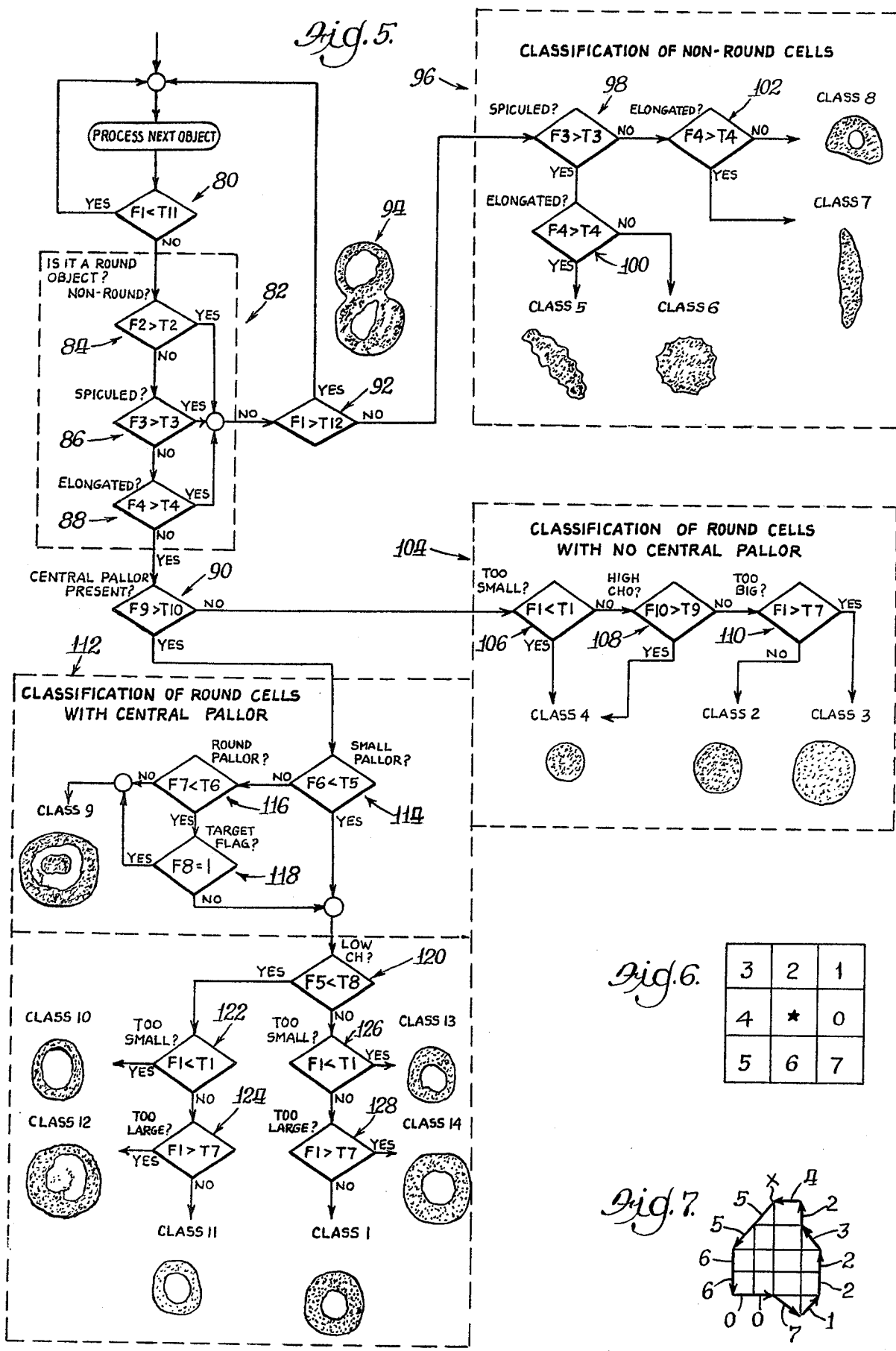

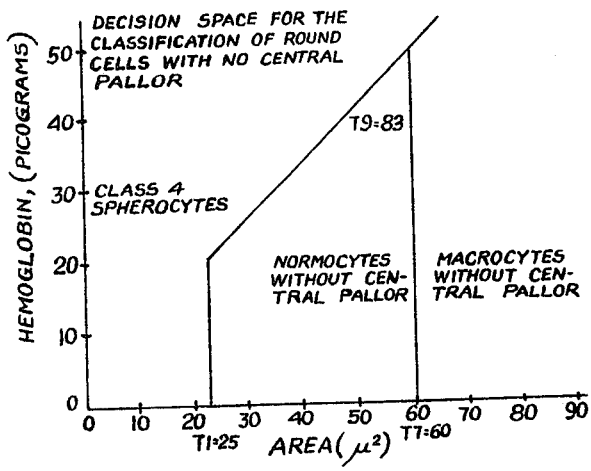
Fig. 11.
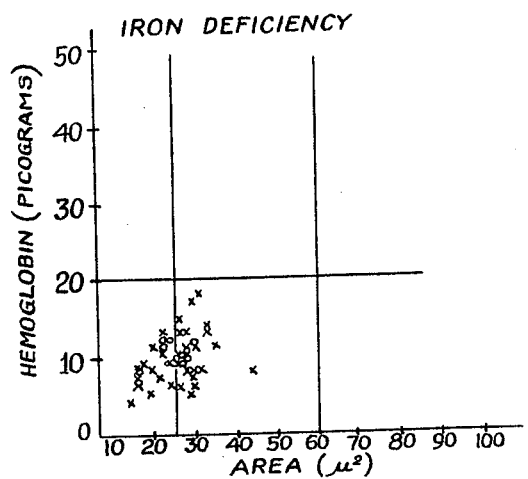
Fig. 12.
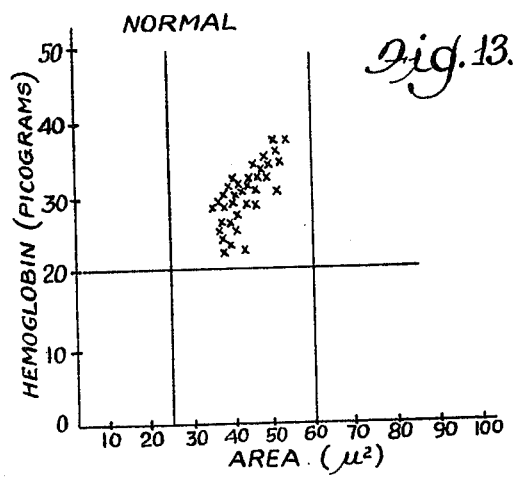
Fig. 13.
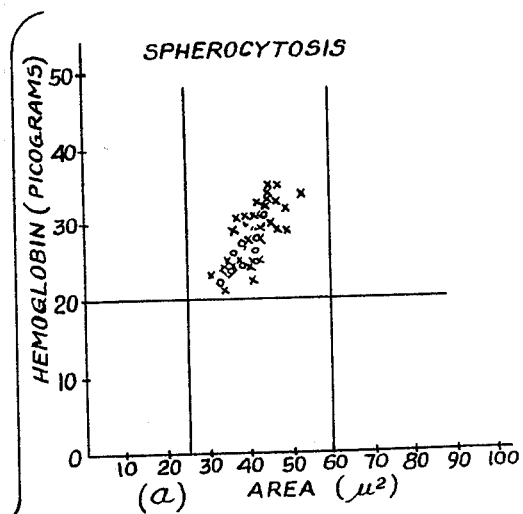
(a)
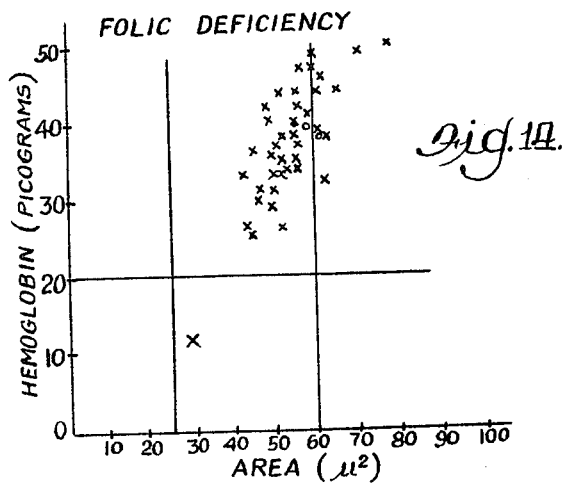
Fig. 14.
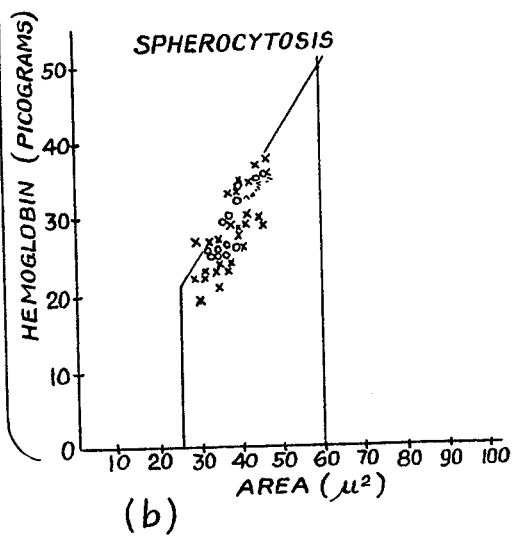
(b)
Fig. 15.

METHOD OF AND AN APPARATUS FOR AUTOMATIC CLASSIFICATION OF RED BLOOD CELLS

The invention described herein was made in the course of work under a grant or award from the Department of Health, Education and Welfare.

This is a continuation-in-part of my patent application, Ser. No. 737,531, filed Nov. 1, 1976, now abandoned.

This invention relates to a method of and an apparatus for automatically classifying red blood cells.

The diagnosis of a particular one of more than a dozen major types of anemia often uses information derived from subjective visual evaluation of a stained red blood cell specimen to determine the kinds of abnormal red blood cells present in the specimen. Typically, if it is desired to further quantitate the abnormal red blood cells and to provide a size parameter therefor, there is involved an expenditure of several hours by a highly skilled technician. Even then, the reliability of the red blood cell quantification is suspect for the reasons that the technician may be making subjective evaluations and judgements when classifying the abnormal cells. Further, error may be introduced into this manual system by slide preparation which currently involves a staining of the cells on the slide, the staining character varying with temperature, humidity and time. For these reasons, there presently is a lack of standard parameters for the diagnosis of certain kinds of anemia based on a morphological quantification of abnormal red blood cells and their individual hemoglobin content. In addition, it has not been heretofore possible to obtain a hemoglobin analysis of a particular class (i.e., subpopulation) of abnormal red blood cells in a blood specimen.

The present invention is directed to solving the problem of automatically classifying the normal and abnormal red blood cells into cell subpopulations and providing meaningful red blood cell parameters for these separate subpopulations of normal or abnormal cells. One difficulty encountered in separating the abnormal cells into meaningful and widely recognized subpopulations on an automated basis is that of accurately segregating the cells by their morphology and color, particularly where their respective areas or sizes and shapes overlap and their respective principal distinguishing feature is the configuration of their respective central pallors (or a lack of central pallor). Central pallor is the thin, disc-shaped central area of red blood cells which may be circular and particularly pronounced for some cells. For instance, target cells and normocytes may have substantially the same size area and shape, but differ in the central pallor configurations. Thus, to distinguish between these cells, the automated analysis should be able to examine and classify cells on the basis of their interior configurations, as well as their exterior configurations.

Other cells, such as spiculed red blood cells, may have the same general size, area and interior configurations of normocytes or the like and are distinguished principally by their indented spiculed perimeters. Likewise, adding to the difficulty of classifying abnormal cells such as sickle cells from other elongated cells is that they may have similar peripheral measurements, sizes and areas and differ principally from one another in the presence of pointed projections, as spicules. Still other abnormal cells may be separately categorized from other morphologically similar cells only by their hemoglobin content, measured in terms of color or density. Therefore, it is desirable to distinguish the hypochromic cells from those that are normochromic.

In addition to the technical difficulties of automatically classifying morphologically similar cells into different subpopulations, the method and process, to be commercially successful, cannot be so elaborate, expensive and slow as to be economically unfeasible. Thus, there is a need to develop a more discerning method and apparatus to provide an accurate quantitative classification of red blood cells into widely and commonly, hematologically recognized subpopulations which aids in the diagnosis or the pathology of anemia and to measure and report parameters such as the quantification of the cells in each subpopulation, and the widely recognized Wintrobe Indices of mean cell size, mean cell hemoglobin and mean cell hemoglobin concentration, for each subpopulation.

As will be explained in greater detail hereinafter, the present invention is described in connection with a microscopic slide, digital image and pattern recognition system, but the invention is not to be construed as limited to such a system, as the feature analysis of the sample to classify the red blood cells into mutually exclusive subpopulations and to report red blood cell parameters for at least one subpopulation may be performed using other techniques, such as a coherent optical analysis technique disclosed in U.S. Pat. No. 3,947,123, or a liquid flow process technique such as disclosed in U.S. Pat. Nos. 3,819,270 and 3,822,095. To be commercially feasible, the digital image and pattern recognition process for red blood cells should operate on a real time basis and with sufficient speed and accuracy that it will perform as well as the now commercially accepted leukocyte differential counting systems, such as, for example, the LARC manufactured by Corning Glass Works of Corning, New York, and generally disclosed in U.S. Pat. No. 3,883,852.

The Coulter Counter, manufactured by Coulter Electronics, Hialiah, Florida, provides results which are helpful in diagnosing anemia in that it provides a red blood cell count and mean red blood cell parameters characterizing the entire population of cells. More specifically, the Wintrobe Indices of mean cell volume, mean cell hemoglobin and mean cell hemoglobin concentration along with the number of red cells per cubic millimeter are currently obtained with the Coulter Counter, which is a liquid flow system. No differentiation between abnormal or normal red blood cells is achieved with the Coulter Counter.

Heretofore, some off-line experimental work has been performed on image processing of erythrocytes. One of these works, "Bentley, S. A. and S. M. Lewis, 'The Use of an Image Analyzing Computer for the Quantification of Red Cell Morphological Characteristics', Brit. J. Haemat. 29:81, 1975", describes an off-line analysis of dried and stained red blood cells of a total cell population measuring three red blood cell parameters by an image analysis technique. This analysis is similar to the Coulter Counter analysis in that the parameters measured were from the total population of cells being analyzed, and were analogous to the Wintrobe Indices. The drying of the red cells introduced artifacts, and there was a lack of central pallor, or internal red cell analysis to provide a highly refined classification. Moreover, there was not disclosed the capability for differentiating between and classifying normal red blood cells from abnormal red blood cells.

Measurements of normal erythrocytes without differentiation of any abnormal erythrocytes by image processing was disclosed by J. E. Green and reported in a paper entitled "Green, J. E., 'Computer Methods for Erythrocyte Analysis', Proceedings of Symposium of Feature Extraction and Selection in Pattern Recognition, IEEE Catalog No. 70CSIC pp. 100, Argonne, Illinois, 1970". A similar type of paper for reporting measurements of normal red cells and how to measure their features without any classification thereof was disclosed in a paper entitled "Eden, M., 'Image Processing Techniques in Relation to Studies of Red Cell Shape' in Red Cell Shape, edited by M. Bessis, R. I. Weed and P. F. Leblond, Springer-Verlag, New York, pp. 141, 1973".

In short, none of the aforementioned systems has the ability to analyze cells by their features, particularly their inner features of cell pallor and to quickly classify the same into previously recognized categories for a particular type of abnormal red blood cell. Not only should the scheme differentiate between normal and other red blood cells, but it also should be relativly foolproof in its analysis and be done in a commercially acceptable real time span, so that the results may be provided to the diagnostician for timely analysis. Although some clinicians may not, at this time, appreciate the value of having a quantification of red blood cells in recognized subpopulations and the Wintrobe Indices for each subpopulation, it is anticipated that the data will result in the development of new standards in the diagnosis of anemia.

The staining of the red blood cells prior to being analyzed by a microscopic image processing technique has been found to be a time-consuming process, as well as undesirable in that the staining may introduce a number of stained artifacts which detract from the accuracy of the analysis. Furthermore, many of the stains are not stoichiometric in the representation of hemoglobin concentration according to density, thus distorting the quantization of the hemoglobin content of the cells on a-per-cell basis. A particular manner of fixing cells before they dry without staining thereof to prevent the formation of artifacts by distortion of the central pallor or by the stain is disclosed in co-pending application of James W. Bacus entitled "Method and Apparatus for the Preparation of Blood Samples for Automated Analysis", filed of even date, and hereby incorporated by reference as if fully reproduced herein. As explained in the aforementioned application, the preparation of the erythrocyte slides by known spin techniques may be made by known apparatus of the type shown in U.S. Pat. No. 3,906,890, or by a viscosity dilution technique where it is possible to use a constant spin time and a constant speed of spinning, the latter system being reported by James W. Bacus in a paper entitled "Erythrocyte Morphology and Centrifugal 'Spinner' Blood Film Preparations", *The Journal of Histochemistry and Cytochemistry*, Vol. 22, No. 77, pp. 506–516, 1974.

A general object of the invention is to differentiate with an automated apparatus between normal and abnormal red blood cells.

Another object of the invention is to provide a method and apparatus for automatically classifying red blood cells by their respective features into mutually exclusive cell subpopulations.

A more specific object of the invention is to provide a red blood cell analysis system which measures and records hemoglobin and other parameters for at least one of these respective subpopulations.

A further object of the invention is to provide a red blood cell analysis system which classifies red blood cells by features of size, spicularity, roundness, elongation, central pallor and hemoglobin content.

A further object of the invention is to provide an image analysis system which fixes the internal morphology, i.e., the central pallor of the red blood cells prior to analysis and uses light wavelengths which render artifacts substantially invisible to analysis.

A still further object of the invention is to provide a new and improved technique for classifying red blood cells by linguistically descriptive features.

These and other objects of the invention will become apparent from the following detailed description and accompanying drawings in which:

FIG. 5 is a flow chart of the preferred classification technique to classify red blood cells into mutually exclusive categories;

FIG. 6 is a diagram of the directions for a chain code analysis;

FIG. 7 illustrates a chain code description of the cell of FIG. 8;

FIGS. 10a, 10b, and 10c are graphs illustrating the central pallor definition and measurement for three different, typically occurring cell types, i.e., FIG. 10a illustrating a typical red cell with a well developed central pallor; FIG. 10b illustrating an intermediate central pallor development with a difference greater than the threshold definition and FIG. 10c illustrating a "flat" cell having no central pallor development;

FIG. 11 is a graph illustrating the decision space for the classification of round cells with no central pallor using the decision logic of FIG. 5;

FIG. 12 is a graph of area vs. hemoglobin and illustrating the decision space for the classification of round cells with central pallor and including measurements on approximately 70 cells on a blood specimen from a patient with iron deficiency anemia, using data from classes 1, and 10 through 14 and the decision logic of FIG. 5;

FIG. 13 is a graph of area vs. hemoglobin and illustrating the decision space for the classification of round cells with central pallor, together with approximately 70 measurements from a normal specimen using data from classes 1, and 10 through 14 using the decision logic of FIG. 5;

FIG. 14 is a graph of area vs. hemoglobin and illustrating the decision space for the classification of round cells with central pallor and including approximately 70 measurements from a patient with megaloblastic anemia using data from classes 1, and 10 through 14 using the decision logic of FIG. 5; and, FIGS. 15a and 15b are graphs of area vs. hemoglobin illustrating the decision space for the classification of round cells with and without central pallor, respectively, including approximately 200 measurements from a patient with hereditary spherocytosis, using the decision logic of FIG. 5 and data from classes 1, and 10 though 14 in FIG. 15a and classes 2, 3 and 4 in FIG. 15b.

Figure 1:
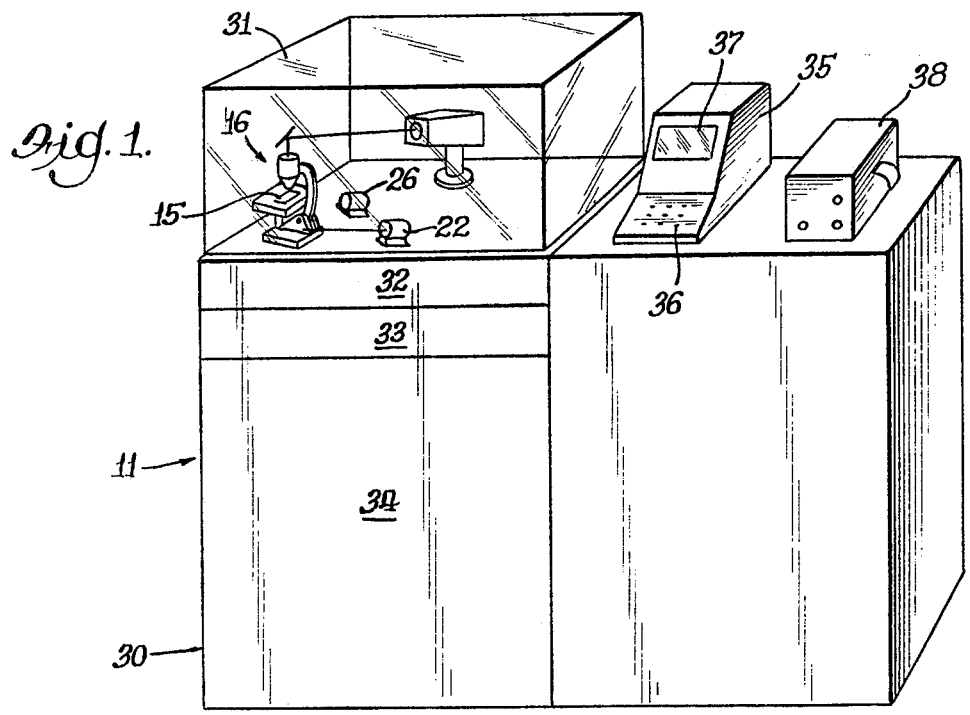
FIG. 1 is a perspective view of an apparatus for practicing the method of red blood cell analysis and embodying the novel features of the invention.
Figure 2:
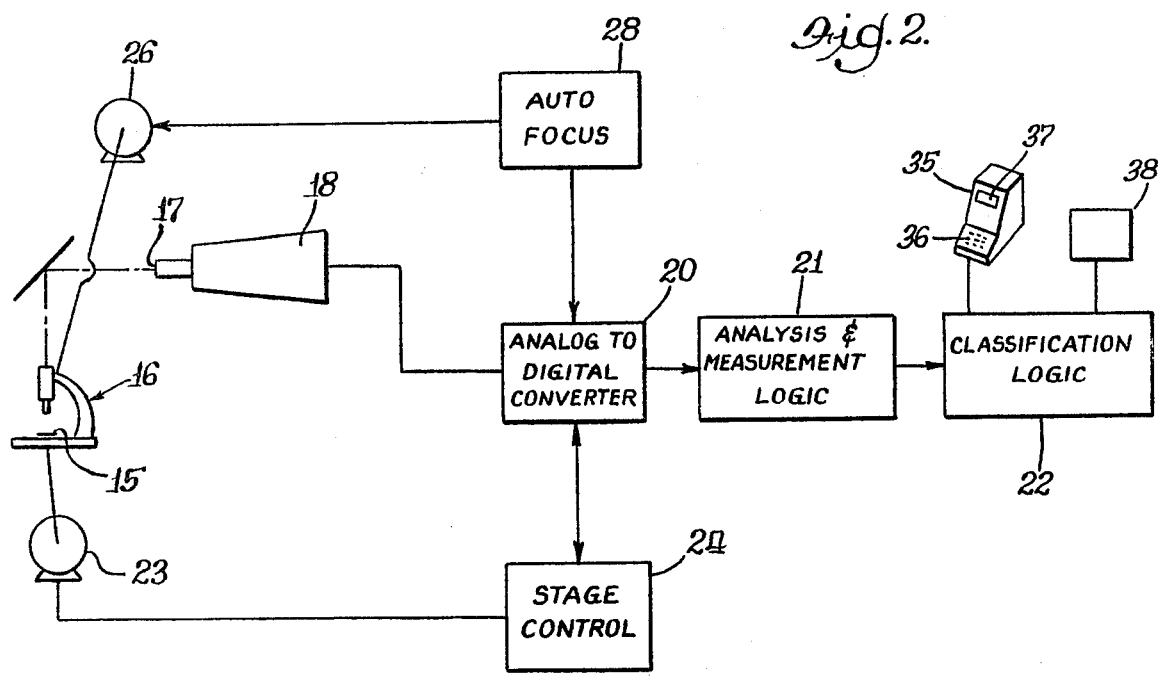
FIG. 2 is a block diagram showing the operation of the apparatus illustrated in FIG. 1.

As shown in FIGS. 1 and 2 of the drawings, for purposes of illustration the invention is embodied in an apparatus 11, a microscopic digital image processing and pattern recognition system which analyzes a monolayer of red blood cells on a microscope slide 15 with the cells being spaced from each other to ease the automated classification thereof. Suitable high resolution microscope optics 16 form an optical image for each red blood cell on a vidicon television camera tube or other detector 18 which coverts the optical images point by point into a scanned electronic charge distribution representing the optical transmission of the points in each image. The output of the vidicon camera is applied to an analog to digital converter 20 which is connected to analysis and measurement logic 21 which receives and stores the digitized cell images. The analysis and measurement logic operates on the digitized cell images in a manner that will be hereinafter described and the information is applied to classification logic 22 which classifies the cells using techniques that will also be described herein. A suitable stage motor means 23 is provided and controlled by a stage control logic circuit means 24 to shift the slide to iteratively process different image areas of the blood specimen on the slide. To control the focus of the microscope, a focus control motor means 26 is connected to the microscope and is operated by an automatic focus logic circuit means 28. Focus control of slides for image analysis is well known in the art, e.g., U.S. Pat. No. 3,967,110.

The apparatus 11 shown in FIG. 1 includes a housing 30 having a cover 31 enclosing the microscope optics 16 and the television vidicon 18, all of the light source not being shown. An upper section 32 of the housing 30 houses the analog to digital logic circuit means 20 and the next lower section 33 houses the focus control logic circuit means 28 with the final, lower portion 34 of the housing containing the analysis and measurement logic 21 and the classification logic 22. A terminal 35 is connected to the classification logic 22 and has a keyboard 36 for input of identifying information about the specimen or for other instructions. A monitoring screen 37 provides a visual display of the final report, and preferably a written printout is also made by a printer means 38 to afford a permanent record. The results of the red blood cell analysis may also be transmitted for storage in a medical computer data bank. A general layout of equipment of this type for leukocyte analysis and for reporting leukocyte results is known in the art and is of the general type disclosed in U.S. Pat. Nos. 3,883,852 and 3,824,393.

The presently practiced red blood cell analysis techniques are highly subjective with the viewer of cells rendering broad generalizations about the cells in his immediate view in such inconclusive terms as anisocytosis, poikilocytosis, polychromic or normocytic. The viewer does not make a specific count of the various abnormal cell types being seen, as such a manual count thereof to provide a ratio of each cell type to the total cell population is too laborious, and in the absence of a standard based on similar counts may not be informative to the clinician. The generalization of poikilocytosis is also not definitive. For instance, although the viewer may indicate the more prevalent abnormal cells in his view, he may miss or dismiss those abnormal cells which are present only in minor quantities, but the presence of which may be clinically important to diagnosis, particularly of anemias in their incipiencies. While it is possible for a viewer to measure cell sizes when anisocytosis is found, the measure of cells manually is not usually done for the reason that it is too time consuming and reliance is made on the mean cell size of the total population from a Coulter Counter or the like. Judgment of color is most subjective, given the variance in human eyesight and color perceptions. Moreover, to single out a single subpopulation of abnormal red cells and to try to provide a mean color analysis thereof is simply not done and would probably not be of sufficient accuracy and reliability to warrant doing manually. Thus, it will be seen that the present information about given subpopulations of red blood cells is highly subjective and general in nature.

In accordance with the present invention, red blood cells may be examined such that normal cells are distinguished from abnormal cells and classified by the apparatus 11 into subpopulations automatically in a detailed fashion heretofore not possible by a manual/visual examination of the cells. Also, each of the red blood cells being examined may be classified into mutually exclusive subpopulations and reported out so that the presence of a minor number of abnormal cells is not overlooked or forgotten and so that accurate parameters about a given subpopulation may also be provided. For the first time, the individual red blood cells may be examined individually for their hemoglobin contents. Thus, a report may be made not only of the kinds of cells found in a subpopulation but also of their number and their hemoglobin characteristics. Advantageously, the individual red blood cells may be analyzed and classified with less subjectivity into a large number of mutually exclusive subpopulations (Table I) such as normocytes, macrocytes, spherocytes, etc., which are widely known and readily recognized cell classifications accepted by hematologists. Moreover, it is further possible, and thought preferable, to further classify the recognized cell classification, e.g., macrocytes, by additional modifiers reflective of their color or internal shapes. For instance, macrocytic cells may be further divided into subpopulations of macrocytes without central pallor, hypochromic macrocytes with central pallor, and normochromic macrocytes with central pallor. Similarly descriptive subclassifications also may be made for normocytes or microcytes.

The preferred hemoglobin characteristics gathered from the analysis of the hemoglobin contents of the individual cells within a given subpopulation and reported out are the mean cell hemoglobin and the mean cell hemoglobin density for a given subpopulation of cells, such as shown in Table I. In addition to the hemoglobin parameters, the individual cells are counted for each subpopulation to provide their respective percentages of total population; and likewise a mean cell size for each subpopulation may also be reported. This data has been unavailable prior to this invention from any commercial instrument, or in any other fashion, such as from special research instrumentation. The closest analogous instrument is the Coulter Counter (Coulter Co., Hialeah, Fla.) which is unable to classify red blood cells into these types of subpopulations and which can report only mean cell size and mean cell hemoglobin parameters for the entire population of red blood cells.

Herein, the invention will be described as having the ability to classify red blood cells into the several mutually exclusive subpopulations set forth in Table I. The classes are numbered in order to facilitate an understanding of the classification system illustrated in FIG. 5, but only a few of the classes are usually reported for a given blood sample. The cell means size is reported in ($\mu$) microns$^2$. The mean cell hemoglobin (MCH) is reported in picograms (pg) and the means cell hemoglobin density (MCHD) is reported in picograms/micron$^2$ (pg/$\mu^2$).

The several subpopulations described hereinafter are:

TABLE I

| Class | % | Description | Size ($\mu^2$) | MCH (pg) | MCHD (pg/$\mu^2$) |
|---|---|---|---|---|---|
| 1 | 12 | NORMOCYTES WITH CENTRAL PALLOR | 43 | 31 | 72 |
| 2 | 1 | NORMOCYTES WITHOUT CENTRAL PALLOR | 41 | 32 | 78 |
| 3 | 5 | MACROCYTES WITHOUT CENTRAL PALLOR | 62 | 50 | 81 |
| 4 | 9 | SPHEROCYTES | 26 | 24 | 92 |
| 5 | 7 | ELONGATED, SPICULED CELLS | 33 | 13 | 39 |
| 6 | 23 | SPICULED, IRREGULAR SHAPED CELLS | 34 | 18 | 53 |
| 7 | 16 | ELONGATED CELLS | 35 | 20 | 57 |
| 8 | 9 | IRREGULAR SHAPED CELLS | 33 | 16 | 48 |
| 9 | 3 | TARGET CELLS | 43 | 14 | 33 |
| 10 | 1 | HYPOCHROMIC MICROCYTES WITH CENTRAL PALLOR | 33 | 17 | 52 |
| 11 | 2 | HYPOCHROMIC NORMOCYTES WITH CENTRAL PALLOR | 42 | 15 | 36 |
| 12 | 1 | HYPOCHROMIC MACROCYTES WITH CENTRAL PALLOR | 65 | 19 | 29 |
| 13 | 7 | NORMOCHROMIC MICROCYTES WITH CENTRAL PALLOR | 30 | 17 | 57 |
| 14 | 2 | NORMOCHROMIC MACROCYTES WITH CENTRAL PALLOR | 62 | 43 | 69 |

To achieve a classification of individual cells into hematologically recognized subpopulations, such as those shown in Table I, has required the examination of the cells by several features; not only as to their size, area and shapes, but also as to their internal configurations to distinguish red blood cells having central pallors (such as a cell 49A shown in FIG. 3) from a similar size and shaped cell 49D (FIG. 3) lacking a central pallor. It has been found that the identification of the cells, such as target cells, is enhanced by not only establishing the existence of a central pallor but also further examination of the size, shape and location of the central pallor to provide a distinguishing feature for each cell. Because of the ability of the present invention to provide analysis of the hemoglobin content of the cell, it is possible to describe and classify cells not only by their usual size classification but also by further descriptions of colors, such as hypochromic, hyperchromic or normochromic, and such as with or without a central pallor. Color or density also assists in differentiating between spherocytes and normocytes.

The present invention is directed to the optimization in the time of analysis as well as the number of features used in the classification logic so that the amount of storage and classifying techniques may be reduced substantially along with euipment requirements therefor. With an optimization of analysis time for classification, there is a danger that the reliability and accuracy of the classification are compromised. Despite this, a relatively foolproof feature set and classification logic has been invented for a large number of subpopulations such as those shown in Table 1. The preferred classification features are size, spicularity, roundness, elongation, central pallor and hemoglobin content. By suitable combinations and analyses of such features, it is possible to differentiate from normal cells and to identify spherocytes, target cells, spiculed cells, irrregular shaped cells, elongated cells, as well as to differentiate among the respective colors or densities thereof such as hyperchromic or hyprochromic, from normochromic.

In the preferred method and apparatus, the cell classifications are achieved by an image processing and pattern recognition with great accuracy and reliability by rendering white blood cells and other artifacts substantially invisible to the optics 17 by using a light having an optical wavelength of about 417 Nanometers. At this optical wavelength, the red blood cells are relatively contrast enhanced to the ultraviolet sensitive Vidicon camera without staining, while the white blood cells and other formed elements are substantially invisible. Thus, by rapidly preparing the specimens in a monolayer and fixing with a formaldehyde vapor prior to the drying of red blood cells, as disclosed in the aforementioned co-pending patent application, and by not employing a time consuming staining to contrast enhance the cells, as in white blood cell analysis, these specimens may be quickly prepared and analyzed acurately.

The location of the cell image and the identification and feature extraction has been greatly simplified by using a novel scene segmentation technique to locate and define the cells and extract the summed density or hemoglobin feature, followed by a boundary procedure which defines the cell in the form of an octal chain code. The use of octal chain codes as an image processing technique is described in a paper by Freeman H., Computer Processing of line-drawing images, ACM Computing Surveys 6:57, 1974. As will be explained in greater detail, the octal chain code allows feature extraction as to: (1) cell size, (2) perimeter length and roundness shape measure, (3) irregular shape measure and (4) elongation shape measure.

As will be explained in greater detail, the preferred method of locating and defining the central pallor is to search inwardly of the digitized cell image from an original raster scanning threshold point looking for another threshold condition indicative of a central pallor. If a central pallor is located, then its boundary is analyzed and labeled and an octal chain is produced for the central pallor, as above described. Suitable features of size and shape are also measured from this chain code and added to the outer boundary and hemoglobin feature.

After having extracted these identifying features, the cells are then categorized by a classification means. The preferred classification means (FIG. 5) may comprise either a digital logic system of electrical devices or a programmed microprocessor which uses Boolean logic to classify the red blood cells. This is in contrast to a standard multivariate Gaussian classification system or as compared to an eigenvector transformation of vectors to provide meaningful modes or clusters of data. These latter systems require training sets, re-evaluaitons and requre a longer and more complex mathematical analysis, see U.S. Pat. No. 3,824,393.

Referring now in greater detail to the specific features of the illustrated embodiment of the invention, the sample preparations were made by taking a sample of whole blood and diluting the same with a serum-albumin solution of 1.3 relative viscosity to adjust the hematocrit of each sample. The viscosity was relative to $H_2O$ as 1.0 and a typical range of relative viscosities for blood plasma is 1.2–1.8. Alternatively, a standard isotonic saline solution in a covenient ratio, e.g., 1:1, may be used as a diluent for most bloods. This procedure enables the spinning time for all bood specimens to be constant. As is recognized in the art, for specimens where the viscosity has not been adjusted, if the spinning period is too short, the cells are clustered together and thus impossible to isolate and classify individually. If the spinning period is too long, there is an undue distortion of the cell shapes. Rather than adjusting the plasma viscosity and using a constant spin time, as preferred, spin apparatus may be used which controls the spinning period, as disclosed in U.S. Pat. Nos. 3,827,805 and 3,906,890.

Herein, the monolayer of red blood cells on the slide is preferably fixed with a formaldehyde vapor for a period of a few minutes immediately after formation of the monolayer to preserve the morphologies of the red blood cells and particularly the configurations of their central pallors for later analysis. After fixing the cells, they are allowed to air dry. Sample preparation is disclosed more fully in the aforementioned co-pending patent application and in an article by James W. Bacus, "Erythrocyte Morphology and Centrifugal 'Spinner' Blood Film Preparations", *The Journal of Histochemistry and Cytochemistry*, 22:7:506–516, 1974. As explained therein, the red blood cells are separated from each other by these preparation techniques and are in a monolayer ready for image analysis.

The fixing of the red blood cells in a monolayer without staining and analyzing at light wavelenths of about 417 Nanometers is preferred to present staining techniques, as it is faster than a staining technique, such as the Wright's stain used for the leukocyte analysis and provides greater accuracy and reliability of results. That is, distortions in the red blood cell images may occur because typical stains, such as the Wright's stain, are not stoichiometrically related to red cell hemoglobin content and vary in resulting color or density with certain changes in conditions of temperature, humidity, and time.

The preferred light used to form the red blood cell images is selected at a wavelength, which has been found to be particularly useful in providing contrast enhancement of the red blood cells relative to the other cells in the blood. More specifically, light at 417 Nanometers has been found to render the white blood cells and other artifacts transparent to the optics while the red blood cells are readily visible. Thus, it is possible in the preferred embodiment of the invention to eliminate the staining process and the use of color features or logic typically employed in the leukocyte analysis process. It will be appreciated that the present invention is not to be construed as to be limited only to the use of unstained and fixed cells, as described in this preferred embodiment, since it may be possible to develop stains, or adequately control the Wright's staining process and develop appropriate color filtering techniques as an alternative to the preferred sample preparation.

The images of the cells are digitized in a manner known to the art, e.g., U.S. Pat. No. 3,883,852, as a television digitizing system. Magnified blood cell images are obtained by using microscope optics with ultra-violet illumination, arranged to provide a 0.23 micron pixel resolution in the image plane. A pixel is a picture element having a specific location in the digitized image stored in the memory unit of the analyzer.

Figure 4:
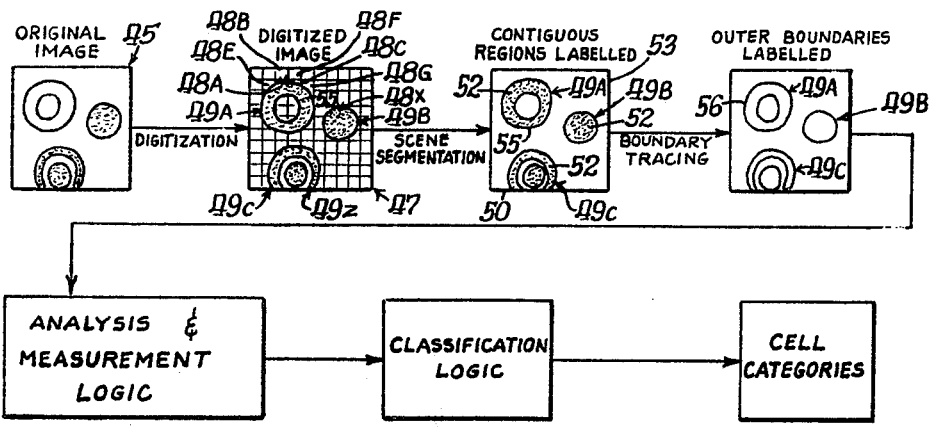
FIG. 4 is a block diagram of the preferred process for analyzing and classifying red blood cells.
Figure 9:
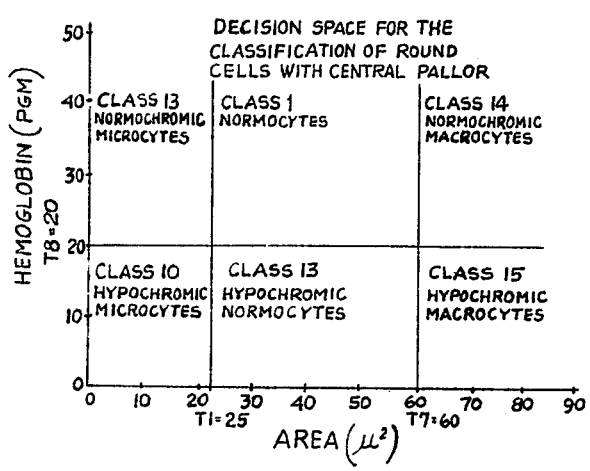
FIG. 9 is a graph illustrating the decision space for the classification of round cells with central pallor using the decision logic of FIG. 5.

Referring now to FIG. 4, an original microscopic image 45 is digitized and this digitized image 47 is stored in the computer 21 for the purpose of further analysis. This analysis is comprised fo five major steps as illustrated in FIG. 4: (1) digitization, the process of quantizing the optical image into a numerical representation (pixels) in a memory store, (2) scene segmentation, the process of identifying in the memory store those pixels which form contiguous regions, each contiguous region representing red cell, (3) tracing the outer boundaries of each contiguous region to form an octal chain code, or list of numbers, which define the outer boundary of the region, (4) compute from this chain code a set of characteristic numbers, or features, and combine these features with others derived during the scene segmentation process, and during an inner boundary trace of the central pallor region, (5) use these features in a classification logic to separate red blood cells into characteristic normal and abnormal categories.

The size of the digitize image may be varied, but herein the size of the digitized image typically will be 132 by 132 picture elements (pixels). After analysis of one digitized image, the stage motor means 23 is operated to shift the slide to present another portion of the slide and other cells for image analysis.

Figure 3:
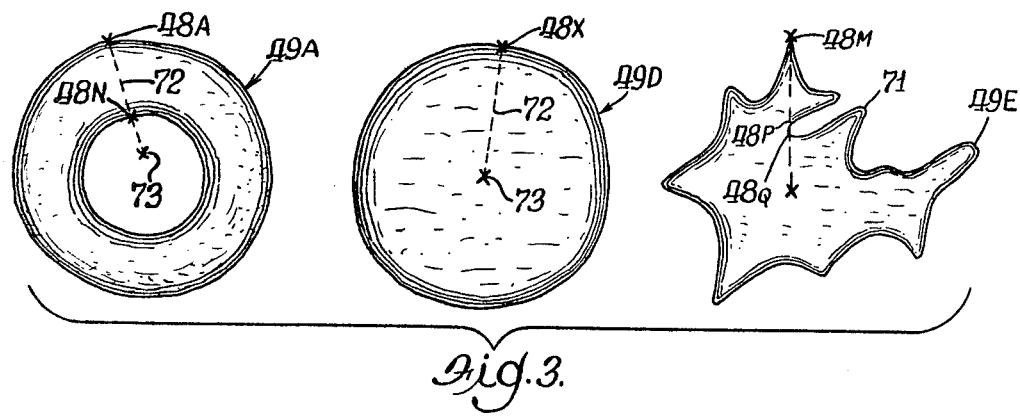
FIG. 3 is an enlarged diagrammatic view of three red blood cells.

In this preferred embodiment of the invention, the individual cells 49A, 49B and 49C in the digitized image 47 are located by a scene analysis technique in which a raster scan is made of the digitized image to locate a pixel 48 above a critical threshold, such as pixel 48A in FIG. 3 and 4, and then to perform a four neighbor analysis of adjacent pixel elements and continuing in a recursive manner locating "neighbors of the neighbors" which are above threshold until the entire region of the cell is defined. This technique is preferred to other scene analysis techniques, such as local boundary following from a gradient image because it is foolproof in distinguishing the true region of a cell particularly those cells having irregular or spiculed projections. Herein, the pixels 48B, 48C, 48D and 48E surrounding the initially located, above threshold pixel 48A and having sides contiguous thereiwth are examined sequentially to identify the next pixel with a grey level value above the threshold. For instance, the pixel 48B located above the pixel 48A is not above the threshold and so it is discarded. The next pixel 48C in a clockwise direction is then examined and it is above threshold. The pixel 48C is then identified in the memory store with the pixel 48A as being a portion of the region of cell 49A. Next, the position of search, around pixel 48A, is stored in a pushdown list and the four neighboring pixels of pixel 48C are examined in the same clockwise order. This continues in a recursive manner until no neighbors are found above threshold for a pixel. At this point, prior pixels on the pushdown list are reexamined to continue the neighbor search process until the entire number of pixels defining a region, i.e., the cell 49A, has been identified. Thus, each of the above threshold pixels of the region is identified in the memory store of the computer and a complete enclosed region has been defined for cell 49A. The pixels within the central pallor area of the cell 49A are not labeled as part of the region for the reason that these central pallor pixels are below threshold. Thus, the sene segmentation technique provides a region 52 for the cell 49A as shown in block 50 of FIG. 4.

Although other histogram or scene analysis techniques may be faster than the above-described technique, these other techniques are more prone to error, by possibly missing some parts of irregularly shaped cells. As will be explained, the area of the central pallor for the cell 49A will be added to the intergrated density for the cell 49A to establish a total hemoglobin content.

Advantageously, the total hemoglobin content for the contiguous regions of the cell 49A except for its central pallor can be obtained during this identification of contiguous regions by summing the grey levels of the pixels as they are identified. Thus, it is possible to provide an integrated optical density therefor. This measure, representing the hemoglobin content for each individual region is stored in a memory 21 for later analysis as a "feature" and also for use in computing subpopulation hemoglobin parameters after the cell 49A has been classified into a particular subpopulation of cells.

The raster scan of the digitized image is then continued to hit the next digitized cell 49B by impacting a pixel 48X which is above the threshold. This contiguous region labeling process is repeated for this cell and the scanning of the digitized image is then continued to locate initial threshold pixel 48Y for the cell 49C and it is labeled initial threshold pixel 48Y for the cell 49C and it is labeled by the same process. During this labeling, it is found that pixel 49Z is on the edge of the scanned image and is also a part of the cell. This cell 49C is then discarded for the reason that part of the cell is on or outside of the scanned image.

The next step in the analysis process is boundary tracing of each labeled object to form an octal chain code, or list of numbers in the memory store, to define the region boundary. This preferred feature analysis technique provides size, roundness, irregularity, spicularity, elongation and central pallor features for subsequent use in classification and they are computed rapidly with simple algorithms and logic from the chain code, not requiring an overly extensive memory. It is to be appreciated that other feature extraction techniques may be used to define the features for later cell classification and still fall within the purview of the present invention.

Figure 8:
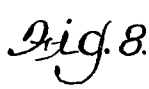
FIG. 8 illustrates an outer boundary labeled cell.

To form this octal chain code, the outer boundaries of the contiguously-labeled pixels, defining a cell, are processed in the following manner. Each pixel element defining the boundary of the cell is stored in a list as a series of numbers indicating a line description of the cell. For instance, referring to FIG. 8, a digital image of a cell as defined by its boundary pixels 48 is to be defined by an octal chain code, in this instance, the octal chain for the cell 60 shown in FIG. 8 is 5,5,6,6,0,0,7,1,2,2,3,2,4 as will be described. The definition of the chain code directions is shown in FIG. 6 relative to the asterisk indicating by number the direction of each one of eight directions for an adjacent contiguous pixel. Thus, the octal chain code for the cell 60, shown in FIG. 8, was made by starting with the upper pixel marked "X". Proceeding to the first counterclockwise pixel which is located downwardly and to the left, or in "5" position shown in FIG. 6. Likewise, the next pixel in the counterclockwise direction is also down and to the left or in a "5" direction. The next two pixels are both straight down or in the "6" direction. So far then, the octal code is 5,5,6,6. The next two counterclockwise pixels are in the same "0" direction. The remaining pixel chain numbers are generated until the chain is completed at point "X".

The chain code has been found to be a powerful feature analysis technique in that it lends itself to ready calculation of four important features, namely, cell size, the perimeter length, an irregularity shape measure and an elongation shape measure. More specifically, the cell size or area is calculated by the number of pixel elements enclosed by the enclosed contour of the boundary cell or object, such as shown in FIG. 7.

With respect to this chain code technique, it can briefly be described by considering that a chain code element $a_i$, which can be an integer from 0 to 7, is of length 1 for even $a_i$ and $\sqrt{2}$ for odd $a_i$. If $n_e$ is the total number of even valued elements, and $n_o$ is the total number of odd elements, then the length of the perimeter (P) is:

$$P = n_e + n_o\sqrt{2}$$

The following relationship exists between the $x,y$ coordinate system, or digitized grid, and the elements $a_i$, of the chain:

| $a_i$ | $a_{ix}$ | $a_{iy}$ |
|---|---|---|
| 0 | 1 | 0 |
| 1 | 1 | 1 |
| 2 | 0 | 1 |
| 3 | −1 | 1 |
| 4 | −1 | 0 |
| 5 | −1 | −1 |
| 6 | 0 | −1 |
| 7 | 1 | −1 |

The area (A) enclosed by the chain code is calculated as:

$$A = |\sum_{i=1}^{n} a_{ix}(y_{i-1} + \frac{1}{2} a_{iy})|$$

where $y_o$ is the initial $y$ value.

As the chain is processed, the original $x$ and $y$ coordinate values are modified by $a_{ix}$ and the maximum and minimum $x$ and $y$ values are determined for the object.

The derivative of the chain code relates to the degree of change from $a_i$ to $a_{i+1}$. This relationship is specified by the following table:

Table 2

|  | $a_i$ | | | | | | | |
|---|---|---|---|---|---|---|---|---|
|  | 0 | 1 | 2 | 3 | 4 | 5 | 6 | 7 |
| 0 | 0 | −1 | −2 | −3 | * | 3 | 2 | 1 |
| 1 | 1 | 0 | −1 | −2 | −3 | * | 3 | 2 |
| 2 | 2 | 1 | 0 | −1 | −2 | −3 | * | 3 |
| 3 | 3 | 2 | 1 | 0 | −1 | −2 | −3 | * |
| $a_{i+1}$ 4 | * | 3 | 2 | 1 | 0 | −1 | −2 | −3 |
| 5 | −3 | * | 3 | 2 | 1 | 0 | −1 | −2 |
| 6 | −2 | −3 | * | 3 | 2 | 1 | 0 | −1 |
| 7 | −1 | −2 | −3 | * | 3 | 2 | 1 | 0 |

The numbers represent the magnitude and direction of the boundary change, and the * indicates impossible conditions.

The irregularity shape measure is computed by following the chain code with the assumption that it should normally form a convex circle, i.e., the octal numbers should follow in the orderly sequence of the chain code itself. Irregularities of number sequences indicate concavities and the number of these irregular sequences is a measure of the number of "spicules" on the boundary of the cell. Tables 3 and 4 describe the logic of this computation. This table was formed from X for ease of processing.

TABLE 3

|  | $a_i$ | | | | | | | |
|---|---|---|---|---|---|---|---|---|
|  | 0 | 1 | 2 | 3 | 4 | 5 | 6 | 7 |
| 0 | 3 | 3 | 1 | 1 | 4 | 2 | 2 | 2 |
| 1 | 2 | 3 | 3 | 1 | 1 | 4 | 2 | 2 |
| 2 | 2 | 2 | 3 | 3 | 1 | 1 | 4 | 2 |
| 3 | 2 | 2 | 2 | 3 | 3 | 1 | 1 | 4 |
| $a_{i+1}$ 4 | 4 | 2 | 2 | 2 | 3 | 3 | 1 | 1 |
| 5 | 1 | 4 | 2 | 2 | 2 | 3 | 3 | 1 |
| 6 | 1 | 1 | 4 | 2 | 2 | 2 | 3 | 3 |
| 7 | 3 | 1 | 1 | 4 | 2 | 2 | 2 | 3 |

The following rules are then used to compute the "number of spicules" feature.

TABLE 4

| Value from Table 3 | Action Taken |
|---|---|
| 1 | Concave move, increment spicule counter, $a_i \rightarrow a_{i+1}$ $a_{i+1} \rightarrow a_{i+2}$ |
| 2 | Convex move, no action taken, |
| 3 | $a_i \rightarrow a_{i+1}$, $a_{i+1} \rightarrow a_{i+2}$ move in same direction, or noise, |
| 4 | $a_{i+1} \rightarrow a_{i+2}$ error |

An elongation shape measure, which is of particular interest in detecting the oblong, sickle and pencil shaped cells, is computed from the chain code by summing the number of each type of element 0 to 7, combining 0 and 4, 1 and 5, 2 and 6, and 3 and 7. This assumes that there are only four orientations possible; (1) parallel, (2) perpendicular, (3) 45°, and (4) 135°. If these sums of the chain codes for each of the four directions are denoted as A to B respectively, then:

A−C > 0 → a parallel object
A−C < 0 → a perpendicular object
B−D > 0 → a 45° object
B−D < 0 → a 135° object If the absolute value of (A−C) is equal to the absolute value of (B−D) the elongation feature takes the value of zero indicating a circular object, otherwise it takes the value of the larger of the two absolute values indicating an elongated object in a specific direction. As will be explained later concerning the classification logic of FIG. 5, if the value of this feature is above a threshold value the cell is elongated.

The chain code analysis also provides the minimum and maximum X and Y directions of the cell. These are used to determine the position of the center of the mass of the cell. This is useful for providing a search direction for finding the central pallor boundary as indicated in FIG. 3.

To distinguish cells which generally have the same size and shape and overall hemoglobin content, but otherwise are distinguished from one another by the presence of differing areas of or the lack of central pallors, such as the cells 49A and 49D, shown in FIG. 3, the present invention provides a central pallor boundary analysis to find and analyze the central pallor 70. The central pallor analysis utilizes a chain code procedure in the same manner as the outer boundary was analyzed. Having defined the existence of the central pallor and its boundary, a list of features for the central pallor assist in the proper classification of the cells. For instance, the classification using the central pallor features is of particular utility in distinguishing target cells from normochromic microcytes with central pallor, normocytes with central pallor, and normochromic macrocytes with central pallor.

Referring now to FIG. 3, there are illustrated three different cells 49A, 49D, and 49E with the feature logic searching and direction along a line 72 from the respective initial raster scan threshold points 48A, 48X, and 48M toward their centers of mass 73 looking for a threshold condition, such as the pixel 48N for the cell 49A. The cell 49D, of course, lacks a central pallor, and, therefore, there will be no hit of a below threshold pixel before the center of mass 73 is reached. For the irregular shaped cell 49E, the hit of above threshold values at 48P and 48Q are previously labelled outer boundary pixels and will be discounted as central pallor pixels. The search will continue through to the center of mass 73 for the cell 49E without impacting a central pallor threshold. If more than one internal boundary is found before reaching the center of mass point 73, then the target flag feature is set. The initial chain code, as above described, is then formed for the central pallor boundary 70 for the cell 49A, and the calculations, above set forth, are made for this central pallor chain code to provide the features of pallor size, pallor perimeter length, pallor irregularity shape measure, and pallor elongation shape measure.

The above features may also be combined to provide further features for use in the classification of the cells by their features. In this regard, the following features are used herein:

TABLE 5

| Feature | Description | How Determined |
|---|---|---|
| F1 | Area size | Number of pixels enclosed by cell boundary |
| F2 | Shape (circularity) | (Number of perimeter pixels)$^2$/area |
| F3 | Shape (spicularity) | Number of "spicules" on boundary |
| F4 | shape (elongation) | Comparison of orthogonal boundary chain code orientations |
| F5 | Σ grey levels | Sum of grey levels as a measure of Cell Hemoglobin (CH) |
| F6 | Pallor (area size) | Number of pixels enclosed by pallor boundary |
| F7 | Pallor (circularity) | (Number of pallor boundary pixels)$^2$/area |
| F8 | Pallor (target flag) | Set if search to center of cell crosses inner threshold |
| F9 | Pallor (grey level) | Edge of cell grey level minus center of cell grey level |
| F10 | Σ grey A measure of Cell Hemoglobin | |

| TABLE 5-continued | | |
|---|---|---|
| Feature | Description | How Determined |
| | (levels area | Density (CHD), i.e. F5/F1 |

While feature F1 relates to the area or size of the cell as determined by the number of picture elements or pixels that are enclosed by the cell boundary, feature F2 is the boundary perimeter$^2$/area and is of assistance in classifying round and non-round objects. A round object would have a value of $4\pi$ and non-round objects necessarily have a value greater than $4\pi$. As previously mentioned, features F3 and F4 relate to the spicularity and elongation shapes, respectively, and feature F5 is the integrated optical density of the cell. It is the sum of the grey levels within the enclosed boundaries, i.e., within the enclosed outer boundaries, but not including the enclosed central pallor boundary, if one exists in the cell. Feature F6, which is a measure of the pallor size, assists in distinguishing cells with large pallors, such as normochromic macrocytes from hypochromic macrocytes with larger central pallors. Feature F7 determines the degree of roundness of the pallor itself and is also used to set the target flag feature. Feature F8, which is the target flag, is set if an inner grey level area is present during the search to the cell center, i.e., it is set if a threshold is crossed twice. Feature F9 is a measure of the presence of, as well as the depth of the central pallor, and is determined by an analysis of the difference between the grey level of the edge and the grey level of the center. A sum of the grey levels divided by the cell size provides an indication of the hemoglobin concentration for the cell and this feature is identified as feature F10.

The logic decisions for determining the various features that have been briefly described are carried out by the logic circuitry 21 and 22 using the logic flow chart shown in FIG. 5. The logic decisions are made using various features together with threshold values that are identified as T1 through T12. The thresholds T1-T12 are described in Table 6 and specific values are also provided. As shown therein, the thresholds are used by the logic with the various features in making logic decisions leading to the classification of the cell of interest in accordance with the flow chart shown in FIG. 5. In this regard, FIG. 5 illustrates various decisions that are made on the basis of various features either exceeding or being less than certain threshold values as will be specifically described. Moreover, the classification of cells into specific classes is ultimately performed and FIG. 5 also illustrates a pictorial representation of a typical cell of each class, with the classes conforming to those shown in Table 1.

Referring to FIG. 5 in detail, a cell that is to be classified is first examined by logic section 80 to determine if the cell is sufficiently large to be further analyzed. If feature F1, which is the size or area of the cell under consideration, is less than the threshold value T11 which may be a value of about 6 microns$^2$, then the cell is not considered by the decision logic and another cell will be advanced for analysis and classification. However, if the area of the cell is greater than the lower boundary threshold value T11, the decision logic then operates to determine whether it is a round or non-round cell. This is performed by a logic section, indicated generally at 82, which includes logic subsections 84, 86 and 88. The subsections 84, 86 and 88 are operable to jointly make the roundness determination with the features F2, F3 and F4 being examined with respect to thresholds T2, T3 and T4. If the cell has a small roundness value, a small spiculated value and a small elongated value, then it is considered to be round and passes on to the logic subsection 90 which determines whether the cell has central pallor. Similarly, if it is determined that the cell is not round, then logic subsection 92 operates to determine if the size of the cell exceeds an upper boundary threshold T12, and if it does, the cell is not further analyzed and a new cell will be considered. The effect of the subsection 92 is to eliminate double cells such as that shown in the pictorial representation 94. It should be appreciated from the pictorial representation that such a double cell would not pass the roundness test, but it is also not a non-round cell of the type shown in pictorial representation for cells of classes 6 through 8. Thus, it cannot be accurately classified and it is for this reason that the subsection 92 eliminates such cells from further consideration.

As previously mentioned, the roundness of the cell is determined by feature F2 which will have a value of $4\pi$ for a perfect circle and will increase as the shape of the cell departs from circular. Thus, the threshold value T2 is chosen to reflect reasonably good circularity and if the feature F2 exceeds the threshold T2, that is an indication that the shape is not circular, hence the logical flow to subsection 92 indicating that the object is not round. If feature F2 is not greater than threshold T2, it is one indication that the cell is round and if the decision from subsections 86 and 88 also indicate adequate roundness, the logic flow then proceeds to logic subsection 90.

Even though the cell being examined may have a boundary perimeter$^2$/size feature indicative of its general roundness, the cell may be spiculed, e.g., a burr cell, and its spicularity input at logic subsection 86 will so indicate that the burr cell is highly spiculed and cause the cell to be sent for further classification by logic subsection 88. Likewise, the highly elongated cells such as sickle cells will be sent to a separate logic section, indicated generally at 96, for further classification as their elongation index input feature F4 will indicate that the cell is not round. Thus, it should be understood that a rigorous test of each of the three shape feature F2, F3 and F4 must be met before a cell is classified as being round or non-round.

The logic section 82 first operates to determine the roundness of the cell prior to subjecting the cell to the logic subsection 92 because size alone may not provide a good indication as to the presence of a double cell and round cells can and do have a total area that is greater than the threshold level T12. It has been found however, that non-round cells do not exceed the threshold size of about 54$\mu^2$.

In the event the non-round cell is below the size determined by threshold T12, it is further classified by the logic section 96 and is initially applied to logic subsection 98 which determines the degree of spicularity of the cell. If the cell is highly spiculed, i.e., feature F3 exceeds the threshold T3 of 7 spicules on the boundary of the cell, it is then examined for elongation by logic subsection 100 which determines the elongation of the cell. The subsection 100 differentiates irregularly shaped cells, e.g., helmet-shaped cells and the like, from elongated spiculed cells. Thus, the elongation index of feature F4 exceeding the threshold T4 will differentiate these elongated cells and classify them into class 5, that being elongated spiculed cells. If feature F4 is less than threshold T4, the cells will be placed in class 6, which are spiculed, irregularly shaped cells.

In the event logic subsection 98 determines that the cell is not excessively spiculed, then logic subsection 102 operates to examine feature F4 with respect to threshold value T4 and thereby separate nonspiculed, irregularly shaped cells from nonspiculed elongated cells. Thus, an elongation index input feature F4 for the cell is used by logic subsection 102 to classify the nonelongated cells into class 8, i.e., irregular shaped cells, and elongated cells are classified in class 7. In this regard, sickle cells, pencil forms and elliptocytes are classified in class 7.

Figure 10:
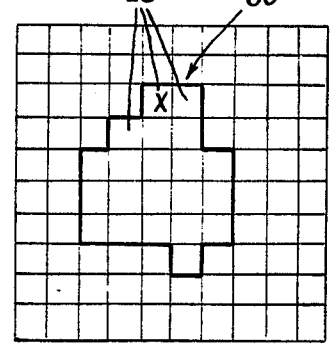

Referring again to the logic subsection 90, it determines the presence or absence of central pallor in the round cell by comparing the feature F9 with the threshold T10 and determines the presence of central pallor when feature F9 exceeds the threshold T10. The feature F9 is determined by subtracting the center of the cell grey level from the edge of the cell grey level. Stated in other words, threshold T10 is the magnitude of the edge to center of grey level difference and it may have a value of about 5. This grey level difference corresponds to approximately 0.4 microns of cell thickness. The average cell thickness is about 2.2 microns. The feature can be more readily appreciated by reference to FIG. 10 which illustrates three separate graphs for three different, typically occurring cell types. In each case, the height of the curve represents the grey level as a function of distance across the cell passing through the cell center. The edge grey level measurement is made approximately three pixels inwardly from the initial edge pixel. The center grey level measurement is made at the center of mass, preferably, computed from the maximum $x$ and $y$ extensions of the cell. Thus, FIG. 10$a$ illustrates a typical red cell with a well developed central pallor; FIG. 10$b$ illustrates an intermediate central pallor development with a difference that is greater than threshold T10; and, FIG. 10$c$ illustrates a "flat" cell which has virtually no central pallor development, i.e., the grey level is uniform throughout the cell.

Once the logic subsection 90 determines that there is no central pallor development, then the cell is operated on by logic section 104 which classifies round cells having no central pallor. This section classifies the cells as to their size and by their hemoglobin content in the following manner. Logic subsection 106 is operative to determine those cells that are very small. If feature F1, the area of the cell, is less than threshold T1, i.e., less than about 25 microns$^2$, the cell is classified as being in class 4, that of spherocytes. If the cell area is greater than about 25 microns$^2$, logic subsection 108 operates to determine if feature F10 is greater than the threshold T9. This is a measure of the cell hemoglobin density (CHD) and is determined by dividing feature F5 by feature F1 and multiplying by 100. The threshold value T9 is preferably about 83. If the density exceeds the threshold value, then the cell is also classified as a spherocyte in class 4. However, if the density does not exceed the threshold value T9, then logic subsection 110 determines if the size of the cell exceeds threshold value T7, which is preferably approximately 60 microns$^2$. If it exceeds 60 microns$^2$, it is placed in class 3, that of macrocytes without central pallor. If the size of the cell is less than 60 microns$^2$, it is classified in class 2, normocytes without central pallor.

If the logic subsection 90 indicates that the cell does have central pallor, then it is forwarded to logic section 112 which further classifies the cell by the size, shape and density of the central pallor. Initially, logic subsection 114 operates to determine if feature F6, the area of the pallor, is less than threshold T5 which is preferably about 10 microns$^2$. If logic subsection 114 determines that the size of the pallor is not less than the threshold value, then it is applied to subsection 116 to determine if the pallor is round. This is done by comparing feature F7, that of the circularity of the pallor to determine if it is less than the threshold value T6 which is preferably about 16. Thus, the large pallor cells are examined to see if their respective central pallors are round and, if the central pallor is round, the cell is further classified by logic subsection 118 to see if the target flag feature F8 is set. If a target flag is set, then the cell is classified in class 9 as being a target cell. However, if the target flag is not set, then logic subsection 120 operates on the cell to compare the cell homoglobin (CH) of the cell, feature F5, to determine if it is less than the threshold T8 which is preferably about 20 picograms. If the hemoglobin content is determined to be low, then logic subsection 122 classifies the cell as to size by determining if the size feature F1 is less then threshold T1, i.e., 25 microns$^2$. If it is smaller than this value, it is classified in class 10, that of the hypochromic microcytes. However, if the size exceeds 25 microns$^2$, logic subsection 124 operates to determine if the cell is too large by determining if the area exceeds the threshold T7, which is about 60 microns$^2$ as previously mentioned. In the event it is larger than 60 microns$^2$, it is classified in class 12, hypochromic macrocytes, and if it is smaller than the 60 microns$^2$ value, it is classified into class 11, that of hypochromic normocytes.

If logic subsection 120 determines that the cell does not have low hemoglobin content, then logic subsection 126 operates to again determine whether the size of the cell is less than the 25 microns$^2$, i.e., whether feature F1 is less than threshold value T1. If the cell is smaller than the threshold value, it is classified into class 13, that of normochromic macrocytes. If it is larger than 25 microns, then logic subsection 128 operates to determine if it is greater or less than the 60 microns$^2$ threshold value of T7. If the cell is larger than 60 microns$^2$, it is classified into class 14, normochromic macrocytes, and if it is less than the threshold value, it is classified into class 1, namely, normocytes. It should be appreciated from the pictorial representations for cells in classes 1 and 9 through 14 that all of the cells in these classes have central pallor.

While the determination of the various features and decisions contained in the logic flow diagram of FIG. 5 are carried out using the threshold values contained in Table 6, it should be understood that the threshold values are based upon empirical and statistical analysis and can be varied slightly without appreciably affecting the eventual classification of the cells. If should also be appreciated that the threshold values are believed to be optimum values which have been fixed to maximize the accuracy of the classification.

While the format of Table 6 fully defines and describes the thresholds, reference is also made to FIGS. 9 through 15 which are graphs of the decision space for the classification of cells. More specifically, reference is made to FIG. 9 which is the decision space for the classification of round cells having central pallor and reflects hemoglobin in picograms on the ordinate plotted against area in microns$^2$ on the abscissa. The vertical lines shown at 25 and 60 microns$^2$ are the threshold values of T1 and T7, respectively. A horizontal line at 20 picograms for the hemoglobin is the value of the threshold T8. The three lines reflect decisions that are performed by the logic circuitry and it divides the cells into six classes which are labelled in the drawing. Similarly, FIG. 11 is a graph of the decision space for the classification of round cells having no central pallor and illustrates the classification of spherocytes, normocytes without central pallor and macrocytes without central pallor. FIG. 13 is a graph of hemoglobin vs. area and illustrates the decision space for classification of round cells with central pallor including about 70 measurements from a normal specimen. Thus, the normal specimen decision space will comprise cells having a size within the range of about 25 to about 60 microns$^2$ and will have a hemoglobin content greater than 20 picograms. FIG. 12 illustrates about 70 measurements from a patient having iron deficiency anemia and it is seen that the size of the cells is generally smaller and that they also have a lesser hemoglobin content. FIG. 14 illustrates about 70 measurements from a patient having megoloblastic anemia which have a generally higher hemoglobin content and also a larger area. FIG. 15 represents two graphs using about 200 measurements from a hereditary spherocytosis patient. The distribution of the measurements are close to those of a normal specimen for the round cells with central pallor. However, it should be appreciated that the measurements plotted in FIG. 15b are for cells having no central pallor in contrast with a normal cell that does generally have central pallor.

TABLE 6

Description of Threshold Values for use with Red Cell Features F1 to F10 to Classify Red Cells According to the Logic of FIG. 5.

| thre- | Values | Description |
|---|---|---|
| T1 | $25\mu^2$ | Lower boundary for Small Cell Areas, used with F1 |
| T2 | 16 | Upper boundary for Cell Circularity, used with F2 |
| T3 | 7 | Upper boundary for the number of Cell Spicules, used with F3 |
| T4 | 19 | Upper boundary for elongation index, used with F4 |
| T5 | $10\mu^2$ | Lower boundary for central pallor area used with F6 |
| T6 | 16 | Upper boundary for central pallor circularity used with F7 |
| T7 | $60\mu^2$ | Upper boundary for cell area, used with F1 |
| T8 | 20 pg | Lower boundary for Cell Hemoglobin, used with F5 |
| T9 | 83 pg/$\mu^2$ | Upper boundary for Cell Hemoglobin Density used with F10 |
| T10 | 5 | Magnitude of the edge to center of cell grey level difference, for central pallor definition, used with F9. |
| T11 | $6\mu^2$ | Lower boundary for objects to be analyzed. Objects with areas less than T11 are not considered by the decision logic. |
| T12 | $54\mu^2$ | Upper boundary for objects to be analyzed. Non-round objects, with areas greater than T12 are rejected by the decision logic. |

The classification system described above in connection with the diagram shown in FIG. 5 is preferred to the usual standard multivariate Guassian classification technique which requires a larger number of test samples of the blood cells to determine the covariance matrix. Moreover, the binary method described results in classification decisions which are fast in contrast.

It will be appreciated that in addition to providing a fast and efficient classification this method implements or results in a sort of descriptive or linguistic classification of cells. By this linguistic system is meant a first descriptive category, modified by second and third descriptive categories the final descriptive terminology being determined by the classification logic to agree with standard hematological terminology. For example, the first descriptive category could be by size, with second and third modifiers according to color, shape or internal central pallor configurations. Using this method in connection with the logic of FIG. 5 results in the descriptive classes of Table I, where only of course those subpopulations actually present and detected in the specimen are printed out. Alternatively, it is also possible to classify the cells by other unique and mutually exclusive linguistic combinations of their measured features. For example, a reduced subset of only size, color and shape may be used. The size may be simply divided into microcytic, normocytic or macrocytic. The color being measured and simply divided into hypochromic, normochromic or hyperchromic. Additionally, the shape feature may be measured and identified as either round or nonround (poikilocytic). With such features it is possible to analyze each cell and provide a classification scheme as follows:

| Size | Micro (1) | Normo (2) | Macro (3) |
|---|---|---|---|
| Color | Hypochromic (A) | Normo (B) | Hyper (C) |
| Poikilocytic | Round ($\alpha$) | Poikilocytic ($\beta$) | |
| 1 A $\alpha$ | Microcytic Hypochromic | | |
| 1 A $\beta$ | Microcytic Hypochromic, poikilocytic | | |
| 1 B $\alpha$ | Microcytic | | |
| 1 B $\beta$ | Microcytic, poikilocytic | | |
| 1 C $\alpha$ | Microcytic, Hyperchromic | | |
| 1 C $\beta$ | Microcytic, Hyperchromic, poikilocytic | | |
| 2 A $\alpha$ | Hypochromic | | |
| 2 A $\beta$ | Hypochromic, poikilocytic | | |
| 2 B $\alpha$ | Normocytic | | |
| 2 B $\beta$ | Poikilocytic | | |
| 2 C $\alpha$ | Hyperchromic | | |
| 2 C $\beta$ | Hyperchromic, poikilocytic | | |
| 3 A $\alpha$ | Macrocytic, Hypochromic | | |
| 3 A $\beta$ | Macrocytic, Hypochromic, poikilocytic | | |
| 3 B $\alpha$ | Macrocytic | | |
| 3 B $\beta$ | Macrocytic, poikilocytic | | |
| 3 C $\alpha$ | Macrocytic, Hyperchromic | | |
| 3 C $\beta$ | Macrocytic, Hyperchromic, poikilocytic | | |

By this scheme a descriptive size classification is normally reported in the first column, a color characteristic in the second and a shape characteristic in the third. The symbols (e.g. 3 A$\alpha$) are used only by way of illustration to indicate combinations of the categories. Again, only those categories actually present would be printed out. This may also of course include such measured quantities as the percent or number of cells present in each subpopulation or hemoglobin and size characteristics of each subpopulation. However, what is meant to be illustrated as one of the novel aspects of this invention is the use of logic to make variable strings of descriptors of cell subpopulations, reported out in a variable length format according to which subpopulations are present, but including a complete hematologically descriptive, variable length phrase, which describes each subpopulation of cells present.

Note that the secondly described classification scheme is a subset of the previous scheme in that it does not provide the refined classification by an examination of the interior cell region as preferred, to provide a more refined system analysis of center of the cells to distinguish accurately target cells from normocytes or macrocytes and to distinguish accurately spherocytes from microcytes, even though it does provide the descriptive linguistic classification of subpopulations.

Also, while the preferred embodiment of the invention divides the cells into mutually exclusive subpopulations, it is also possible to classify the red blood cells more grossly by shape, size and color, and count merely the numbers of cells having a particular shape, irrespective of the fact that it may also have been counted by its size in another category and by its color in still a third category.

By way of example only, several examples of the print out of blood analyzed by the preferred method and apparatus will be given. Examples I, II and III are labeled to indicate the kind of anemia which would be indicated by the cells found in the individual blood and the reported parameters therefor. Example IV indicates printout for a sample of normal blood.

EXAMPLE I

Iron Deficiency Anemia

| % | Description | Size ($\mu^2$) | MCH (pg) | MCHD (pg/$\mu^2$) |
|---|---|---|---|---|
| 53 | NORMOCYTES WITH CENTRAL PALLOR | 38 | 18 | 47 |
| 1 | HYPOCHROMIC NORMOCYTES WITHOUT CENTRAL PALLOR | 29 | 20 | 69 |
| 1 | SPHEROCYTES | 27 | 19 | 70 |
| 4 | ELONGATED CELLS | 20 | 11 | 55 |
| 4 | IRREGULAR SHAPED CELLS | 29 | 13 | 45 |
| 4 | TARGET CELLS | 41 | 11 | 27 |
| 1 | HYPOCHROMIC MICROCYTES, WITH CENTRAL PALLOR | 22 | 17 | 77 |
| 32 | HYPOCHROMIC NORMOCYTES, WITH CENTRAL PALLOR | 38 | 15 | 39 |

EXAMPLE II

Anemia of Inflammation

| % | Description | Size ($\mu^2$) | MCH (pg) | MCHD (pg/$\mu^2$) |
|---|---|---|---|---|
| 71 | NORMOCYTES WITH CENTRAL PALLOR | 46 | 26 | 57 |
| 8 | NORMOCYTES WITHOUT CENTRAL PALLOR | 48 | 34 | 71 |
| 1 | HYPOCHROMIC NORMOCYTES WITHOUT CENTRAL PALLOR | 41 | 16 | 39 |
| 9 | ELONGATED CELLS | 40 | 24 | 60 |
| 2 | IRREGULAR SHAPED CELLS | 35 | 21 | 60 |
| 9 | HYPOCHROMIC NORMOCYTES, WITH CENTRAL PALLOR | 37 | 20 | 54 |
| 1 | NORMOCHROMIC MACROCYTES, WITH CENTRAL PALLOR | 72 | 40 | 56 |

EXAMPLE III

Mechanical Valve Induced Intravascular Hemolysis

| % | Description | Size ($\mu^2$) | MCH (pg) | MCHD (pg/$\mu^2$) |
|---|---|---|---|---|
| 42 | NORMOCYTES WITH CENTRAL PALLOR | 46 | 30 | 65 |
| 30 | NORMOCYTES WITHOUT CENTRAL PALLOR | 48 | 33 | 69 |
| 1 | HYPOCHROMIC NORMOCYTES WITHOUT CENTRAL PALLOR | 41 | 22 | 54 |
| 1 | HYPERCHROMIC NORMOCYTES WITHOUT CENTRAL PALLOR | 55 | 44 | 80 |
| 6 | SPHEROCYTES | 36 | 32 | 89 |
| 12 | ELONGATED CELLS | 35 | 22 | 63 |
| 5 | IRREGULAR SHAPED CELLS | 37 | 24 | 65 |
| 2 | HYPOCHROMIC NORMOCYTES, WITH CENTRAL PALLOR | 33 | 21 | 64 |
| 1 | NORMOCHROMIC MACROCYTES, WITH CENTRAL PALLOR | 66 | 42 | 64 |

EXAMPLE IV

Normal

| % | Description | Size ($\mu^2$) | MCH (pg) | MCHD (pg/$\mu^2$) |
|---|---|---|---|---|
| 98 | NORMOCYTES WITH | 46 | 29 | 63 |
| 1 | ELONGATED CELLS | 42 | 22 | 52 |
| | HYPOCHROMIC NORMOCYTES, WITH CENTRAL PALLOR | 33 | 19 | 58 |

It will be appreciated from the foregoing that coherent optical analysis equipment, liquid flow process equipment or other equipment may be used in lieu of the disclosed microscopic digital image analysis equipment illustrated herein to practice the method of invention by way of examining the red blood cells for their distinctive features and classifying the red blood cells into normal and abnormal subpopulations. Furthermore, other equipment, and methods of examination of cell's internal regions may be used to provide hemoglobin characteristics for the individual cell subpopulations rather than using the preferred and illustrated equipment and methods described herein. Also, as explained hereinbefore, the equipment and methods to classify the red blood cells by their features may be varied considerably from that disclosed herein by way of illustration and still fall within the purview of the appended claims.

The automated method and apparatus of the present invention operate on a higher level than the human eye and human brain to make those fine distinctions between red blood cells based on their densities, central pallor sizes and cell diameters that are not recognizable by the usual manual methods. For the first time it is possible to classify and quantify red blood cells in a refined manner comparable to that by which white blood cells heretofore have been quantified. The art of quantification and classification of white blood cells by manual methods was well known and well developed prior to the development of the automated equipment as the white blood cells are characterized when stained by easily recognized color and shape patterns which are able to be taught and recognized by persons after several weeks of training. However, the red blood cells do not provide such color patterns and gross distinctions in size and shape that they may be manually quantified in the way that white blood cells have been. Thus, as was described earlier, the typical red blood cell analyses involves generalizations such as poikilocytoses without a count of cells in a given abnormal subpopulation or the hemoglobin or size characteristics of the cells in the various abnormal cell classifications observed.

The methods used to automatically analyze white blood cells is not readily adaptable to red blood cells and hence new methods of boundary analysis and central region analyses were devised to provide the fine distinctions desired to classify red blood cells, particularly into mutually exclusive subpopulations, and to make distinctions finer than the human eye.

From the foregoing, it will be seen that diagnosis of red blood cell hematological disorders may be enhanced by the present invention's generation of more detailed and more accurate information of the kinds of and quantities of abnormal cells present. Specific information provided by the invention on the hemoglobin characteristics of mutually exclusive cell subpopulations also should provide a new and important diagnostic aid heretofore not available to clinicians. The automation of the recognition classification of red blood cells provides a more efficient and faster manner of diagnosis of anemia and other diseases and should result in greater use of red blood cell analysis by clinicians.

While a preferred embodiment has been shown and described, it will be understood that there is no intent to limit the invention by such disclosure but, rather, it is intended to cover all modifications and alternate constructions falling within the spirit and scope of the invention as defined in the appended claims.

The logic circuitry 21 and 22 that carry out the flow diagram of FIG. 5 may comprise a computer such as the Digital Equipment Corporation PDP 11/20 minicomputer. In such event, the listings shown in Appendix I can be used for implementing the flow diagram of FIG. 5 using the features described herein together with the threshold values that have been previously set forth. The listing is of the binary load module as it would be loaded into the minicomputer from the disk operating system (DOS) monitor. The listing is produced by the Standard FILDMP program as described in the DOS/BATCH Handbook, published by Digital Equipment Co., 1974, with the IFB option.

APPENDIX I

```
REDS  .LDA  (OCTAL)

000000  000 001 000040
        036710  006001  036710  056116  036710  000000  000000  050561
        055740  000000  000000  000000  000000  003721  000002  000000
000001  000 001 000024
        036710  004467  052034  106176  000000  000000  050561  055740
        073570  041602
000002  000 001 000050
        040202  047516  046522  041517  052131  051505  053440  052111
        020110  042503  052116  040522  020114  040520  046114  051117
        020040  020040  020040  020040
000003  000 001 000050
        040250  020040  020040  020040  020040  020040  047516  046522
        041517  052131  051505  053440  052111  047510  052125  041440
        047105  051124  046101  050040
000004  000 001 000050
        040316  046101  047514  020122  020040  020040  020040  020040
        020040  020040  020040  040515  051103  041517  052131  051505
        053440  052111  047510  052125
000005  000 001 000050
        040364  041440  047105  051124  046101  050040  046101  047514
        020122  020040  020040  020040  020040  020040  020040  020040
        054510  047520  044103  047522
000006  000 001 000050
        040432  044515  020103  047516  046522  041517  052131  051505
        053440  052111  047510  052125  041440  047105  051124  046101
        050040  046101  047514  020122
000007  000 001 000050
        040500  020040  054510  042520  041522  051110  046517  041511
        047040  051117  047515  054503  042524  020123  044527  044124
        052517  020124  042503  052116
000010  000 001 000050
        040546  040522  020114  040520  046114  051117  020040  050123
        042510  047522  054503  042524  020123  020040  020040  020040
        020040  020040  020040  020040
000011  000 001 000050
        040614  020040  020040  020040  020040  020040  020040  020040
        020040  020040  020040  020040  046105  047117  040507  042524
        026104  051440  044520  052503
000012  000 001 000050
        040662  042514  020104  042503  046114  020123  020040  020040
```

```
                020040  020040  020040  020040  020040  020040  020040  020040
                020040  050123  041511  046125
        000013  000 001 000050
                040730  042105  020054  051111  042522  052507  040514  020122
                044123  050101  042105  020040  042503  046114  020123  020040
                020040  020040  020040  020040
        000014  000 001 000050
                040776  020040  020040  046105  047117  040507  042524  020104
                042503  046114  020123  020040  020040  020040  020040  020040
                020040  020040  020040  020040
        000015  000 001 000050
                041044  020040  020040  020040  020040  020040  020040  020040
                051111  042522  052507  040514  020122  044123  050101  042105
                041440  046105  051514  020040
        000016  000 001 000050
                041112  020040  020040  020040  020040  020040  020040  020040

020040  020040  020040  020040  020040  040524  043522  052105
                041440  046105  051514  020040
        000017  000 001 000050
                041160  020040  020040  020040  020040  020040  020040  020040
                020040  020040  020040  020040  020040  020040  020040  020040
                020040  020040  054510  047520
        000020  000 001 000050
                041226  044103  047522  044515  020103  044515  051103  041517
                052131  051505  020054  044527  044124  041440  047105  051124
                046101  050040  046101  047514
        000021  000 001 000050
                041274  020122  020040  020040  054510  047520  044103  047522
                044515  020103  047516  046522  041517  052131  051505  020054
                044527  044124  041440  047105
        000022  000 001 000050
                041342  051124  046101  050040  046101  047514  020122  020040
                020040  054510  047520  044103  047522  044515  020103  040515
                051103  041517  052131  051505
        000023  000 001 000050
                041410  020054  044527  044124  041440  047105  051124  046101
                050040  046101  047514  020122  020040  020040  047516  046522
                041517  051110  046517  041511
        000024  000 001 000050
                041456  046440  041511  047522  054503  042524  026123  053440
                052111  020110  042503  052116  040522  020114  040520  046114
                051117  020040  020040  047516
        000025  000 001 000050
                041524  046522  041517  051110  046517  041511  046440  041501
                047522  054503  042524  026123  053440  052111  020110  042503
                052116  040522  020114  040520
        000026  000 001 000036
                041572  046114  051117  020040  020040  110766  000011  104766
                051452  051454  051456  051460  110766  000012  051462
        000027  000 001 000024
                041626  051472  106334  050264  074070  110766  000013  051462
                051502  106334
        000030  000 001 000026
                041650  050266  074070  110766  000014  051512  073364  051522
                110766  000015  051472
        000031  000 001 000024
                041674  073364  051524  110766  000016  051526  073364  115032
                110766  000017
        000032  000 001 000022
                041716  051526  073364  115034  110766  000020  051334  051342
                106474
        000033  000 001 000020
                041736  073364  115036  110766  000021  051472  074100  115040
        000034  000 001 000026
                041754  110766  000022  051512  073364  051536  110766  000023
                050244  074056  051350
        000035  000 001 000020
                042000  106474  051472  073474  051502  107726  051540  073474
        000036  000 001 000024
                042016  073364  115030  110766  000024  051550  073364  051560
                110766  000025
        000037  000 001 000026
                042040  051462  073364  051562  110766  000026  051564  073364
                051574  110766  000027
        000040  000 001 000026
                042064  051472  073364  051576  110766  000030  051600  073364
                051610  110766  000031
        000041  000 001 000026
                042110  051612  073364  051622  110766  000032  051472  073364
                051632  110766  000033
        000042  000 001 000022
                042134  051512  051624  106334  050504  073442  073654  051500
                051632
        000043  000 001 000024
                042154  051642  042130  110766  000034  051644  051472  106334
                050434  073442
```

| | | | | | | | | | |
|---|---|---|---|---|---|---|---|---|---|
| 000044 | 000 001 | 000026 | | | | | | | |
| | 042176 | 110766 | 000035 | 051654 | 051502 | 106334 | 050434 | 073442 | |
| | 110766 | 000036 | 051444 | | | | | | |
| 000045 | 000 001 | 000024 | | | | | | | |
| | 042222 | 051664 | 106334 | 050434 | 073442 | 110766 | 000037 | 051674 | |
| | 051600 | 106334 | | | | | | | |
| 000046 | 000 001 | 000024 | | | | | | | |
| | 042244 | 050434 | 073442 | 110766 | 000040 | 051704 | 051634 | 106334 | |
| | 050434 | 073442 | | | | | | | |
| 000047 | 000 001 | 000026 | | | | | | | |
| | 042266 | 110766 | 000041 | 051714 | 051724 | 106334 | 050434 | 073442 | |
| | 110766 | 000042 | 051734 | | | | | | |
| 000050 | 000 001 | 000024 | | | | | | | |
| | 042312 | 051444 | 106334 | 050434 | 073442 | 110766 | 000043 | 051744 | |
| | 051754 | 106334 | | | | | | | |
| 000051 | 000 001 | 000024 | | | | | | | |
| | 042334 | 050434 | 073442 | 110766 | 000044 | 051764 | 051774 | 106334 | |
| | 050434 | 073442 | | | | | | | |
| 000052 | 000 001 | 000026 | | | | | | | |
| | 042356 | 110766 | 000045 | 052004 | 052014 | 106334 | 050434 | 073442 | |
| | 110766 | 000046 | 052024 | | | | | | |
| 000053 | 000 001 | 000024 | | | | | | | |
| | 042402 | 051462 | 106334 | 050434 | 073442 | 110766 | 000047 | 051472 | |
| | 073364 | 052042 | | | | | | | |
| 000054 | 000 001 | 000024 | | | | | | | |
| | 042424 | 110766 | 000050 | 051512 | 052034 | 106334 | 050310 | 073442 | |
| | 073654 | 051500 | | | | | | | |
| 000055 | 000 001 | 000026 | | | | | | | |
| | 042446 | 052042 | 051452 | 042424 | 110766 | 000051 | 051472 | 073364 | |
| | 051632 | 110766 | 000052 | | | | | | |
| 000056 | 000 001 | 000024 | | | | | | | |
| | 042472 | 051472 | 073364 | 052042 | 110766 | 000053 | 052046 | 052034 | |
| | 051624 | 106342 | | | | | | | |
| 000057 | 000 001 | 000022 | | | | | | | |
| | 042514 | 051006 | 073440 | 073654 | 051500 | 052042 | 051672 | 042500 | |
| | 073654 | | | | | | | | |
| 000060 | 000 001 | 000026 | | | | | | | |
| | 042534 | 051500 | 051632 | 052044 | 042466 | 110766 | 000054 | 114576 | |
| | 105104 | 000406 | 051452 | | | | | | |
| 000061 | 000 001 | 000026 | | | | | | | |
| | 042560 | 052060 | 052100 | 052102 | 051520 | 037050 | 004467 | 052022 | |
| | 110766 | 000055 | 051472 | | | | | | |
| 000062 | 000 001 | 000026 | | | | | | | |
| | 042604 | 073364 | 052114 | 110766 | 000056 | 051472 | 073364 | 052116 | |
| | 110766 | 000057 | 051502 | | | | | | |
| 000063 | 000 001 | 000022 | | | | | | | |
| | 042630 | 073364 | 052120 | 110766 | 000060 | 073470 | 052116 | 073470 | |
| | 042670 | | | | | | | | |
| 000064 | 000 001 | 000050 | | | | | | | |
| | 042650 | 076306 | 000000 | 000000 | 103564 | 110766 | 000061 | 073570 | |
| | 042736 | 030450 | 020110 | 023454 | 047105 | 042524 | 020122 | 052123 | |
| | 051101 | 044524 | 043516 | 051440 | | | | | |
| 000065 | 000 001 | 000046 | | | | | | | |
| | 042716 | 040524 | 027124 | 040504 | 020124 | 042522 | 047503 | 042122 | |
| | 024447 | 110766 | 000062 | 114576 | 072316 | 000401 | 052120 | 004467 | |
| | 051642 | 110760 | 110546 | | | | | | |
| 000066 | 000 001 | 000022 | | | | | | | |
| | 042762 | 073364 | 052114 | 110766 | 000063 | 073470 | 052116 | 073470 | |
| | 043022 | | | | | | | | |
| 000067 | 000 001 | 000050 | | | | | | | |
| | 043002 | 076306 | 000000 | 000000 | 103564 | 110766 | 000064 | 073570 | |
| | 043056 | 030450 | 020110 | 023454 | 047105 | 042524 | 020122 | 052517 | |
| | 050124 | 052125 | 020054 | 020061 | | | | | |
| 000070 | 000 001 | 000034 | | | | | | | |
| | 043050 | 051117 | 032440 | 024447 | 110766 | 000065 | 114576 | 072316 | |
| | 000401 | 052120 | 004467 | 051522 | 110760 | 110546 | | | |
| 000071 | 000 001 | 000022 | | | | | | | |
| | 043102 | 073364 | 052122 | 110766 | 000066 | 073470 | 052116 | 073470 | |
| | 043142 | | | | | | | | |
| 000072 | 000 001 | 000050 | | | | | | | |
| | 043122 | 076306 | 000000 | 000000 | 103564 | 110766 | 000067 | 073570 | |
| | 043172 | 030450 | 020110 | 023454 | 047105 | 042524 | 020122 | 052503 | |
| | 046114 | 043040 | 040514 | 023507 | | | | | |
| 000073 | 000 001 | 000003 | | | | | | | |
| | 043170 | 051 | | | | | | | |
| 000074 | 000 001 | 000026 | | | | | | | |
| | 043172 | 110766 | 000070 | 114576 | 072316 | 000401 | 052120 | 004467 | |
| | 051406 | 110760 | 110546 | | | | | | |
| 000075 | 000 001 | 000024 | | | | | | | |
| | 043216 | 073364 | 052132 | 110766 | 000071 | 051472 | 073364 | 052134 | |
| | 110766 | 000072 | | | | | | | |
| 000076 | 000 001 | 000024 | | | | | | | |
| | 043240 | 073470 | 051500 | 073470 | 043306 | 076306 | 000000 | 000000 | |
| | 073470 | 051536 | | | | | | | |
| 000077 | 000 001 | 000024 | | | | | | | |
| | 043262 | 073470 | 052100 | 073470 | 000002 | 104226 | 103564 | 110766 | |
| | 000073 | 073570 | | | | | | | |
| 000100 | 000 001 | 000050 | | | | | | | |

|        |        |        |        |        |        |        |        |        |
|--------|--------|--------|--------|--------|--------|--------|--------|--------|
|        | 043304 | 043336 | 030450 | 022110 | 023454 | 041101 | 051117 | 020124 |
|        | 046106 | 043501 | 036440 | 026047 | 044462 | 024464 | 110766 | 000074 |
|        | 073470 | 051500 | 073470 | 043404 |        |        |        |        |
| 000101 | 000 001 | 000030 |        |        |        |        |        |        |
|        | 043352 | 076306 | 000000 | 000000 | 073470 | 052134 | 073470 | 000001 |
|        | 104226 | 103564 | 110766 | 000075 |        |        |        |        |
| 000102 | 000 001 | 000050 |        |        |        |        |        |        |
|        | 043400 | 073570 | 043426 | 030450 | 022110 | 023454 | 046511 | 043501 |
|        | 020105 | 023443 | 044454 | 024465 | 110766 | 000076 | 114576 | 110676 |
|        | 000402 | 051520 | 052146 | 004467 |        |        |        |        |
| 000103 | 000 001 | 000022 |        |        |        |        |        |        |
|        | 043446 | 051150 | 110766 | 000077 | 052140 | 051502 | 073512 | 074024 |
|        | 073634 |        |        |        |        |        |        |        |
| 000104 | 000 001 | 000024 |        |        |        |        |        |        |
|        | 043466 | 043474 | 073570 | 043660 | 110766 | 000100 | 073470 | 051500 |
|        | 073470 | 043530 |        |        |        |        |        |        |
| 000105 | 000 001 | 000041 |        |        |        |        |        |        |
|        | 043510 | 076306 | 000000 | 000000 | 103564 | 110766 | 000101 | 073570 |
|        | 043550 | 023450 | 042440 | 052116 | 031440 | 041440 | 047117 | 023523 |
|        | 051    |        |        |        |        |        |        |        |
| 000106 | 000 001 | 000026 |        |        |        |        |        |        |
|        | 043550 | 110766 | 000102 | 114576 | 072316 | 000401 | 052120 | 004467 |
|        | 051030 | 110760 | 110546 |        |        |        |        |        |
| 000107 | 000 001 | 000026 |        |        |        |        |        |        |
|        | 043574 | 073364 | 051610 | 110766 | 000103 | 114576 | 072316 | 000401 |
|        | 052120 | 004467 | 051000 |        |        |        |        |        |
| 000110 | 000 001 | 000024 |        |        |        |        |        |        |
|        | 043620 | 110760 | 110546 | 073364 | 051576 | 110766 | 000104 | 114576 |
|        | 072316 | 000401 |        |        |        |        |        |        |
| 000111 | 000 001 | 000024 |        |        |        |        |        |        |
|        | 043642 | 052120 | 004467 | 050750 | 110760 | 110546 | 073364 | 051622 |
|        | 110766 | 000105 |        |        |        |        |        |        |
| 000112 | 000 001 | 000030 |        |        |        |        |        |        |
|        | 043664 | 110766 | 000106 | 114576 | 110676 | 000402 | 051672 | 052156 |
|        | 004467 | 050712 | 110766 | 000107 |        |        |        |        |
| 000113 | 000 001 | 000022 |        |        |        |        |        |        |
|        | 043712 | 052150 | 051472 | 073512 | 074024 | 073634 | 043732 | 073570 |
|        | 046672 |        |        |        |        |        |        |        |
| 000114 | 000 001 | 000026 |        |        |        |        |        |        |
|        | 043732 | 110766 | 000110 | 114576 | 072266 | 000403 | 036732 | 051456 |
|        | 051520 | 004467 | 050642 |        |        |        |        |        |
| 000115 | 000 001 | 000022 |        |        |        |        |        |        |
|        | 043756 | 110766 | 000111 | 114576 | 070630 | 000407 | 115074 | 115032 |
|        | 052160 |        |        |        |        |        |        |        |
| 000116 | 000 001 | 000026 |        |        |        |        |        |        |
|        | 043776 | 115034 | 051672 | 037052 | 052100 | 004467 | 050606 | 110766 |
|        | 000112 | 052072 | 051502 |        |        |        |        |        |
| 000117 | 000 001 | 000020 |        |        |        |        |        |        |
|        | 044022 | 073512 | 074024 | 073634 | 044040 | 051512 | 073364 | 052100 |
| 000120 | 000 001 | 000026 |        |        |        |        |        |        |
|        | 044040 | 110766 | 000113 | 051512 | 073364 | 051536 | 110766 | 000114 |
|        | 052072 | 051512 | 073512 |        |        |        |        |        |
| 000121 | 000 001 | 000022 |        |        |        |        |        |        |
|        | 044064 | 074044 | 073634 | 044076 | 073570 | 046640 | 110766 | 000115 |
|        | 051502 |        |        |        |        |        |        |        |
| 000122 | 000 001 | 000030 |        |        |        |        |        |        |
|        | 044104 | 074110 | 073410 | 044120 | 114576 | 070434 | 000402 | 000000 |
|        | 051520 | 004467 | 050474 | 000002 |        |        |        |        |
| 000123 | 000 001 | 000026 |        |        |        |        |        |        |
|        | 044132 | 110766 | 000116 | 052162 | 073364 | 052172 | 110766 | 000117 |
|        | 051512 | 073364 | 052174 |        |        |        |        |        |
| 000124 | 000 001 | 000026 |        |        |        |        |        |        |
|        | 044156 | 110766 | 000120 | 051764 | 073364 | 052176 | 110766 | 000121 |
|        | 051512 | 073364 | 052200 |        |        |        |        |        |
| 000125 | 000 001 | 000026 |        |        |        |        |        |        |
|        | 044202 | 110766 | 000122 | 051512 | 073364 | 052100 | 110766 | 000123 |
|        | 051472 | 073364 | 051632 |        |        |        |        |        |
| 000126 | 000 001 | 000026 |        |        |        |        |        |        |
|        | 044226 | 110766 | 000124 | 051512 | 073364 | 052100 | 110766 | 000125 |
|        | 114576 | 053254 | 000411 |        |        |        |        |        |
| 000127 | 000 001 | 000020 |        |        |        |        |        |        |
|        | 044252 | 115032 | 115034 | 115074 | 051576 | 051574 | 052176 | 052200 |
| 000130 | 000 001 | 000030 |        |        |        |        |        |        |
|        | 044270 | 050534 | 052100 | 004467 | 050320 | 110766 | 000126 | 051472 |
|        | 073364 | 051536 | 110766 | 000127 |        |        |        |        |
| 000131 | 000 001 | 000022 |        |        |        |        |        |        |
|        | 044316 | 052072 | 051512 | 073512 | 074044 | 073634 | 044336 | 073570 |
|        | 046640 |        |        |        |        |        |        |        |
| 000132 | 000 001 | 000026 |        |        |        |        |        |        |
|        | 044336 | 110766 | 000130 | 073470 | 051500 | 073470 | 044404 | 076306 |
|        | 000000 | 000000 | 073470 |        |        |        |        |        |
| 000133 | 000 001 | 000050 |        |        |        |        |        |        |
|        | 044362 | 052200 | 073470 | 000001 | 104226 | 103564 | 110766 | 000131 |
|        | 073570 | 044430 | 030450 | 022110 | 044454 | 026066 | 020047 | 047440 |
|        | 045102 | 041505 | 051524 | 024447 |        |        |        |        |
| 000134 | 000 001 | 000024 |        |        |        |        |        |        |
|        | 044430 | 110766 | 000132 | 051472 | 073364 | 051632 | 110766 | 000133 |
|        | 051472 | 051624 | 106342 |        |        |        |        |        |
| 000135 | 000 001 | 000024 |        |        |        |        |        |        |

|        |        |        |        |        |        |        |        |        |
|--------|--------|--------|--------|--------|--------|--------|--------|--------|
|        | 044454 | 050524 | 073430 | 073364 | 052210 | 110766 | 000134 | 051502 |
|        | 073364 | 051536 |        |        |        |        |        |        |
| 000136 | 000 001 | 000022 |        |        |        |        |        |        |
|        | 044476 | 110766 | 000135 | 052202 | 051512 | 073512 | 074024 | 073634 |
|        | 044522 |        |        |        |        |        |        |        |
| 000137 | 000 001 | 000022 |        |        |        |        |        |        |
|        | 044516 | 073570 | 046640 | 110766 | 000136 | 114576 | 052476 | 000410 |
|        | 115074 |        |        |        |        |        |        |        |
| 000140 | 000 001 | 000022 |        |        |        |        |        |        |
|        | 044536 | 115032 | 115034 | 052210 | 052172 | 037052 | 052174 | 052220 |
|        | 004467 |        |        |        |        |        |        |        |
| 000141 | 000 001 | 000026 |        |        |        |        |        |        |
|        | 044556 | 050040 | 110766 | 000137 | 051664 | 073364 | 051536 | 110766 |
|        | 000140 | 052212 | 051512 |        |        |        |        |        |
| 000142 | 000 001 | 000022 |        |        |        |        |        |        |
|        | 044602 | 073512 | 074044 | 073634 | 044616 | 073570 | 046640 | 110766 |
|        | 000141 |        |        |        |        |        |        |        |
| 000143 | 000 001 | 000024 |        |        |        |        |        |        |
|        | 044622 | 051502 | 051624 | 106342 | 050524 | 073430 | 073364 | 052222 |
|        | 110766 | 000142 |        |        |        |        |        |        |
| 000144 | 000 001 | 000022 |        |        |        |        |        |        |
|        | 044644 | 051600 | 051624 | 106342 | 050524 | 073430 | 051634 | 106334 |
|        | 050376 |        |        |        |        |        |        |        |
| 000145 | 000 001 | 000022 |        |        |        |        |        |        |
|        | 044664 | 073442 | 110766 | 000143 | 051634 | 106334 | 050376 | 073430 |
|        | 051512 |        |        |        |        |        |        |        |
| 000146 | 000 001 | 000022 |        |        |        |        |        |        |
|        | 044704 | 073512 | 074014 | 073634 | 044726 | 052224 | 051634 | 106334 |
|        | 050376 |        |        |        |        |        |        |        |
| 000147 | 000 001 | 000022 |        |        |        |        |        |        |
|        | 044724 | 073442 | 110766 | 000144 | 114576 | 054322 | 000414 | 115074 |
|        | 115032 |        |        |        |        |        |        |        |
| 000150 | 000 001 | 000024 |        |        |        |        |        |        |
|        | 044744 | 115034 | 037052 | 052172 | 052174 | 052210 | 051576 | 052222 |
|        | 050404 | 051560 |        |        |        |        |        |        |
| 000151 | 000 001 | 000030 |        |        |        |        |        |        |
|        | 044766 | 052100 | 004467 | 047624 | 110766 | 000145 | 051600 | 073364 |
|        | 051536 | 110766 | 000146 | 052072 |        |        |        |        |
| 000152 | 000 001 | 000020 |        |        |        |        |        |        |
|        | 045014 | 051512 | 073512 | 074044 | 073634 | 045032 | 073570 | 046622 |
| 000153 | 000 001 | 000022 |        |        |        |        |        |        |
|        | 045032 | 110766 | 000147 | 051472 | 106334 | 050376 | 073430 | 107206 |
|        | 052234 |        |        |        |        |        |        |        |
| 000154 | 000 001 | 000022 |        |        |        |        |        |        |
|        | 045052 | 106534 | 110546 | 051472 | 106334 | 050376 | 073442 | 110766 |
|        | 000150 |        |        |        |        |        |        |        |
| 000155 | 000 001 | 000022 |        |        |        |        |        |        |
|        | 045072 | 051634 | 106334 | 050376 | 073430 | 052246 | 107726 | 051634 |
|        | 106334 |        |        |        |        |        |        |        |
| 000156 | 000 001 | 000022 |        |        |        |        |        |        |
|        | 045112 | 050376 | 073442 | 110766 | 000151 | 051634 | 106334 | 050376 |
|        | 073430 |        |        |        |        |        |        |        |
| 000157 | 000 001 | 000020 |        |        |        |        |        |        |
|        | 045132 | 107206 | 052256 | 106534 | 051472 | 106334 | 050376 | 073430 |
| 000160 | 000 001 | 000020 |        |        |        |        |        |        |
|        | 045150 | 107206 | 107310 | 052270 | 110012 | 110546 | 051550 | 106334 |
| 000161 | 000 001 | 000026 |        |        |        |        |        |        |
|        | 045166 | 050376 | 073442 | 110766 | 000152 | 051634 | 073364 | 051536 |
|        | 110766 | 000153 | 051774 |        |        |        |        |        |
| 000162 | 000 001 | 000020 |        |        |        |        |        |        |
|        | 045212 | 106334 | 050376 | 073430 | 051600 | 073512 | 074016 | 073634 |
| 000163 | 000 001 | 000026 |        |        |        |        |        |        |
|        | 045230 | 045236 | 073570 | 046622 | 110766 | 000154 | 114576 | 057340 |
|        | 000406 | 050404 | 051560 |        |        |        |        |        |
| 000164 | 000 001 | 000026 |        |        |        |        |        |        |
|        | 045254 | 050442 | 051562 | 051610 | 052310 | 004467 | 047330 | 110766 |
|        | 000155 | 051724 | 073364 |        |        |        |        |        |
| 000165 | 000 001 | 000024 |        |        |        |        |        |        |
|        | 045300 | 051536 | 110766 | 000156 | 052302 | 051512 | 073512 | 074024 |
|        | 073634 | 045326 |        |        |        |        |        |        |
| 000166 | 000 001 | 000024 |        |        |        |        |        |        |
|        | 045322 | 073570 | 046622 | 110766 | 000157 | 052312 | 051472 | 106334 |
|        | 050252 | 074070 |        |        |        |        |        |        |
| 000167 | 000 001 | 000026 |        |        |        |        |        |        |
|        | 045344 | 110766 | 000160 | 052324 | 051502 | 106334 | 050252 | 074070 |
|        | 110766 | 000161 | 051664 |        |        |        |        |        |
| 000170 | 000 001 | 000030 |        |        |        |        |        |        |
|        | 045370 | 106334 | 050252 | 073650 | 045406 | 114576 | 073244 | 000403 |
|        | 000000 | 051606 | 052134 | 004467 |        |        |        |        |
| 000171 | 000 001 | 000026 |        |        |        |        |        |        |
|        | 045416 | 047200 | 110766 | 000162 | 114576 | 110676 | 000402 | 051510 |
|        | 052344 | 004467 | 047156 |        |        |        |        |        |
| 000172 | 000 001 | 000022 |        |        |        |        |        |        |
|        | 045442 | 110766 | 000163 | 052336 | 051472 | 073512 | 074024 | 073634 |
|        | 045466 |        |        |        |        |        |        |        |
| 000173 | 000 001 | 000024 |        |        |        |        |        |        |
|        | 045462 | 073570 | 045672 | 110766 | 000164 | 052346 | 106334 | 050260 |
|        | 073650 | 045512 |        |        |        |        |        |        |

| | | | | | | | |
|---|---|---|---|---|---|---|---|
| 000174 | 000 001 | 000030 | | | | | |
| | 045504 | 114576 | 070612 | 000401 | 000000 | 004467 | 047100 | 110762 |
| | 073364 | 052356 | 110766 | 000165 | | | | |
| 000175 | 000 001 | 000024 | | | | | |
| | 045532 | 073470 | 052122 | 073470 | 045640 | 076306 | 000000 | 000000 |
| | 073470 | 052134 | | | | | | |
| 000176 | 000 001 | 000022 | | | | | |
| | 045554 | 073470 | 052114 | 073470 | 000002 | 104226 | 073470 | 050252 |
| | 073470 | | | | | | | |
| 000177 | 000 001 | 000022 | | | | | |
| | 045574 | 050376 | 073470 | 000002 | 104214 | 073470 | 052310 | 073470 |
| | 051576 | | | | | | | |
| 000200 | 000 001 | 000024 | | | | | |
| | 045614 | 073470 | 052356 | 073470 | 000003 | 104226 | 103564 | 110766 |
| | 000166 | 073570 | | | | | | |
| 000201 | 000 001 | 000035 | | | | | |
| | 045636 | 045672 | 030450 | 020110 | 031054 | 033111 | 031054 | 026130 |
| | 040466 | 026061 | 031061 | 032511 | 031454 | 032111 | 051 | |
| 000202 | 000 001 | 000026 | | | | | |
| | 045672 | 110766 | 000167 | 110766 | 000170 | 051472 | 073364 | 052366 |
| | 110766 | 000171 | 052360 | | | | | |
| 000203 | 000 001 | 000020 | | | | | |
| | 045716 | 106334 | 050376 | 073430 | 107206 | 052360 | 106334 | 050302 |
| 000204 | 000 001 | 000024 | | | | | |
| | 045734 | 073440 | 073654 | 051500 | 052366 | 051560 | 045710 | 110766 |
| | 000172 | 052302 | | | | | | |
| 000205 | 000 001 | 000022 | | | | | |
| | 045756 | 107206 | 052370 | 106334 | 050302 | 073440 | 110766 | 000173 |
| | 052400 | | | | | | | |
| 000206 | 000 001 | 000022 | | | | | |
| | 045776 | 106334 | 050274 | 073650 | 046020 | 114576 | 071426 | 000403 |
| | 051732 | | | | | | | |
| 000207 | 000 001 | 000026 | | | | | |
| | 046016 | 115042 | 000000 | 004467 | 046572 | 110766 | 000174 | 051472 |
| | 052302 | 106342 | 051006 | | | | | |
| 000210 | 000 001 | 000020 | | | | | |
| | 046042 | 073424 | 051472 | 106334 | 050376 | 073430 | 107206 | 110012 |
| 000211 | 000 001 | 000024 | | | | | |
| | 046060 | 051472 | 052302 | 106342 | 051006 | 073440 | 110766 | 000175 |
| | 051502 | 052302 | | | | | | |
| 000212 | 000 001 | 000020 | | | | | |
| | 046102 | 106342 | 051006 | 073424 | 051634 | 106334 | 050376 | 073430 |
| 000213 | 000 001 | 000020 | | | | | |
| | 046120 | 107206 | 110012 | 051502 | 052302 | 106342 | 051006 | 073440 |
| 000214 | 000 001 | 000024 | | | | | |
| | 046136 | 110766 | 000176 | 051664 | 052302 | 106342 | 051006 | 073424 |
| | 051550 | 106334 | | | | | | |
| 000215 | 000 001 | 000022 | | | | | |
| | 046160 | 050376 | 073430 | 107206 | 110012 | 051664 | 052302 | 106342 |
| | 051006 | | | | | | | |
| 000216 | 000 001 | 000022 | | | | | |
| | 046200 | 073440 | 110766 | 000177 | 052302 | 106334 | 050310 | 073430 |
| | 051472 | | | | | | | |
| 000217 | 000 001 | 000024 | | | | | |
| | 046220 | 073474 | 052302 | 106334 | 050310 | 073442 | 110766 | 000200 |
| | 052302 | 052124 | | | | | | |
| 000220 | 000 001 | 000022 | | | | | |
| | 046242 | 073512 | 074044 | 073634 | 046256 | 073570 | 046432 | 110766 |
| | 000201 | | | | | | | |
| 000221 | 000 001 | 000030 | | | | | |
| | 046262 | 114576 | 110676 | 000402 | 051500 | 052416 | 004467 | 046320 |
| | 110766 | 000202 | 052410 | 051472 | | | | |
| 000222 | 000 001 | 000022 | | | | | |
| | 046310 | 073512 | 074024 | 073634 | 046324 | 073570 | 046432 | 110766 |
| | 000203 | | | | | | | |
| 000223 | 000 001 | 000022 | | | | | |
| | 046330 | 114576 | 071504 | 000403 | 051524 | 115030 | 115030 | 004467 |
| | 046250 | | | | | | | |
| 000224 | 000 001 | 000026 | | | | | |
| | 046350 | 110766 | 000204 | 114576 | 072120 | 000403 | 051524 | 052434 |
| | 052444 | 004467 | 046224 | | | | | |
| 000225 | 000 001 | 000024 | | | | | |
| | 046374 | 110766 | 000205 | 052420 | 051512 | 073512 | 074016 | 052436 |
| | 051326 | 073512 | | | | | | |
| 000226 | 000 001 | 000022 | | | | | |
| | 046416 | 074044 | 074010 | 073634 | 046432 | 073570 | 046672 | 110766 |
| | 000206 | | | | | | | |
| 000227 | 000 001 | 000026 | | | | | |
| | 046436 | 110766 | 000207 | 073470 | 051452 | 073470 | 052114 | 102614 |
| | 000000 | 000000 | 073470 | | | | | |
| 000230 | 000 001 | 000026 | | | | | |
| | 046462 | 050274 | 073470 | 000001 | 104214 | 103564 | 110766 | 000210 |
| | 051512 | 051472 | 051624 | | | | | |
| 000231 | 000 001 | 000022 | | | | | |
| | 046506 | 106342 | 050524 | 073442 | 110766 | 000211 | 073470 | 051500 |

| | | | | | | | |
|---|---|---|---|---|---|---|---|
| 000232 | 073470 000 001 000026 046526 | 046562 | 076306 | 000000 | 000000 | 073470 | 051632 073470 |
| 000233 | 000001 104226 000 001 000033 046552 | 103564 110766 | 000212 | 073570 | 046604 | 030450 | 022110 023454 |
| 000234 | 042503 046114 000 001 000024 046604 | 021440 110766 | 026047 000213 | 033111 052106 | 051 051472 | 073474 | 073364 052114 |
| 000235 | 110766 000214 000 001 000026 046626 | 073654 | 051500 | 051632 | 052200 | 044442 | 110766 000215 |
| 000236 | 051512 051472 000 001 000022 046652 | 051624 106342 | 050524 | 073442 | 073654 | 051500 | 052134 052136 |
| 000237 | 043234 000 001 000030 046672 | 110766 | 000216 | 110766 | 000217 | 073470 | 052116 073470 |
| 000240 | 047006 076306 000 001 000022 046720 | 000000 073470 | 000000 052134 | 073470 | 052114 | 073470 | 000002 104226 |
| 000241 | 051472 000 001 000022 046740 | 073364 | 052042 | 052034 | 106334 | 050310 | 110762 073470 |
| 000242 | 000001 000 001 000024 046760 | 104226 | 073654 | 051500 | 052042 | 052044 | 046744 103564 |
| 000243 | 110766 000220 000 001 000034 047002 | 073570 | 047020 | 030450 | 020110 | 030454 | 044466 024465 |
| 000244 | 110766 000221 000 001 000026 047034 | 076306 | 073470 000000 | 052122 000000 | 073470 073470 | 047006 052134 | 073470 052114 |
| 000245 | 073470 000002 000 001 000024 047060 | 104226 051472 | 073364 | 052042 | 052034 | 106334 | 050310 110762 |
| 000246 | 073470 000001 000 001 000024 047102 | 104226 | 073654 | 051500 | 052042 | 052044 | 047066 103564 |
| 000247 | 110766 000222 000 001 000024 047124 | 052106 | 051472 | 073516 | 107206 | 073404 | 052454 110766 |
| 000250 | 000223 051472 000 001 000024 047146 | 073364 | 052042 | 110766 | 000224 | 052034 | 106334 050310 |
| 000251 | 073430 051512 000 001 000022 047170 | 073512 | 074024 | 073634 | 047204 | 073570 | 047262 110766 |
| 000252 | 000225 000 001 000024 047210 | 051472 | 073364 | 051632 | 110766 | 000226 | 051624 052034 |
| 000253 | 106342 051006 000 001 000020 047232 | 073424 | 052034 | 106334 | 050310 | 073430 | 107206 107310 |
| 000254 | 000 001 000024 047250 | 051624 | 052034 | 106342 | 051006 | 073440 | 110766 000227 |
| 000255 | 073654 051500 000 001 000026 047272 | 051632 | 051672 | 047216 | 073654 | 051500 | 052042 052044 |
| 000256 | 047152 110766 000 001 000024 047316 | 000230 051472 | 073364 | 051632 | 110766 | 000231 | 051624 106334 |
| 000257 | 050310 073430 000 001 000020 047340 | 051512 | 073512 | 074024 | 073634 | 047356 | 073570 047422 |
| 000260 | 000 001 000022 047356 | 110766 | 000232 | 051624 | 106334 | 050310 | 073430 107206 |
| 000261 | 052256 000 001 000020 047376 | 106534 | 052446 | 107310 | 052270 | 110012 | 110546 051624 |
| 000262 | 000 001 000024 047414 | 106334 | 050310 | 073442 | 110766 | 000233 | 073654 051500 |
| 000263 | 051632 052044 000 001 000026 047436 | 047324 | 110766 | 000234 | 052106 | 051472 | 073516 073364 |
| 000264 | 052114 110766 000 001 000024 047462 | 000235 073470 | 052122 | 073470 | 047524 | 076306 | 000000 000000 |
| 000265 | 073470 052114 000 001 000050 047504 047556 051514 041440 | 073470 030450 052517 052116 | 000001 030510 | 104226 044454 | 103564 026065 | 110766 020047 | 000236 073570 041440 046105 |
| 000266 | 000 001 000032 047552 047612 076306 | 042105 000000 | 024447 000000 | 110766 103564 | 000237 | 073470 | 052122 073470 |
| 000267 | 000 001 000050 047602 046103 | 110766 051501 | 000240 020123 | 073570 022440 | 047704 020040 | 030450 020040 | 020110 023454 042040 051505 |

|        |        |        |        |        |        |        |        |
|--------|--------|--------|--------|--------|--------|--------|--------|
|        | 051103 | 050111 | 044524 | 047117 |        |        |        |
| 000270 | 000 001 | 000035 |        |        |        |        |        |
|        | 047650 | 026047 | 033463 | 026130 | 026047 | 051440 | 055111 | 020105 |
|        | 020040 | 041515 | 020110 | 046440 | 044103 | 023503 | 051    |        |
| 000271 | 000 001 | 000026 |        |        |        |        |        |
|        | 047704 | 110766 | 000241 | 051472 | 073364 | 051632 | 110766 | 000242 |
|        | 051624 | 106334 | 050310 |        |        |        |        |        |
| 000272 | 000 001 | 000020 |        |        |        |        |        |
|        | 047730 | 073430 | 051512 | 073512 | 074024 | 073634 | 047750 | 073570 |
| 000273 | 000 001 | 000026 |        |        |        |        |        |
|        | 047746 | 050220 | 110766 | 000243 | 051472 | 073364 | 052042 | 110766 |
|        | 000244 | 052034 | 051624 |        |        |        |        |        |
| 000274 | 000 001 | 000020 |        |        |        |        |        |
|        | 047772 | 106342 | 051006 | 073424 | 052270 | 110012 | 110546 | 052034 |
| 000275 | 000 001 | 000022 |        |        |        |        |        |
|        | 050010 | 106334 | 050470 | 073442 | 073654 | 051500 | 052042 | 051672 |
|        | 047762 |        |        |        |        |        |        |
| 000276 | 000 001 | 000026 |        |        |        |        |        |
|        | 050030 | 110766 | 000245 | 073470 | 052122 | 073470 | 050164 | 076306 |
|        | 000000 | 000000 | 073470 |        |        |        |        |
| 000277 | 000 001 | 000022 |        |        |        |        |        |
|        | 050054 | 051632 | 073470 | 000001 | 104226 | 051624 | 106334 | 050310 |
|        | 110762 |        |        |        |        |        |        |
| 000300 | 000 001 | 000024 |        |        |        |        |        |
|        | 050074 | 073470 | 000001 | 104226 | 051472 | 073364 | 052466 | 052460 |
|        | 051624 | 106342 |        |        |        |        |        |
| 000301 | 000 001 | 000024 |        |        |        |        |        |
|        | 050116 | 051316 | 110762 | 073470 | 000001 | 104242 | 073654 | 051500 |
|        | 052466 | 051556 |        |        |        |        |        |
| 000302 | 000 001 | 000024 |        |        |        |        |        |
|        | 050140 | 050110 | 073470 | 050470 | 073470 | 000001 | 104214 | 103564 |
|        | 110766 | 000246 |        |        |        |        |        |
| 000303 | 000 001 | 000050 |        |        |        |        |        |
|        | 050162 | 073570 | 050220 | 030450 | 020110 | 044454 | 026064 | 032111 |
|        | 031054 | 026130 | 031061 | 032101 | 031454 | 026130 | 044463 | 024466 |
|        | 110766 | 000247 | 073654 | 051500 |        |        |        |
| 000304 | 000 001 | 000032 |        |        |        |        |        |
|        | 050230 | 051632 | 052044 | 047716 | 110766 | 000250 | 113042 | 116746 |
|        | 044570 | 000134 | 115042 | 040001 | 000006 |        |        |
| 000305 | 000 001 | 000040 |        |        |        |        |        |
|        | 050260 | 115074 | 040001 | 042020 | 037050 | 040001 | 000002 | 036732 |
|        | 050002 | 000047 | 036732 | 054004 | 000022 | 050316 | 050002 | 000020 |
| 000306 | 000 001 | 000010 |        |        |        |        |        |
|        | 050376 | 050404 | 050002 | 000014 |        |        |        |
| 000307 | 000 001 | 000010 |        |        |        |        |        |
|        | 050434 | 050442 | 050002 | 000013 |        |        |        |
| 000310 | 000 001 | 000010 |        |        |        |        |        |
|        | 050470 | 050476 | 050002 | 000003 |        |        |        |
| 000311 | 000 001 | 000010 |        |        |        |        |        |
|        | 050504 | 050512 | 050002 | 000005 |        |        |        |
| 000312 | 000 001 | 000012 |        |        |        |        |        |
|        | 050524 | 050534 | 110002 | 000004 | 000024 |        |        |
| 000313 | 000 001 | 000012 |        |        |        |        |        |
|        | 051006 | 051016 | 114004 | 000003 | 000020 |        |        |
| 000314 | 000 001 | 000050 |        |        |        |        |        |
|        | 051316 | 040202 | 114004 | 000014 | 000020 | 016746 | 043476 | 000134 |
|        | 016746 | 043472 | 000134 | 016746 | 043466 | 000134 | 016746 | 043462 |
|        | 000134 | 020040 | 020040 | 000000 |        |        |        |
| 000315 | 000 001 | 000050 |        |        |        |        |        |
|        | 051364 | 020040 | 020040 | 000000 | 020040 | 020040 | 000000 | 020040 |
|        | 020040 | 000000 | 020040 | 020040 | 000000 | 020040 | 020040 | 000000 |
|        | 020040 | 020040 | 000000 | 020040 |        |        |        |
| 000316 | 000 001 | 000050 |        |        |        |        |        |
|        | 051432 | 020040 | 000000 | 020040 | 020040 | 000000 | 012746 | 000007 |
|        | 000134 | 000007 | 002260 | 000047 | 000000 | 012746 | 000013 | 000134 |
|        | 000013 | 012746 | 000001 | 000134 |        |        |        |
| 000317 | 000 001 | 000050 |        |        |        |        |        |
|        | 051500 | 000001 | 012746 | 000002 | 000134 | 000002 | 012746 | 000000 |
|        | 000134 | 000000 | 000000 | 000000 | 012746 | 000204 | 000134 | 000204 |
|        | 000000 | 012746 | 000022 | 000134 |        |        |        |
| 000320 | 000 001 | 000050 |        |        |        |        |        |
|        | 051546 | 000022 | 012746 | 000014 | 000134 | 000014 | 000000 | 000000 |
|        | 012746 | 000144 | 000134 | 000144 | 000000 | 000000 | 012746 | 000004 |
|        | 000134 | 000004 | 000000 | 012746 |        |        |        |
| 000321 | 000 001 | 000050 |        |        |        |        |        |
|        | 051614 | 000026 | 000134 | 000026 | 000000 | 016746 | 000002 | 000134 |
|        | 000000 | 012746 | 000005 | 000134 | 000005 | 012746 | 000031 | 000134 |
|        | 000031 | 012746 | 000240 | 000134 |        |        |        |
| 000322 | 000 001 | 000050 |        |        |        |        |        |
|        | 051662 | 000240 | 012746 | 000003 | 000134 | 000003 | 012746 | 000023 |
|        | 000134 | 000023 | 012746 | 000043 | 000134 | 000043 | 012746 | 000036 |
|        | 000134 | 000036 | 012746 | 000006 |        |        |        |
| 000323 | 000 001 | 000050 |        |        |        |        |        |
|        | 051730 | 000006 | 000134 | 000006 | 012746 | 000310 | 000134 | 000310 | 012746 |
|        | 000074 | 000134 | 000074 | 012746 | 000010 | 000134 | 000010 | 012746 |
|        | 000024 | 000134 | 000024 | 012746 |        |        |        |
| 000324 | 000 001 | 000050 |        |        |        |        |        |
|        | 051776 | 000011 | 000134 | 000011 | 012746 | 000054 | 000134 | 000054 |
|        | 012746 | 000012 | 000134 | 000012 | 012746 | 000123 | 000134 | 000123 |

|        |            |        |        |        |        |        |        |        |
|--------|------------|--------|--------|--------|--------|--------|--------|--------|
|        | 016746     | 000002 | 000134 | 000000 |        |        |        |        |
| 000325 | 000 001    | 000050 |        |        |        |        |        |        |
|        | 052044     | 000020 | 012700 | 052060 | 000545 | 000000 | 000000 | 052123 |
|        | 052101     | 042056 | 052101 | 000000 | 016746 | 000002 | 000134 | 000000 |
|        | 045504     | 000000 | 016746 | 000002 |        |        |        |        |
| 000326 | 000 001    | 000050 |        |        |        |        |        |        |
|        | 052112     | 000134 | 000000 | 000000 | 000000 | 000000 | 016746 | 000002 |
|        | 000134     | 000000 | 000000 | 001440 | 016746 | 000002 | 000134 | 000000 |
|        | 016746     | 000002 | 000134 | 000000 |        |        |        |        |
| 000327 | 000 001    | 000050 |        |        |        |        |        |        |
|        | 052160     | 000132 | 012746 | 001130 | 000134 | 001130 | 000000 | 000000 |
|        | 000000     | 000000 | 016746 | 000002 | 000134 | 000000 | 016746 | 000002 |
|        | 000134     | 000000 | 000000 | 012746 |        |        |        |        |
| 000330 | 000 001    | 000050 |        |        |        |        |        |        |
|        | 052226     | 077775 | 000134 | 077775 | 012700 | 052246 | 000472 | 037144 |
|        | 173546     | 012746 | 001212 | 000134 | 001212 | 012700 | 052270 | 000461 |
|        | 041710     | 000000 | 012700 | 052302 |        |        |        |        |
| 000331 | 000 001    | 000050 |        |        |        |        |        |        |
|        | 052274     | 000454 | 040000 | 000000 | 016746 | 000002 | 000134 | 000000 |
|        | 012746     | 020122 | 000134 | 020122 | 000000 | 012746 | 020105 | 000134 |
|        | 020105     | 000000 | 016746 | 000002 |        |        |        |        |
| 000332 | 000 001    | 000050 |        |        |        |        |        |        |
|        | 052342     | 000134 | 000000 | 012746 | 042020 | 000134 | 042020 | 000000 |
|        | 016746     | 000002 | 000134 | 000000 | 012746 | 000021 | 000134 | 000021 |
|        | 012746     | 000045 | 000134 | 000045 |        |        |        |        |
| 000333 | 000 001    | 000050 |        |        |        |        |        |        |
|        | 052410     | 016746 | 000002 | 000134 | 000000 | 016746 | 000010 | 000134 |
|        | 014046     | 014046 | 000134 | 000000 | 016746 | 000002 | 000134 | 000000 |
|        | 012700     | 052460 | 000406 | 000000 |        |        |        |        |
| 000334 | 000 001    | 000022 |        |        |        |        |        |        |
|        | 052456     | 000000 | 016746 | 000002 | 000134 | 000000 | 014046 | 014046 |
|        | 000134     |        |        |        |        |        |        |        |
| 000335 | 000 001    | 000050 |        |        |        |        |        |        |
|        | 052476     | 004567 | 020566 | 000410 | 012502 | 013500 | 010067 | 000066 |
|        | 010067     | 000214 | 010067 | 000252 | 005300 | 010067 | 000170 | 010067 |
|        | 000226     | 010067 | 000272 | 005200 |        |        |        |        |
| 000336 | 000 001    | 000050 |        |        |        |        |        |        |
|        | 052544     | 005200 | 010067 | 000172 | 010067 | 000230 | 013501 | 005301 |
|        | 010167     | 000254 | 013503 | 005303 | 060302 | 010367 | 124504 | 012767 |
|        | 000000     | 124472 | 016700 | 124470 |        |        |        |        |
| 000337 | 000 001    | 000050 |        |        |        |        |        |        |
|        | 052612     | 016701 | 124466 | 013567 | 000274 | 012503 | 012567 | 000342 |
|        | 005067     | 000244 | 012567 | 000324 | 005067 | 000316 | 012737 | 000420 |
|        | 053136     | 012737 | 000426 | 053054 |        |        |        |        |
| 000340 | 000 001    | 000050 |        |        |        |        |        |        |
|        | 052660     | 005004 | 010267 | 000216 | 012767 | 000010 | 000252 | 000403 |
|        | 012767     | 000007 | 000242 | 116417 | 053224 | 000777 | 116417 | 053234 |
|        | 000777     | 162702 | 000000 | 005200 |        |        |        |        |
| 000341 | 000 001    | 000050 |        |        |        |        |        |        |
|        | 052726     | 005301 | 000434 | 162702 | 000000 | 005301 | 000430 | 162702 |
|        | 000000     | 005300 | 005301 | 000423 | 005302 | 005300 | 000420 | 062702 |
|        | 000000     | 005300 | 005201 | 000413 |        |        |        |        |
| 000342 | 000 001    | 000050 |        |        |        |        |        |        |
|        | 052774     | 062702 | 000000 | 005201 | 000407 | 062702 | 000000 | 005200 |
|        | 005201     | 000402 | 005202 | 005200 | 005700 | 002444 | 005701 | 002442 |
|        | 022700     | 000000 | 002437 | 022701 |        |        |        |        |
| 000343 | 000 001    | 000050 |        |        |        |        |        |        |
|        | 053042     | 000000 | 002434 | 132712 | 000100 | 001431 | 005204 | 042704 |
|        | 177770     | 110423 | 005304 | 042704 | 177770 | 152712 | 000200 | 005227 |
|        | 000000     | 020227 | 000000 | 001424 |        |        |        |        |
| 000344 | 000 001    | 000050 |        |        |        |        |        |        |
|        | 053110     | 116404 | 053244 | 005327 | 000000 | 001266 | 052767 | 000001 |
|        | 000032     | 000413 | 005204 | 000401 | 005204 | 042704 | 177770 | 005327 |
|        | 000000     | 001260 | 052767 | 000002 |        |        |        |        |
| 000345 | 000 001    | 000050 |        |        |        |        |        |        |
|        | 053156     | 000002 | 012737 | 000000 | 000000 | 016737 | 177706 | 000000 |
|        | 000167     | 020124 | 012767 | 005204 | 177730 | 012767 | 005204 | 177640 |
|        | 012767     | 000007 | 177724 | 000745 |        |        |        |        |
| 000346 | 000 001    | 000032 |        |        |        |        |        |        |
|        | 053224     | 004003 | 010414 | 014424 | 021035 | 007005 | 013016 | 017426 |
|        | 002437     | 003405 | 000407 | 001401 | 002403 |        |        |        |
| 000347 | 000 001    | 000050 |        |        |        |        |        |        |
|        | 053254     | 004567 | 020010 | 000411 | 012746 | 000102 | 104041 | 012467 |
|        | 000374     | 013500 | 010067 | 001002 | 010067 | 000464 | 005400 | 010067 |
|        | 000774     | 005300 | 010067 | 000254 |        |        |        |        |
| 000350 | 000 001    | 000050 |        |        |        |        |        |        |
|        | 053322     | 005200 | 005200 | 010067 | 000232 | 005300 | 005400 | 005300 |
|        | 010067     | 000244 | 010067 | 000262 | 013501 | 005301 | 010167 | 000240 |
|        | 012767     | 000001 | 000552 | 005000 |        |        |        |        |
| 000351 | 000 001    | 000050 |        |        |        |        |        |        |
|        | 053370     | 005001 | 012502 | 010267 | 000120 | 005367 | 000114 | 010267 |
|        | 000616     | 005067 | 000704 | 013567 | 000070 | 016767 | 000064 | 000212 |
|        | 016767     | 000056 | 000302 | 013567 |        |        |        |        |
| 000352 | 000 001    | 000050 |        |        |        |        |        |        |
|        | 053436     | 000416 | 013567 | 000070 | 011567 | 000446 | 005035 | 012567 |
|        | 000410     | 012567 | 000566 | 012767 | 000001 | 000174 | 005067 | 000250 |
|        | 005067     | 000154 | 005046 | 010667 |        |        |        |        |
| 000353 | 000 001    | 000050 |        |        |        |        |        |        |

|        |        |        |        |        |        |        |        |        |
|--------|--------|--------|--------|--------|--------|--------|--------|--------|
|        | 053504 | 000324 | 122712 | 000000 | 003077 | 010204 | 162704 | 000000 |
|        | 010467 | 000344 | 152712 | 000200 | 005327 | 000000 | 001002 | 000167 |
|        | 000526 | 012746 | 000010 | 012704 |        |        |        |        |
| 000354 | 000 001 | 000050 |       |        |        |        |        |        |
|        | 053552 | 000003 | 116417 | 054300 | 000777 | 062702 | 000000 | 005200 |
|        | 005301 | 000420 | 062702 | 000000 | 005301 | 005300 | 000413 | 062702 |
|        | 000000 | 005300 | 005201 | 022701 |        |        |        |        |
| 000355 | 000 001 | 000050 |       |        |        |        |        |        |
|        | 053620 | 000000 | 000404 | 005202 | 005200 | 022700 | 000000 | 002427 |
|        | 122712 | 000000 | 003030 | 111205 | 166705 | 177766 | 060527 | 000000 |
|        | 152712 | 000200 | 005227 | 000000 |        |        |        |        |
| 000356 | 000 001 | 000050 |       |        |        |        |        |        |
|        | 053666 | 022706 | 000000 | 001574 | 006303 | 006303 | 050403 | 005316 |
|        | 001321 | 010316 | 000715 | 000521 | 156467 | 054314 | 000376 | 000407 |
|        | 111205 | 100005 | 042705 | 000300 |        |        |        |        |
| 000357 | 000 001 | 000050 |       |        |        |        |        |        |
|        | 053734 | 122705 | 000000 | 003411 | 005227 | 000000 | 010205 | 006304 |
|        | 066405 | 054304 | 006204 | 152715 | 000100 | 005304 | 100272 | 062702 |
|        | 000000 | 005201 | 010304 | 006203 |        |        |        |        |
| 000360 | 000 001 | 000050 |       |        |        |        |        |        |
|        | 054002 | 006203 | 042704 | 177774 | 005216 | 022716 | 000011 | 001004 |
|        | 005726 | 011603 | 005016 | 000763 | 022706 | 000000 | 001401 | 000752 |
|        | 005767 | 000254 | 001403 | 005067 |        |        |        |        |
| 000361 | 000 001 | 000050 |       |        |        |        |        |        |
|        | 054050 | 000246 | 000422 | 022767 | 000000 | 177402 | 003016 | 012705 |
|        | 000000 | 012725 | 000000 | 016725 | 177564 | 016725 | 177640 | 016725 |
|        | 177544 | 010567 | 177752 | 005237 |        |        |        |        |
| 000362 | 000 001 | 000050 |       |        |        |        |        |        |
|        | 054116 | 000000 | 012767 | 000001 | 177536 | 005067 | 177612 | 005067 |
|        | 177516 | 005227 | 000000 | 042767 | 000300 | 177770 | 001002 | 005267 |
|        | 177762 | 005202 | 026700 | 177446 |        |        |        |        |
| 000363 | 000 001 | 000050 |       |        |        |        |        |        |
|        | 054164 | 003403 | 005200 | 000167 | 177312 | 005000 | 026701 | 177416 |
|        | 003403 | 005201 | 000167 | 177274 | 112704 | 000200 | 016700 | 177366 |
|        | 010003 | 012702 | 000000 | 140422 |        |        |        |        |
| 000364 | 000 001 | 000050 |       |        |        |        |        |        |
|        | 054232 | 005300 | 100375 | 010300 | 005301 | 100372 | 005005 | 010537 |
|        | 000000 | 016706 | 177554 | 005726 | 000167 | 017040 | 012705 | 000001 |
|        | 000766 | 012705 | 000002 | 000763 |        |        |        |        |
| 000365 | 000 001 | 000024 |       |        |        |        |        |        |
|        | 054300 | 002400 | 010412 | 000000 | 000001 | 000000 | 177777 | 001004 |
|        | 000410 | 000000 |        |       |        |        |        |        |
| 000366 | 000 001 | 000046 |       |        |        |        |        |        |
|        | 054322 | 004467 | 034422 | 106176 | 000000 | 000000 | 070514 | 140200 |
|        | 110766 | 000002 | 073574 | 056636 | 000024 | 000026 | 177777 | 177777 |
|        | 110766 | 000003 | 073574 |        |        |        |        |        |
| 000367 | 000 001 | 000046 |       |        |        |        |        |        |
|        | 054366 | 056576 | 000002 | 000004 | 000006 | 177777 | 110766 | 000003 |
|        | 073574 | 056622 | 000010 | 000012 | 177777 | 177777 | 110766 | 000004 |
|        | 056664 | 114632 | 000030 |       |        |        |        |        |
| 000370 | 000 001 | 000022 |       |        |        |        |        |        |
|        | 054432 | 073442 | 110766 | 000005 | 056606 | 056614 | 106474 | 073364 |
|        | 056674 |        |        |       |        |        |        |        |
| 000371 | 000 001 | 000024 |       |        |        |        |        |        |
|        | 054452 | 110766 | 000006 | 114632 | 000016 | 073430 | 056676 | 073516 |
|        | 056606 | 107726 |        |       |        |        |        |        |
| 000372 | 000 001 | 000024 |       |        |        |        |        |        |
|        | 054474 | 056676 | 073474 | 073364 | 056714 | 110766 | 000007 | 114632 |
|        | 000016 | 073430 |        |       |        |        |        |        |
| 000373 | 000 001 | 000022 |       |        |        |        |        |        |
|        | 054516 | 056706 | 056676 | 073516 | 056606 | 106474 | 073516 | 073364 |
|        | 056724 |        |        |       |        |        |        |        |
| 000374 | 000 001 | 000030 |       |        |        |        |        |        |
|        | 054536 | 110766 | 000010 | 114642 | 000002 | 054572 | 114642 | 000010 |
|        | 054576 | 114642 | 000014 | 054600 |        |        |        |        |
| 000375 | 000 001 | 000034 |       |        |        |        |        |        |
|        | 054564 | 114576 | 061620 | 000416 | 000000 | 056674 | 000000 | 000000 |
|        | 056734 | 056744 | 056754 | 056764 | 056766 | 056770 |        |        |
| 000376 | 000 001 | 000030 |       |        |        |        |        |        |
|        | 054616 | 057000 | 056724 | 056714 | 057010 | 004467 | 037766 | 110766 |
|        | 000011 | 114642 | 000010 | 054660 |        |        |        |        |
| 000377 | 000 001 | 000034 |       |        |        |        |        |        |
|        | 054644 | 114642 | 000014 | 054662 | 114576 | 063720 | 000405 | 000000 |
|        | 000000 | 056644 | 057022 | 057024 | 004467 | 037722 |        |        |
| 000400 | 000 001 | 000034 |       |        |        |        |        |        |
|        | 054676 | 110766 | 000012 | 114642 | 000010 | 054724 | 114642 | 000014 |
|        | 054726 | 114576 | 065510 | 000404 | 000000 | 000000 |        |        |
| 000401 | 000 001 | 000026 |       |        |        |        |        |        |
|        | 054730 | 057034 | 057036 | 004467 | 037660 | 110766 | 000013 | 054664 |
|        | 057040 | 106334 | 056636 |       |        |        |        |        |
| 000402 | 000 001 | 000022 |       |        |        |        |        |        |
|        | 054754 | 073442 | 110766 | 000014 | 056664 | 057050 | 106334 | 056636 |
|        | 073442 |        |        |       |        |        |        |        |
| 000403 | 000 001 | 000026 |       |        |        |        |        |        |
|        | 054774 | 110766 | 000015 | 114576 | 107142 | 000401 | 056770 | 004467 |
|        | 037604 | 110762 | 056676 |       |        |        |        |        |
| 000404 | 000 001 | 000022 |       |        |        |        |        |        |
|        | 055020 | 106334 | 056636 | 073442 | 110766 | 000016 | 057040 | 107206 |

| | | | | | | | | |
|---|---|---|---|---|---|---|---|---|
| | | 057002 | | | | | | |
| 000405 | 000 001 | 000030 | | | | | | |
| | 055040 | 106534 | 073410 | 055054 | 114576 | 107764 | 000401 | 000000 |
| | 004467 | 037542 | 000004 | 110760 | | | | |
| 000406 | 000 001 | 000024 | | | | | | |
| | 055066 | 110546 | 057060 | 106334 | 056636 | 073442 | 110766 | 000017 |
| | 057026 | 057070 | | | | | | |
| 000407 | 000 001 | 000024 | | | | | | |
| | 055110 | 106334 | 056636 | 073442 | 110766 | 000020 | 057014 | 057100 |
| | 106334 | 056636 | | | | | | |
| 000410 | 000 001 | 000022 | | | | | | |
| | 055132 | 073442 | 110766 | 000021 | 056772 | 057110 | 106334 | 056636 |
| | 073442 | | | | | | | |
| 000411 | 000 001 | 000022 | | | | | | |
| | 055152 | 110766 | 000022 | 056676 | 106334 | 056636 | 073430 | 056630 |
| | 073516 | | | | | | | |
| 000412 | 000 001 | 000024 | | | | | | |
| | 055172 | 073364 | 057126 | 110766 | 000023 | 056726 | 107206 | 056736 |
| | 056726 | 073516 | | | | | | |
| 000413 | 000 001 | 000020 | | | | | | |
| | 055214 | 107206 | 057130 | 107310 | 110012 | 110546 | 073364 | 057150 |
| 000414 | 000 001 | 000024 | | | | | | |
| | 055232 | 110766 | 000024 | 056746 | 107206 | 056756 | 056746 | 073516 |
| | 107206 | 057130 | | | | | | |
| 000415 | 000 001 | 000024 | | | | | | |
| | 055254 | 107310 | 110012 | 110546 | 073364 | 057160 | 110766 | 000025 |
| | 114642 | 000004 | | | | | | |
| 000416 | 000 001 | 000030 | | | | | | |
| | 055276 | 055330 | 114642 | 000006 | 055332 | 114642 | 000002 | 055334 |
| | 114642 | 000020 | 055354 | 114576 | | | | |
| 000417 | 000 001 | 000040 | | | | | | |
| | 055324 | 066416 | 000414 | 000000 | 000000 | 000000 | 057150 | 057160 |
| | 056724 | 056714 | 057170 | 057200 | 057210 | 000000 | 057220 | 004467 |
| 000420 | 000 001 | 000022 | | | | | | |
| | 055362 | 037234 | 110766 | 000026 | 057212 | 056664 | 073512 | 074024 |
| | 073634 | | | | | | | |
| 000421 | 000 001 | 000024 | | | | | | |
| | 055402 | 055410 | 073570 | 055750 | 110766 | 000027 | 056676 | 057222 |
| | 106334 | 056636 | | | | | | |
| 000422 | 000 001 | 000022 | | | | | | |
| | 055424 | 073442 | 110766 | 000030 | 056664 | 057232 | 106334 | 056636 |
| | 073442 | | | | | | | |
| 000423 | 000 001 | 000026 | | | | | | |
| | 055444 | 110766 | 000031 | 056664 | 057242 | 106334 | 056636 | 073442 |
| | 110766 | 000032 | 056716 | | | | | |
| 000424 | 000 001 | 000026 | | | | | | |
| | 055470 | 056706 | 106342 | 056576 | 073650 | 055510 | 114576 | 070612 |
| | 000401 | 000000 | 004467 | | | | | |
| 000425 | 000 001 | 000020 | | | | | | |
| | 055514 | 037102 | 110762 | 057252 | 073516 | 057040 | 106334 | 056636 |
| 000426 | 000 001 | 000024 | | | | | | |
| | 055532 | 073442 | 110766 | 000033 | 057142 | 057152 | 106342 | 056576 |
| | 073650 | 055562 | | | | | | |
| 000427 | 000 001 | 000026 | | | | | | |
| | 055554 | 114576 | 070612 | 000401 | 000000 | 004467 | 037030 | 110762 |
| | 057050 | 106334 | 056636 | | | | | |
| 000430 | 000 001 | 000022 | | | | | | |
| | 055400 | 073442 | 110766 | 000034 | 057050 | 106334 | 056636 | 073430 |
| | 057262 | | | | | | | |
| 000431 | 000 001 | 000020 | | | | | | |
| | 055620 | 073512 | 074034 | 073634 | 055654 | 057050 | 106334 | 056636 |
| 000432 | 000 001 | 000020 | | | | | | |
| | 055636 | 073430 | 057202 | 073516 | 057050 | 106334 | 056636 | 073442 |
| 000433 | 000 001 | 000024 | | | | | | |
| | 055654 | 110766 | 000035 | 057272 | 106334 | 056636 | 073430 | 056676 |
| | 106334 | 056636 | | | | | | |
| 000434 | 000 001 | 000022 | | | | | | |
| | 055676 | 073430 | 107726 | 057302 | 106334 | 056636 | 073442 | 110766 |
| | 000036 | | | | | | | |
| 000435 | 000 001 | 000024 | | | | | | |
| | 055716 | 057120 | 056664 | 073512 | 074034 | 073634 | 055742 | 056676 |
| | 114632 | 000030 | | | | | | |
| 000436 | 000 001 | 000024 | | | | | | |
| | 055740 | 073442 | 110766 | 000037 | 106244 | 110766 | 000040 | 057172 |
| | 056676 | 073516 | | | | | | |
| 000437 | 000 001 | 000024 | | | | | | |
| | 055762 | 056606 | 106474 | 057162 | 073474 | 114632 | 000016 | 073442 |
| | 110766 | 000041 | | | | | | |
| 000440 | 000 001 | 000024 | | | | | | |
| | 056004 | 114642 | 000002 | 056064 | 114642 | 000004 | 056066 | 114642 |
| | 000006 | 056070 | 114642 | 000010 | 056072 | | | |
| 000441 | 000 001 | 000026 | | | | | | |
| | 056034 | 114642 | 000012 | 056074 | 114642 | 000010 | 056076 | 114642 |
| | 000014 | 056100 | 114576 | | | | | |
| 000442 | 000 001 | 000050 | | | | | | |
| | 056060 | 052476 | 000410 | 000000 | 000000 | 000000 | 000000 | 000000 |
| | 000000 | 000000 | 057312 | 004467 | 036510 | 110766 | 000042 | 114642 |
| | 000002 | 056144 | 114642 | 000010 | | | | |

| | | | | | | | | |
|---|---|---|---|---|---|---|---|---|
| 000443 | 000 001 | 000034 | | | | | | |
| | 056126 | 056150 | 114642 | 000014 | 056152 | 114576 | 061620 | 000416 |
| | 000000 | 056474 | 000000 | 000000 | 056734 | 056744 | | |
| 000444 | 000 001 | 000026 | | | | | | |
| | 056160 | 056754 | 056764 | 056766 | 056770 | 057000 | 057170 | 057200 |
| | 057010 | 004467 | 036414 | | | | | |
| 000445 | 000 001 | 000022 | | | | | | |
| | 056204 | 110766 | 000043 | 056676 | 106334 | 056636 | 073430 | 107206 |
| | 057314 | | | | | | | |
| 000446 | 000 001 | 000024 | | | | | | |
| | 056224 | 106534 | 114576 | 107142 | 000401 | 056770 | 004467 | 036356 |
| | 110762 | 107206 | | | | | | |
| 000447 | 000 001 | 000022 | | | | | | |
| | 056246 | 107310 | 110546 | 057222 | 106334 | 056636 | 073442 | 110766 |
| | 000044 | | | | | | | |
| 000450 | 000 001 | 000020 | | | | | | |
| | 056266 | 057040 | 107206 | 057002 | 106534 | 073410 | 056310 | 114576 |
| 000451 | 000 001 | 000030 | | | | | | |
| | 056304 | 107764 | 000401 | 000000 | 004467 | 036306 | 000004 | 110760 |
| | 110546 | 057232 | 106334 | 056636 | | | | |
| 000452 | 000 001 | 000022 | | | | | | |
| | 056332 | 073442 | 110766 | 000045 | 057272 | 106334 | 056636 | 073430 |
| | 057120 | | | | | | | |
| 000453 | 000 001 | 000022 | | | | | | |
| | 056352 | 073474 | 057272 | 106334 | 056636 | 073442 | 110766 | 000046 |
| | 057272 | | | | | | | |
| 000454 | 000 001 | 000020 | | | | | | |
| | 056372 | 106334 | 056636 | 073430 | 056676 | 106334 | 056636 | 073430 |
| 000455 | 000 001 | 000024 | | | | | | |
| | 056410 | 107726 | 057302 | 106334 | 056636 | 073442 | 110766 | 000047 |
| | 114642 | 000004 | | | | | | |
| 000456 | 000 001 | 000030 | | | | | | |
| | 056432 | 056464 | 114642 | 000006 | 056466 | 114642 | 000002 | 056470 |
| | 114642 | 000020 | 056510 | 114576 | | | | |
| 000457 | 000 001 | 000040 | | | | | | |
| | 056460 | 066416 | 000414 | 000000 | 000000 | 000000 | 057150 | 057160 |
| | 057170 | 057200 | 057326 | 057330 | 057210 | 000000 | 057220 | 004467 |
| 000460 | 000 001 | 000022 | | | | | | |
| | 056516 | 036100 | 110766 | 000050 | 056664 | 057242 | 106334 | 056636 |
| | 073442 | | | | | | | |
| 000461 | 000 001 | 000024 | | | | | | |
| | 056536 | 110766 | 000051 | 057212 | 056664 | 073512 | 074024 | 073634 |
| | 056570 | 056676 | | | | | | |
| 000462 | 000 001 | 000050 | | | | | | |
| | 056560 | 057242 | 106334 | 056636 | 073442 | 110766 | 000052 | 106244 |
| | 000000 | 100001 | 000000 | 000000 | 017546 | 000004 | 000134 | 017546 |
| | 000006 | 000134 | 000000 | 040001 | | | | |
| 000463 | 000 001 | 000020 | | | | | | |
| | 056626 | 000000 | 017546 | 000022 | 000134 | 000000 | 050002 | 000000 |
| 000464 | 000 001 | 000050 | | | | | | |
| | 056664 | 012746 | 000000 | 000134 | 000000 | 000000 | 012746 | 000001 |
| | 000134 | 000001 | 016746 | 000002 | 000134 | 000000 | 016746 | 000002 |
| | 000134 | 000000 | 016746 | 000002 | | | | |
| 000465 | 000 001 | 000050 | | | | | | |
| | 056732 | 000134 | 000000 | 016746 | 000002 | 000134 | 000000 | 016746 |
| | 000002 | 000134 | 000000 | 016746 | 000002 | 000134 | 000000 | 000000 |
| | 000000 | 016746 | 000002 | 000134 | | | | |
| 000466 | 000 001 | 000050 | | | | | | |
| | 057000 | 000000 | 012700 | 057014 | 000551 | 000000 | 000000 | 016746 |
| | 000002 | 000134 | 000000 | 000000 | 016746 | 000002 | 000134 | 000000 |
| | 000000 | 012746 | 000012 | 000134 | | | | |
| 000467 | 000 001 | 000050 | | | | | | |
| | 057046 | 000012 | 012746 | 000013 | 000134 | 000013 | 012746 | 000002 |
| | 000134 | 000002 | 012746 | 000003 | 000134 | 000003 | 012746 | 000004 |
| | 000134 | 000004 | 012746 | 000011 | | | | |
| 000470 | 000 001 | 000050 | | | | | | |
| | 057114 | 000134 | 000011 | 016746 | 000002 | 000134 | 000000 | 012700 |
| | 057142 | 000476 | 040400 | 000000 | 016746 | 000002 | 000134 | 000000 |
| | 016746 | 000002 | 000134 | 000000 | | | | |
| 000471 | 000 001 | 000050 | | | | | | |
| | 057162 | 016746 | 000002 | 000134 | 000000 | 016746 | 000002 | 000134 |
| | 000000 | 012746 | 000100 | 000134 | 000100 | 016746 | 000002 | 000134 |
| | 000000 | 012746 | 000006 | 000134 | | | | |
| 000472 | 000 001 | 000050 | | | | | | |
| | 057230 | 000006 | 012746 | 000007 | 000134 | 000007 | 012746 | 000010 |
| | 000134 | 000010 | 012746 | 000300 | 000134 | 000300 | 012746 | 000077 |
| | 000134 | 000077 | 012746 | 000005 | | | | |
| 000473 | 000 001 | 000044 | | | | | | |
| | 057276 | 000134 | 000005 | 012746 | 000014 | 000134 | 000014 | 000000 |
| | 012700 | 057326 | 000404 | 041040 | 000000 | 000000 | 000000 | 014046 |
| | 014046 | 000134 | | | | | | |
| 000474 | 000 001 | 000046 | | | | | | |
| | 057340 | 004467 | 031404 | 106176 | 000000 | 000000 | 070514 | 140250 |
| | 110766 | 000002 | 073574 | 061356 | 000002 | 000004 | 177777 | 177777 |
| | 110766 | 000002 | 073574 | | | | | |
| 000475 | 000 001 | 000034 | | | | | | |
| | 057404 | 061364 | 000006 | 000010 | 177777 | 177777 | 110766 | 000003 |
| | 061400 | 106334 | 061356 | 073430 | 061400 | 106334 | | |
| 000476 | 000 001 | 000020 | | | | | | |
| | 057436 | 061364 | 073430 | 073512 | 074034 | 073634 | 057456 | 073570 |

| | | | | | | | | |
|---|---|---|---|---|---|---|---|---|
| 000477 | 000 001 | 000024 | | | | | | |
| | 057454 | 060444 | 110766 | 000004 | 061410 | 106334 | 061356 | 073430 |
| | 061410 | 106334 | | | | | | |
| 000500 | 000 001 | 000020 | | | | | | |
| | 057476 | 061364 | 073430 | 073512 | 074034 | 073634 | 057516 | 073570 |
| 000501 | 000 001 | 000024 | | | | | | |
| | 057514 | 060444 | 110766 | 000005 | 061420 | 106334 | 061356 | 073430 |
| | 061420 | 106334 | | | | | | |
| 000502 | 000 001 | 000020 | | | | | | |
| | 057536 | 061364 | 073430 | 073512 | 074034 | 073634 | 057556 | 073570 |
| 000503 | 000 001 | 000024 | | | | | | |
| | 057554 | 060444 | 110766 | 000006 | 061430 | 106334 | 061356 | 073430 |
| | 061440 | 106334 | | | | | | |
| 000504 | 000 001 | 000022 | | | | | | |
| | 057576 | 061356 | 073430 | 073516 | 073364 | 061456 | 110766 | 000007 |
| | 061460 | | | | | | | |
| 000505 | 000 001 | 000022 | | | | | | |
| | 057616 | 106334 | 061356 | 073430 | 061470 | 073512 | 074024 | 061372 |
| | 061450 | | | | | | | |
| 000506 | 000 001 | 000020 | | | | | | |
| | 057636 | 073512 | 074040 | 074002 | 073634 | 057654 | 073570 | 060776 |
| 000507 | 000 001 | 000024 | | | | | | |
| | 057654 | 110766 | 000010 | 061460 | 106334 | 061356 | 073430 | 061460 |
| | 106334 | 061364 | | | | | | |
| 000510 | 000 001 | 000020 | | | | | | |
| | 057676 | 073430 | 073512 | 074034 | 073634 | 057714 | 073570 | 060006 |
| 000511 | 000 001 | 000024 | | | | | | |
| | 057714 | 110766 | 000011 | 061500 | 106334 | 061356 | 073430 | 061500 |
| | 106334 | 061364 | | | | | | |
| 000512 | 000 001 | 000020 | | | | | | |
| | 057736 | 073430 | 073512 | 074034 | 073634 | 057754 | 073570 | 060170 |
| 000513 | 000 001 | 000022 | | | | | | |
| | 057754 | 110766 | 000012 | 061510 | 106334 | 061356 | 073430 | 061470 |
| | 073512 | | | | | | | |
| 000514 | 000 001 | 000022 | | | | | | |
| | 057774 | 074024 | 073634 | 060006 | 073570 | 060170 | 110766 | 000013 |
| | 061520 | | | | | | | |
| 000515 | 000 001 | 000020 | | | | | | |
| | 060014 | 106334 | 061356 | 073430 | 061430 | 106334 | 061364 | 073430 |
| 000516 | 000 001 | 000022 | | | | | | |
| | 060032 | 073512 | 074016 | 073634 | 060046 | 073570 | 060256 | 110766 |
| | 000014 | | | | | | | |
| 000517 | 000 001 | 000022 | | | | | | |
| | 060052 | 061470 | 106334 | 061356 | 073430 | 061470 | 106334 | 061364 |
| | 073430 | | | | | | | |
| 000520 | 000 001 | 000022 | | | | | | |
| | 060072 | 073512 | 074016 | 073634 | 060106 | 073570 | 060212 | 110766 |
| | 000015 | | | | | | | |
| 000521 | 000 001 | 000022 | | | | | | |
| | 060112 | 061470 | 106334 | 061356 | 073430 | 061510 | 106334 | 061364 |
| | 073430 | | | | | | | |
| 000522 | 000 001 | 000022 | | | | | | |
| | 060132 | 073512 | 074034 | 073634 | 060146 | 073570 | 060234 | 110766 |
| | 000016 | | | | | | | |
| 000523 | 000 001 | 000026 | | | | | | |
| | 060152 | 061470 | 114632 | 000014 | 073442 | 110766 | 000017 | 106244 |
| | 110766 | 000020 | 061440 | | | | | |
| 000524 | 000 001 | 000030 | | | | | | |
| | 060176 | 114632 | 000014 | 073442 | 110766 | 000021 | 106244 | 110766 |
| | 000022 | 061530 | 114632 | 000014 | | | | |
| 000525 | 000 001 | 000026 | | | | | | |
| | 060224 | 073442 | 110766 | 000023 | 106244 | 110766 | 000024 | 061540 |
| | 114632 | 000014 | 073442 | | | | | |
| 000526 | 000 001 | 000024 | | | | | | |
| | 060250 | 110766 | 000025 | 106244 | 110766 | 000026 | 061470 | 106334 |
| | 061356 | 073430 | | | | | | |
| 000527 | 000 001 | 000020 | | | | | | |
| | 060272 | 061470 | 106334 | 061364 | 073430 | 073512 | 074016 | 073634 |
| 000530 | 000 001 | 000024 | | | | | | |
| | 060310 | 060316 | 073570 | 060400 | 110766 | 000027 | 061470 | 106334 |
| | 061356 | 073430 | | | | | | |
| 000531 | 000 001 | 000020 | | | | | | |
| | 060332 | 061510 | 106334 | 061364 | 073430 | 073512 | 074034 | 073634 |
| 000532 | 000 001 | 000024 | | | | | | |
| | 060350 | 060356 | 073570 | 060422 | 110766 | 000030 | 061550 | 114632 |
| | 000014 | 073442 | | | | | | |
| 000533 | 000 001 | 000030 | | | | | | |
| | 060372 | 110766 | 000031 | 106244 | 110766 | 000032 | 061560 | 114632 |
| | 000014 | 073442 | 110766 | 000033 | | | | |
| 000534 | 000 001 | 000026 | | | | | | |
| | 060420 | 106244 | 110766 | 000034 | 061570 | 114632 | 000014 | 073442 |
| | 110766 | 000035 | 106244 | | | | | |
| 000535 | 000 001 | 000024 | | | | | | |
| | 060444 | 110766 | 000036 | 061470 | 106334 | 061356 | 073430 | 061510 |
| | 106334 | 061364 | | | | | | |
| 000536 | 000 001 | 000020 | | | | | | |
| | 060466 | 073430 | 073512 | 074014 | 073634 | 060504 | 073570 | 060526 |
| 000537 | 000 001 | 000030 | | | | | | |

|  |  |  |  |  |  |  |  |  |
|---|---|---|---|---|---|---|---|---|
|  | 060504 | 110766 | 000037 | 061600 | 114632 | 000014 | 073442 | 110766 |
|  | 000040 | 106244 | 110766 | 000041 |  |  |  |  |
| 000540 | 000 001 | 000022 |  |  |  |  |  |  |
|  | 060532 | 061410 | 106334 | 061356 | 073430 | 061410 | 106334 | 061364 |
|  | 073430 |  |  |  |  |  |  |  |
| 000541 | 000 001 | 000022 |  |  |  |  |  |  |
|  | 060552 | 073512 | 074034 | 073634 | 060566 | 073570 | 060672 | 110766 |
|  | 000042 |  |  |  |  |  |  |  |
| 000542 | 000 001 | 000022 |  |  |  |  |  |  |
|  | 060572 | 061420 | 106334 | 061356 | 073430 | 061420 | 106334 | 061364 |
|  | 073430 |  |  |  |  |  |  |  |
| 000543 | 000 001 | 000022 |  |  |  |  |  |  |
|  | 060412 | 073512 | 074034 | 073634 | 060626 | 073570 | 060650 | 110766 |
|  | 000043 |  |  |  |  |  |  |  |
| 000544 | 000 001 | 000026 |  |  |  |  |  |  |
|  | 060632 | 061610 | 114632 | 000014 | 073442 | 110766 | 000044 | 106244 |
|  | 110766 | 000045 | 061430 |  |  |  |  |  |
| 000545 | 000 001 | 000026 |  |  |  |  |  |  |
|  | 060656 | 114632 | 000014 | 073442 | 110766 | 000046 | 106244 | 110766 |
|  | 000047 | 061420 | 106334 |  |  |  |  |  |
| 000546 | 000 001 | 000020 |  |  |  |  |  |  |
|  | 060702 | 061356 | 073430 | 061420 | 106334 | 061364 | 073430 | 073512 |
| 000547 | 000 001 | 000022 |  |  |  |  |  |  |
|  | 060720 | 074034 | 073634 | 060732 | 073570 | 060754 | 110766 | 000050 |
|  | 061510 |  |  |  |  |  |  |  |
| 000550 | 000 001 | 000030 |  |  |  |  |  |  |
|  | 060740 | 114632 | 000014 | 073442 | 110766 | 000051 | 106244 | 110766 |
|  | 000052 | 061500 | 114632 | 000014 |  |  |  |  |
| 000551 | 000 001 | 000024 |  |  |  |  |  |  |
|  | 060766 | 073442 | 110766 | 000053 | 106244 | 110766 | 000054 | 061470 |
|  | 106334 | 061356 |  |  |  |  |  |  |
| 000552 | 000 001 | 000020 |  |  |  |  |  |  |
|  | 061010 | 073430 | 061470 | 106334 | 061364 | 073430 | 073512 | 074016 |
| 000553 | 000 001 | 000022 |  |  |  |  |  |  |
|  | 061026 | 061560 | 106334 | 061356 | 073430 | 061440 | 106334 | 061364 |
|  | 073430 |  |  |  |  |  |  |  |
| 000554 | 000 001 | 000020 |  |  |  |  |  |  |
|  | 061046 | 073512 | 074034 | 074010 | 073634 | 061064 | 073570 | 061246 |
| 000555 | 000 001 | 000024 |  |  |  |  |  |  |
|  | 061064 | 110766 | 000055 | 061470 | 106334 | 061356 | 073430 | 061510 |
|  | 106334 | 061364 |  |  |  |  |  |  |
| 000556 | 000 001 | 000020 |  |  |  |  |  |  |
|  | 061106 | 073430 | 073512 | 074034 | 073634 | 061124 | 073570 | 061270 |
| 000557 | 000 001 | 000024 |  |  |  |  |  |  |
|  | 061124 | 110766 | 000056 | 061520 | 106334 | 061356 | 073430 | 061430 |
|  | 106334 | 061364 |  |  |  |  |  |  |
| 000560 | 000 001 | 000020 |  |  |  |  |  |  |
|  | 061146 | 073430 | 073512 | 074016 | 073634 | 061164 | 073570 | 061312 |
| 000561 | 000 001 | 000024 |  |  |  |  |  |  |
|  | 061164 | 110766 | 000057 | 061520 | 106334 | 061356 | 073430 | 061610 |
|  | 106334 | 061364 |  |  |  |  |  |  |
| 000562 | 000 001 | 000020 |  |  |  |  |  |  |
|  | 061206 | 073430 | 073512 | 074034 | 073634 | 061224 | 073570 | 061334 |
| 000563 | 000 001 | 000030 |  |  |  |  |  |  |
|  | 061224 | 110766 | 000060 | 061400 | 114632 | 000014 | 073442 | 110766 |
|  | 000061 | 106244 | 110766 | 000062 |  |  |  |  |
| 000564 | 000 001 | 000026 |  |  |  |  |  |  |
|  | 061252 | 061460 | 114632 | 000014 | 073442 | 110766 | 000063 | 106244 |
|  | 110766 | 000064 | 061410 |  |  |  |  |  |
| 000565 | 000 001 | 000030 |  |  |  |  |  |  |
|  | 061276 | 114632 | 000014 | 073442 | 110766 | 000065 | 106244 | 110766 |
|  | 000066 | 061400 | 114632 | 000014 |  |  |  |  |
| 000566 | 000 001 | 000026 |  |  |  |  |  |  |
|  | 061324 | 073442 | 110766 | 000067 | 106244 | 110766 | 000070 | 061400 |
|  | 114632 | 000014 | 073442 |  |  |  |  |  |
| 000567 | 000 001 | 000050 |  |  |  |  |  |  |
|  | 061350 | 110766 | 000071 | 106244 | 000000 | 050002 | 000000 | 000000 |
|  | 050002 | 000000 | 017546 | 000012 | 000134 | 012746 | 000002 | 000134 |
|  | 000002 | 012746 | 000003 | 000134 |  |  |  |  |
| 000570 | 000 001 | 000050 |  |  |  |  |  |  |
|  | 061416 | 000003 | 012746 | 000004 | 000134 | 000004 | 012746 | 000011 |
|  | 000134 | 000011 | 012746 | 000013 | 000134 | 000013 | 016746 | 000002 |
|  | 000134 | 000000 | 012746 | 000006 |  |  |  |  |
| 000571 | 000 001 | 000050 |  |  |  |  |  |  |
|  | 061464 | 000134 | 000006 | 012746 | 000001 | 000134 | 000001 | 012746 |
|  | 000007 | 000134 | 000007 | 012746 | 000010 | 000134 | 000010 | 012746 |
|  | 000005 | 000134 | 000005 | 012746 |  |  |  |  |
| 000572 | 000 001 | 000050 |  |  |  |  |  |  |
|  | 061532 | 000017 | 000134 | 000017 | 012746 | 000020 | 000134 | 000020 |
|  | 012746 | 000015 | 000134 | 000015 | 012746 | 000014 | 000134 | 000014 |
|  | 012746 | 000016 | 000134 | 000016 |  |  |  |  |
| 000573 | 000 001 | 000022 |  |  |  |  |  |  |
|  | 061600 | 012746 | 000000 | 000134 | 000000 | 012746 | 000012 | 000134 |
|  | 000012 |  |  |  |  |  |  |  |
| 000574 | 000 001 | 000046 |  |  |  |  |  |  |
|  | 061620 | 004467 | 027124 | 106176 | 000000 | 000000 | 071733 | 033317 |
|  | 110766 | 000002 | 073574 | 063336 | 000006 | 000010 | 177777 | 177777 |
|  | 110766 | 000002 | 073574 |  |  |  |  |  |
| 000575 | 000 001 | 000050 |  |  |  |  |  |  |

|        |        |        |        |        |        |        |        |        |
|--------|--------|--------|--------|--------|--------|--------|--------|--------|
|        | 061664 | 063330 | 000002 | 000004 | 177777 | 177777 | 073570 | 061742 |
|        | 000001 | 000000 | 000001 | 177777 | 000000 | 177777 | 177777 | 177777 |
|        | 177777 | 000000 | 177777 | 000001 |        |        |        |        |
| 000576 | 000 001 | 000040 |        |        |        |        |        |        |
|        | 061732 | 000000 | 000001 | 000001 | 000001 | 110766 | 000005 | 063374 |
|        | 114632 | 000014 | 073442 | 110766 | 000006 | 063374 | 114632 | 000012 |
| 000577 | 000 001 | 000026 |        |        |        |        |        |        |
|        | 061770 | 073442 | 110766 | 000007 | 063402 | 114632 | 000020 | 073442 |
|        | 110766 | 000010 | 063402 |        |        |        |        |        |
| 000600 | 000 001 | 000026 |        |        |        |        |        |        |
|        | 062014 | 114632 | 000016 | 073442 | 110766 | 000011 | 114632 | 000030 |
|        | 073430 | 073364 | 063426 |        |        |        |        |        |
| 000601 | 000 001 | 000026 |        |        |        |        |        |        |
|        | 062040 | 110766 | 000012 | 114632 | 000032 | 073430 | 073364 | 063436 |
|        | 110766 | 000013 | 063440 |        |        |        |        |        |
| 000602 | 000 001 | 000022 |        |        |        |        |        |        |
|        | 062064 | 073404 | 063460 | 110766 | 000014 | 063464 | 106334 | 063336 |
|        | 074064 |        |        |        |        |        |        |        |
| 000603 | 000 001 | 000022 |        |        |        |        |        |        |
|        | 062104 | 074056 | 063464 | 073474 | 073364 | 063502 | 110766 | 000015 |
|        | 063504 |        |        |        |        |        |        |        |
| 000604 | 000 001 | 000026 |        |        |        |        |        |        |
|        | 062124 | 073364 | 063522 | 110766 | 000016 | 063504 | 073364 | 063532 |
|        | 110766 | 000017 | 063504 |        |        |        |        |        |
| 000605 | 000 001 | 000026 |        |        |        |        |        |        |
|        | 062150 | 073364 | 063542 | 110766 | 000020 | 063504 | 073364 | 063552 |
|        | 110766 | 000021 | 063402 |        |        |        |        |        |
| 000606 | 000 001 | 000022 |        |        |        |        |        |        |
|        | 062174 | 063554 | 063474 | 106342 | 063410 | 073430 | 073474 | 073364 |
|        | 063572 |        |        |        |        |        |        |        |
| 000607 | 000 001 | 000026 |        |        |        |        |        |        |
|        | 062214 | 110766 | 000022 | 063464 | 073364 | 063602 | 110766 | 000023 |
|        | 063574 | 106334 | 063336 |        |        |        |        |        |
| 000610 | 000 001 | 000022 |        |        |        |        |        |        |
|        | 062240 | 074064 | 074056 | 063464 | 073474 | 073364 | 063502 | 110766 |
|        | 000024 |        |        |        |        |        |        |        |
| 000611 | 000 001 | 000022 |        |        |        |        |        |        |
|        | 062260 | 063464 | 063474 | 106342 | 063410 | 073430 | 063420 | 073474 |
|        | 073364 |        |        |        |        |        |        |        |
| 000612 | 000 001 | 000024 |        |        |        |        |        |        |
|        | 062300 | 063426 | 110766 | 000025 | 063554 | 063474 | 106342 | 063410 |
|        | 073430 | 063430 |        |        |        |        |        |        |
| 000613 | 000 001 | 000022 |        |        |        |        |        |        |
|        | 062322 | 073474 | 073364 | 063436 | 110766 | 000026 | 063574 | 106334 |
|        | 063336 |        |        |        |        |        |        |        |
| 000614 | 000 001 | 000020 |        |        |        |        |        |        |
|        | 062342 | 074064 | 074056 | 063604 | 073512 | 074044 | 073634 | 062364 |
| 000615 | 000 001 | 000024 |        |        |        |        |        |        |
|        | 062360 | 073570 | 062562 | 110766 | 000027 | 063430 | 063464 | 073516 |
|        | 063614 | 106474 |        |        |        |        |        |        |
| 000616 | 000 001 | 000024 |        |        |        |        |        |        |
|        | 062402 | 063420 | 073474 | 073364 | 063632 | 110766 | 000030 | 063624 |
|        | 063634 | 073516 |        |        |        |        |        |        |
| 000617 | 000 001 | 000024 |        |        |        |        |        |        |
|        | 062424 | 073364 | 063652 | 110766 | 000031 | 063624 | 063554 | 073474 |
|        | 073364 | 063632 |        |        |        |        |        |        |
| 000620 | 000 001 | 000022 |        |        |        |        |        |        |
|        | 062446 | 110766 | 000032 | 063624 | 106334 | 063330 | 073650 | 062472 |
|        | 114576 |        |        |        |        |        |        |        |
| 000621 | 000 001 | 000026 |        |        |        |        |        |        |
|        | 062466 | 070612 | 000401 | 000000 | 004467 | 032120 | 110762 | 063534 |
|        | 073474 | 063644 | 106334 |        |        |        |        |        |
| 000622 | 000 001 | 000026 |        |        |        |        |        |        |
|        | 062512 | 063330 | 073650 | 062526 | 114576 | 070612 | 000401 | 000000 |
|        | 004467 | 032064 | 110762 |        |        |        |        |        |
| 000623 | 000 001 | 000022 |        |        |        |        |        |        |
|        | 062536 | 073516 | 073364 | 063542 | 110766 | 000033 | 063544 | 063464 |
|        | 073474 |        |        |        |        |        |        |        |
| 000624 | 000 001 | 000022 |        |        |        |        |        |        |
|        | 062556 | 073364 | 063552 | 110766 | 000034 | 063352 | 063420 | 073512 |
|        | 074016 |        |        |        |        |        |        |        |
| 000625 | 000 001 | 000026 |        |        |        |        |        |        |
|        | 062576 | 073634 | 062612 | 063420 | 114632 | 000014 | 073442 | 110766 |
|        | 000035 | 063344 | 063420 |        |        |        |        |        |
| 000626 | 000 001 | 000022 |        |        |        |        |        |        |
|        | 062622 | 073512 | 074034 | 073634 | 062642 | 063420 | 114632 | 000012 |
|        | 073442 |        |        |        |        |        |        |        |
| 000627 | 000 001 | 000024 |        |        |        |        |        |        |
|        | 062642 | 110766 | 000036 | 063364 | 063430 | 073512 | 074016 | 073634 |
|        | 062672 | 063430 |        |        |        |        |        |        |
| 000630 | 000 001 | 000024 |        |        |        |        |        |        |
|        | 062664 | 114632 | 000020 | 073442 | 110766 | 000037 | 063360 | 063430 |
|        | 073512 | 074034 |        |        |        |        |        |        |
| 000631 | 000 001 | 000026 |        |        |        |        |        |        |
|        | 062706 | 073634 | 062722 | 063430 | 114632 | 000016 | 073442 | 110766 |
|        | 000040 | 063464 | 063474 |        |        |        |        |        |
| 000632 | 000 001 | 000022 |        |        |        |        |        |        |
|        | 062732 | 106342 | 063410 | 073430 | 107206 | 063564 | 107206 | 063554 |
|        | 063474 |        |        |        |        |        |        |        |

| | | | | | | | | |
|---|---|---|---|---|---|---|---|---|
| 000633 | 000 001 | 000020 | | | | | | |
| | 062752 | 106342 | 063410 | 073430 | 107206 | 063654 | 106534 | 110012 |
| 000634 | 000 001 | 000024 | | | | | | |
| | 062770 | 106534 | 063452 | 110012 | 073404 | 063460 | 110766 | 000041 |
| | 063554 | 063474 | | | | | | |
| 000635 | 000 001 | 000020 | | | | | | |
| | 063012 | 106342 | 063410 | 073430 | 063564 | 073474 | 073364 | 063572 |
| 000636 | 000 001 | 000030 | | | | | | |
| | 063030 | 110766 | 000042 | 063474 | 073534 | 000010 | 063062 | 063110 |
| | 063062 | 063110 | 063062 | 063110 | | | | |
| 000637 | 000 001 | 000024 | | | | | | |
| | 063056 | 063062 | 063110 | 110766 | 000043 | 063514 | 063464 | 073474 |
| | 073364 | 063522 | | | | | | |
| 000640 | 000 001 | 000024 | | | | | | |
| | 063100 | 110766 | 000044 | 073570 | 063126 | 110766 | 000045 | 063524 |
| | 063464 | 073474 | | | | | | |
| 000641 | 000 001 | 000030 | | | | | | |
| | 063122 | 073364 | 063532 | 110766 | 000046 | 073712 | 063472 | 063602 |
| | 000010 | 062226 | 110766 | 000047 | | | | |
| 000642 | 000 001 | 000020 | | | | | | |
| | 063150 | 063514 | 107206 | 063524 | 107206 | 063666 | 106534 | 110012 |
| 000643 | 000 001 | 000024 | | | | | | |
| | 063166 | 073404 | 063706 | 110766 | 000050 | 063700 | 063700 | 106534 |
| | 063452 | 107310 | | | | | | |
| 000644 | 000 001 | 000026 | | | | | | |
| | 063210 | 114632 | 000034 | 073440 | 110766 | 000051 | 063452 | 110546 |
| | 114632 | 000024 | 073442 | | | | | |
| 000645 | 000 001 | 000026 | | | | | | |
| | 063234 | 110766 | 000052 | 063700 | 110546 | 114632 | 000022 | 073442 |
| | 110766 | 000053 | 063504 | | | | | |
| 000646 | 000 001 | 000024 | | | | | | |
| | 063260 | 114632 | 000026 | 073442 | 110766 | 000054 | 063544 | 063504 |
| | 073512 | 074044 | | | | | | |
| 000647 | 000 001 | 000022 | | | | | | |
| | 063302 | 073634 | 063322 | 063534 | 063544 | 107726 | 114632 | 000026 |
| | 073442 | | | | | | | |
| 000650 | 000 001 | 000050 | | | | | | |
| | 063322 | 110766 | 000055 | 106244 | 000000 | 040001 | 000000 | 000000 |
| | 040001 | 000000 | 017546 | 000012 | 000134 | 017546 | 000014 | 000134 |
| | 017546 | 000016 | 000134 | 017546 | | | | |
| 000651 | 000 001 | 000050 | | | | | | |
| | 063370 | 000020 | 000134 | 017546 | 000030 | 000134 | 017546 | 000032 |
| | 000134 | 061702 | 110002 | 000002 | 000010 | 016746 | 000002 | 000134 |
| | 000000 | 016746 | 000002 | 000134 | | | | |
| 000652 | 000 001 | 000050 | | | | | | |
| | 063436 | 000000 | 012700 | 063452 | 000522 | 000000 | 000000 | 012700 |
| | 063464 | 000515 | 000000 | 000000 | 012746 | 000001 | 000134 | 000001 |
| | 016746 | 000002 | 000134 | 000000 | | | | |
| 000653 | 000 001 | 000050 | | | | | | |
| | 063504 | 012746 | 000000 | 000134 | 000000 | 016746 | 000002 | 000134 |
| | 000000 | 016746 | 000002 | 000134 | 000000 | 016746 | 000002 | 000134 |
| | 000000 | 016746 | 000002 | 000134 | | | | |
| 000654 | 000 001 | 000050 | | | | | | |
| | 063552 | 000000 | 012746 | 000002 | 000134 | 000002 | 016746 | 000002 |
| | 000134 | 000000 | 016746 | 000002 | 000134 | 000000 | 012746 | 000006 |
| | 000134 | 000006 | 012744 | 000204 | | | | |
| 000655 | 000 001 | 000050 | | | | | | |
| | 063620 | 000134 | 000204 | 016746 | 000002 | 000134 | 000000 | 012746 |
| | 000003 | 000134 | 000003 | 016746 | 000002 | 000134 | 000000 | 012700 |
| | 063666 | 000414 | 040000 | 000000 | | | | |
| 000656 | 000 001 | 000034 | | | | | | |
| | 063666 | 012700 | 063700 | 000407 | 040265 | 002356 | 012700 | 063712 |
| | 000402 | 000000 | 000000 | 014046 | 014046 | 000134 | | |
| 000657 | 000 001 | 000046 | | | | | | |
| | 063720 | 004467 | 025024 | 106176 | 000000 | 000000 | 071733 | 033320 |
| | 110766 | 000002 | 073574 | 065160 | 000002 | 000004 | 177777 | 177777 |
| | 110766 | 000003 | 073574 | | | | | |
| 000660 | 000 001 | 000036 | | | | | | |
| | 063764 | 065174 | 000006 | 177777 | 177777 | 177777 | 110766 | 000004 |
| | 065212 | 073364 | 065210 | 110766 | 000005 | 065232 | 065202 | |
| 000661 | 000 001 | 000022 | | | | | | |
| | 064020 | 106334 | 065174 | 073442 | 073654 | 065220 | 065210 | 065230 |
| | 064010 | | | | | | | |
| 000662 | 000 001 | 000026 | | | | | | |
| | 064040 | 110766 | 000006 | 065212 | 073364 | 065210 | 110766 | 000007 |
| | 065202 | 106334 | 065160 | | | | | |
| 000663 | 000 001 | 000026 | | | | | | |
| | 064064 | 073650 | 064076 | 114576 | 070612 | 000401 | 000000 | 004467 |
| | 030514 | 110762 | 065212 | | | | | |
| 000664 | 000 001 | 000022 | | | | | | |
| | 064110 | 073474 | 073364 | 065250 | 110766 | 000010 | 065242 | 106334 |
| | 065174 | | | | | | | |
| 000665 | 000 001 | 000020 | | | | | | |
| | 064130 | 073430 | 065212 | 073474 | 065242 | 106334 | 065174 | 073442 |
| 000666 | 000 001 | 000026 | | | | | | |
| | 064146 | 073712 | 065220 | 065210 | 000004 | 064052 | 110766 | 000011 |
| | 065166 | 107206 | 073404 | | | | | |
| 000667 | 000 001 | 000026 | | | | | | |

|        |        |        |        |        |        |        |        |        |
|--------|--------|--------|--------|--------|--------|--------|--------|--------|
|        | 064172 | 065260 | 110766 | 000012 | 065264 | 073364 | 065210 | 110766 |
|        | 000013 | 065202 | 106334 |        |        |        |        |        |
| 000670 | 000 001 | 000020 |       |        |        |        |        |        |
|        | 064216 | 065174 | 073430 | 107206 | 065274 | 106534 | 073404 | 065314 |
| 000671 | 000 001 | 000022 |       |        |        |        |        |        |
|        | 064234 | 110766 | 000014 | 065202 | 106334 | 065174 | 073430 | 107206 |
|        | 114674 |        |        |        |        |        |        |        |
| 000672 | 000 001 | 000024 |       |        |        |        |        |        |
|        | 064254 | 065314 | 110006 | 065252 | 110012 | 073404 | 065260 | 110766 |
|        | 000015 | 065306 |        |        |        |        |        |        |
| 000673 | 000 001 | 000022 |       |        |        |        |        |        |
|        | 064276 | 110546 | 065202 | 106334 | 065174 | 073442 | 073654 | 065272 |
|        | 065210 |        |        |        |        |        |        |        |
| 000674 | 000 001 | 000026 |       |        |        |        |        |        |
|        | 064316 | 065230 | 064206 | 110766 | 000016 | 065212 | 073364 | 065210 |
|        | 110766 | 000017 | 065202 |       |        |        |        |        |
| 000675 | 000 001 | 000020 |       |        |        |        |        |        |
|        | 064342 | 106334 | 065174 | 073430 | 065232 | 073512 | 074024 | 073634 |
| 000676 | 000 001 | 000024 |       |        |        |        |        |        |
|        | 064360 | 064366 | 073570 | 064426 | 110766 | 000020 | 065202 | 106334 |
|        | 065174 | 073430 |        |        |        |        |        |        |
| 000677 | 000 001 | 000020 |       |        |        |        |        |        |
|        | 064402 | 107206 | 065320 | 106534 | 065252 | 107310 | 110546 | 065202 |
| 000700 | 000 001 | 000024 |       |        |        |        |        |        |
|        | 064420 | 106334 | 065174 | 073442 | 110766 | 000021 | 073654 | 065220 |
|        | 065210 | 065230 |        |        |        |        |        |        |
| 000701 | 000 001 | 000024 |       |        |        |        |        |        |
|        | 064442 | 064334 | 110766 | 000022 | 065212 | 106334 | 065174 | 073430 |
|        | 065332 | 106334 |        |        |        |        |        |        |
| 000702 | 000 001 | 000022 |       |        |        |        |        |        |
|        | 064464 | 065174 | 073430 | 073474 | 073364 | 065350 | 110766 | 000023 |
|        | 065264 |        |        |        |        |        |        |        |
| 000703 | 000 001 | 000020 |       |        |        |        |        |        |
|        | 064504 | 106334 | 065174 | 073430 | 065352 | 106334 | 065174 | 073430 |
| 000704 | 000 001 | 000022 |       |        |        |        |        |        |
|        | 064522 | 073474 | 073364 | 065370 | 110766 | 000024 | 065372 | 106334 |
|        | 065174 |        |        |        |        |        |        |        |
| 000705 | 000 001 | 000020 |       |        |        |        |        |        |
|        | 064542 | 073430 | 065402 | 106334 | 065174 | 073430 | 073474 | 073364 |
| 000706 | 000 001 | 000024 |       |        |        |        |        |        |
|        | 064560 | 065420 | 110766 | 000025 | 065422 | 106334 | 065174 | 073430 |
|        | 065222 | 106334 |        |        |        |        |        |        |
| 000707 | 000 001 | 000024 |       |        |        |        |        |        |
|        | 064602 | 065174 | 073430 | 073474 | 073364 | 065440 | 110766 | 000026 |
|        | 065342 | 065412 |        |        |        |        |        |        |
| 000710 | 000 001 | 000022 |       |        |        |        |        |        |
|        | 064624 | 073516 | 073364 | 065450 | 110766 | 000027 | 065362 | 065432 |
|        | 073516 |        |        |        |        |        |        |        |
| 000711 | 000 001 | 000026 |       |        |        |        |        |        |
|        | 064644 | 073364 | 065460 | 110766 | 000030 | 114576 | 107142 | 000401 |
|        | 065450 | 004467 | 027730 |       |        |        |        |        |
| 000712 | 000 001 | 000026 |       |        |        |        |        |        |
|        | 064670 | 110762 | 073364 | 065470 | 110766 | 000031 | 114576 | 107142 |
|        | 000401 | 065460 | 004467 |       |        |        |        |        |
| 000713 | 000 001 | 000022 |       |        |        |        |        |        |
|        | 064714 | 027702 | 110762 | 073364 | 065500 | 110766 | 000032 | 065462 |
|        | 065472 |        |        |        |        |        |        |        |
| 000714 | 000 001 | 000026 |       |        |        |        |        |        |
|        | 064734 | 073516 | 106300 | 065004 | 064746 | 065072 | 110766 | 000033 |
|        | 065232 | 114632 | 000010 |       |        |        |        |        |
| 000715 | 000 001 | 000026 |       |        |        |        |        |        |
|        | 064760 | 073442 | 110766 | 000034 | 065212 | 114632 | 000012 | 073442 |
|        | 110766 | 000035 | 106244 |       |        |        |        |        |
| 000716 | 000 001 | 000030 |       |        |        |        |        |        |
|        | 065004 | 110766 | 000036 | 065472 | 114632 | 000010 | 073442 | 110766 |
|        | 000037 | 065264 | 114632 | 000012 |        |        |        |        |
| 000717 | 000 001 | 000022 |       |        |        |        |        |        |
|        | 065032 | 073442 | 110766 | 000040 | 065452 | 065232 | 073512 | 074016 |
|        | 073634 |        |        |        |        |        |        |        |
| 000720 | 000 001 | 000026 |       |        |        |        |        |        |
|        | 065052 | 065064 | 065422 | 114632 | 000012 | 073442 | 110766 | 000041 |
|        | 106244 | 110766 | 000042 |       |        |        |        |        |
| 000721 | 000 001 | 000026 |       |        |        |        |        |        |
|        | 065076 | 065462 | 114632 | 000010 | 073442 | 110766 | 000043 | 065212 |
|        | 114632 | 000012 | 073442 |       |        |        |        |        |
| 000722 | 000 001 | 000024 |       |        |        |        |        |        |
|        | 065122 | 110766 | 000044 | 065442 | 065232 | 073512 | 074016 | 073634 |
|        | 065152 | 065372 |        |        |        |        |        |        |
| 000723 | 000 001 | 000050 |       |        |        |        |        |        |
|        | 065144 | 114632 | 000012 | 073442 | 110766 | 000045 | 106244 | 000000 |
|        | 040001 | 000000 | 017546 | 000004 | 000134 | 000000 | 050002 | 000010 |
|        | 016746 | 000002 | 000134 | 000000 |        |        |        |        |
| 000724 | 000 001 | 000050 |       |        |        |        |        |        |
|        | 065212 | 012746 | 000001 | 000134 | 000001 | 012746 | 000010 | 000134 |
|        | 000010 | 012746 | 000000 | 000134 | 000000 | 016746 | 000002 | 000134 |
|        | 000000 | 012700 | 065264 | 000511 |        |        |        |        |

| | | | | | | | | |
|---|---|---|---|---|---|---|---|---|
| 000725 | 000 001 | 000050 | | | | | | |
| | 065260 | 000000 | 000000 | 012746 | 000002 | 000134 | 000002 | 012700 |
| | 065306 | 000500 | 040265 | 002356 | 012700 | 065320 | 000473 | 000000 |
| | 000000 | 012700 | 065332 | 000466 | | | | |
| 000726 | 000 001 | 000050 | | | | | | |
| | 065326 | 041710 | 000000 | 012746 | 000005 | 000134 | 000005 | 016746 |
| | 000002 | 000134 | 000000 | 012746 | 000006 | 000134 | 000006 | 016746 |
| | 000002 | 000134 | 000000 | 012746 | | | | |
| 000727 | 000 001 | 000050 | | | | | | |
| | 065374 | 000003 | 000134 | 000003 | 012746 | 000007 | 000134 | 000007 |
| | 016746 | 000002 | 000134 | 000000 | 012746 | 000004 | 000134 | 000004 |
| | 016746 | 000002 | 000134 | 000000 | | | | |
| 000730 | 000 001 | 000050 | | | | | | |
| | 065442 | 016746 | 000002 | 000134 | 000000 | 016746 | 000002 | 000134 |
| | 000000 | 016746 | 000002 | 000134 | 000000 | 016746 | 000002 | 000134 |
| | 000000 | 014046 | 014046 | 000134 | | | | |
| 000731 | 000 001 | 000050 | | | | | | |
| | 065510 | 004467 | 023234 | 106176 | 000000 | 000000 | 035442 | 020130 |
| | 110766 | 000002 | 073574 | 066302 | 000002 | 000004 | 177777 | 177777 |
| | 073570 | 065752 | 000003 | 000003 | | | | |
| 000732 | 000 001 | 000050 | | | | | | |
| | 065556 | 000001 | 000001 | 000004 | 000002 | 000002 | 000002 | 000002 |
| | 000003 | 000003 | 000001 | 000004 | 000002 | 000002 | 000002 | 000002 |
| | 000002 | 000003 | 000003 | 000001 | | | | |
| 000733 | 000 001 | 000050 | | | | | | |
| | 065624 | 000001 | 000004 | 000002 | 000002 | 000002 | 000002 | 000003 |
| | 000003 | 000001 | 000001 | 000004 | 000002 | 000002 | 000002 | 000002 |
| | 000003 | 000003 | 000001 | 000001 | | | | |
| 000734 | 000 001 | 000050 | | | | | | |
| | 065672 | 000001 | 000004 | 000002 | 000002 | 000002 | 000003 | 000003 |
| | 000001 | 000001 | 000001 | 000004 | 000002 | 000002 | 000002 | 000003 |
| | 000003 | 000003 | 000001 | 000001 | | | | |
| 000735 | 000 001 | 000044 | | | | | | |
| | 065740 | 000004 | 000002 | 000002 | 000002 | 000003 | 110766 | 000005 |
| | 066326 | 073452 | 000010 | 110766 | 000006 | 066326 | 073452 | 000006 |
| | 110766 | 000007 | | | | | | |
| 000736 | 000 001 | 000020 | | | | | | |
| | 066002 | 066336 | 106334 | 066302 | 074064 | 074056 | 073364 | 066354 |
| 000737 | 000 001 | 000026 | | | | | | |
| | 066020 | 110766 | 000010 | 066336 | 073364 | 066364 | 110766 | 000011 |
| | 066346 | 066336 | 073474 | | | | | |
| 000740 | 000 001 | 000022 | | | | | | |
| | 066044 | 073364 | 066374 | 110766 | 000012 | 066356 | 106334 | 066302 |
| | 074064 | | | | | | | |
| 000741 | 000 001 | 000024 | | | | | | |
| | 066064 | 074056 | 066336 | 073474 | 073364 | 066404 | 110766 | 000013 |
| | 066366 | 066376 | | | | | | |
| 000742 | 000 001 | 000022 | | | | | | |
| | 066106 | 106342 | 066316 | 073430 | 073364 | 066414 | 110766 | 000014 |
| | 066406 | | | | | | | |
| 000743 | 000 001 | 000026 | | | | | | |
| | 066126 | 073534 | 000004 | 066142 | 066212 | 066234 | 066262 | 110766 |
| | 000015 | 066310 | 066336 | | | | | |
| 000744 | 000 001 | 000024 | | | | | | |
| | 066152 | 073474 | 073452 | 000006 | 110766 | 000016 | 066356 | 106334 |
| | 066302 | 074064 | | | | | | |
| 000745 | 000 001 | 000024 | | | | | | |
| | 066174 | 074056 | 073364 | 066354 | 110766 | 000017 | 073570 | 066234 |
| | 110766 | 000020 | | | | | | |
| 000746 | 000 001 | 000020 | | | | | | |
| | 066216 | 066356 | 106334 | 066302 | 074064 | 074056 | 073364 | 066354 |
| 000747 | 000 001 | 000030 | | | | | | |
| | 066234 | 110766 | 000021 | 073712 | 066344 | 066364 | 000004 | 066032 |
| | 110766 | 000022 | 073570 | 066274 | | | | |
| 000750 | 000 001 | 000050 | | | | | | |
| | 066262 | 110766 | 000023 | 066336 | 073452 | 000010 | 110766 | 000024 |
| | 106244 | 000000 | 040001 | 000000 | 017546 | 000006 | 000134 | 065552 |
| | 110002 | 000010 | 000010 | 012746 | | | | |
| 000751 | 000 001 | 000050 | | | | | | |
| | 066330 | 000000 | 000134 | 000000 | 012746 | 000001 | 000134 | 000001 |
| | 016746 | 000002 | 000134 | 000000 | 016746 | 000002 | 000134 | 000000 |
| | 016746 | 000002 | 000134 | 000000 | | | | |
| 000752 | 000 001 | 000022 | | | | | | |
| | 066376 | 016746 | 000002 | 000134 | 000000 | 016746 | 000002 | 000134 |
| | 000000 | | | | | | | |
| 000753 | 000 001 | 000046 | | | | | | |
| | 066416 | 004467 | 022326 | 106176 | 000000 | 000000 | 063704 | 020477 |
| | 110766 | 000002 | 073574 | 070230 | 000006 | 000002 | 000004 | 177777 |
| | 110766 | 000003 | 070304 | | | | | |
| 000754 | 000 001 | 000026 | | | | | | |
| | 066462 | 114632 | 000030 | 073442 | 110766 | 000004 | 114632 | 000014 |
| | 073430 | 073364 | 070322 | | | | | |
| 000755 | 000 001 | 000026 | | | | | | |
| | 066506 | 110766 | 000005 | 114632 | 000016 | 073430 | 073364 | 070332 |
| | 110766 | 000006 | 070254 | | | | | |
| 000756 | 000 001 | 000024 | | | | | | |
| | 066532 | 070240 | 073516 | 073364 | 070342 | 110766 | 000007 | 070262 |
| | 070246 | 073516 | | | | | | |

| | | | | | | | | |
|---|---|---|---|---|---|---|---|---|
| 000757 | 000 001 | 000026 | | | | | | |
| | 066554 | 073364 | 070352 | 110766 | 000010 | 070304 | 073364 | 070362 |
| | 110766 | 000011 | 070334 | | | | | |
| 000760 | 000 001 | 000020 | | | | | | |
| | 066600 | 070364 | 073512 | 074040 | 073634 | 066616 | 073570 | 066650 |
| 000761 | 000 001 | 000026 | | | | | | |
| | 066616 | 110766 | 000012 | 070354 | 070304 | 073474 | 073364 | 070362 |
| | 110766 | 000013 | 070334 | | | | | |
| 000762 | 000 001 | 000022 | | | | | | |
| | 066642 | 074110 | 073364 | 070342 | 110766 | 000014 | 070344 | 070364 |
| | 073512 | | | | | | | |
| 000763 | 000 001 | 000024 | | | | | | |
| | 066662 | 074040 | 073634 | 066674 | 073570 | 066726 | 110766 | 000015 |
| | 070354 | 070374 | | | | | | |
| 000764 | 000 001 | 000022 | | | | | | |
| | 066704 | 073474 | 073364 | 070362 | 110766 | 000016 | 070344 | 074110 |
| | 073364 | | | | | | | |
| 000765 | 000 001 | 000024 | | | | | | |
| | 066724 | 070352 | 110766 | 000017 | 070334 | 070344 | 073512 | 074040 |
| | 073634 | 066752 | | | | | | |
| 000766 | 000 001 | 000024 | | | | | | |
| | 066746 | 073570 | 067026 | 110766 | 000020 | 070354 | 070404 | 073474 |
| | 073364 | 070362 | | | | | | |
| 000767 | 000 001 | 000026 | | | | | | |
| | 066770 | 110766 | 000021 | 070334 | 073364 | 070422 | 110766 | 000022 |
| | 070344 | 073364 | 070342 | | | | | |
| 000770 | 000 001 | 000026 | | | | | | |
| | 067014 | 110766 | 000023 | 070414 | 073364 | 070352 | 110766 | 000024 |
| | 070344 | 070374 | 106474 | | | | | |
| 000771 | 000 001 | 000026 | | | | | | |
| | 067040 | 073364 | 070352 | 110766 | 000025 | 070334 | 073364 | 070422 |
| | 110766 | 000026 | 070344 | | | | | |
| 000772 | 000 001 | 000024 | | | | | | |
| | 067064 | 070334 | 073516 | 073364 | 070432 | 110766 | 000027 | 070334 |
| | 070374 | 106474 | | | | | | |
| 000773 | 000 001 | 000022 | | | | | | |
| | 067106 | 073364 | 070342 | 110766 | 000030 | 070424 | 070364 | 073512 |
| | 074016 | | | | | | | |
| 000774 | 000 001 | 000024 | | | | | | |
| | 067126 | 073634 | 067136 | 073570 | 067372 | 110766 | 000031 | 070424 |
| | 070334 | 073516 | | | | | | |
| 000775 | 000 001 | 000026 | | | | | | |
| | 067150 | 073364 | 070432 | 110766 | 000032 | 070354 | 073534 | 000010 |
| | 067206 | 067252 | 067300 | | | | | |
| 000776 | 000 001 | 000026 | | | | | | |
| | 067174 | 067344 | 067206 | 067252 | 067300 | 067344 | 110766 | 000033 |
| | 070314 | 070304 | 073516 | | | | | |
| 000777 | 000 001 | 000024 | | | | | | |
| | 067220 | 073364 | 070322 | 110766 | 000034 | 070324 | 070304 | 073516 |
| | 073364 | 070332 | | | | | | |
| 001000 | 000 001 | 000024 | | | | | | |
| | 067242 | 110766 | 000035 | 073570 | 067470 | 110766 | 000036 | 070314 |
| | 070304 | 073474 | | | | | | |
| 001001 | 000 001 | 000026 | | | | | | |
| | 067264 | 073364 | 070322 | 110766 | 000037 | 073570 | 067224 | 110766 |
| | 000040 | 070314 | 070304 | | | | | |
| 001002 | 000 001 | 000022 | | | | | | |
| | 067310 | 073516 | 073364 | 070322 | 110766 | 000041 | 070324 | 070304 |
| | 073474 | | | | | | | |
| 001003 | 000 001 | 000026 | | | | | | |
| | 067330 | 073364 | 070332 | 110766 | 000042 | 073570 | 067470 | 110766 |
| | 000043 | 070314 | 070304 | | | | | |
| 001004 | 000 001 | 000024 | | | | | | |
| | 067354 | 073474 | 073364 | 070322 | 110766 | 000044 | 073570 | 067316 |
| | 110766 | 000045 | | | | | | |
| 001005 | 000 001 | 000026 | | | | | | |
| | 067376 | 070354 | 073534 | 000010 | 067452 | 067424 | 067452 | 067424 |
| | 067224 | 067224 | 067316 | | | | | |
| 001006 | 000 001 | 000026 | | | | | | |
| | 067422 | 067316 | 110766 | 000046 | 070314 | 070304 | 073474 | 073364 |
| | 070322 | 110766 | 000047 | | | | | |
| 001007 | 000 001 | 000024 | | | | | | |
| | 067446 | 073570 | 067470 | 110766 | 000050 | 070314 | 070304 | 073516 |
| | 073364 | 070322 | | | | | | |
| 001010 | 000 001 | 000024 | | | | | | |
| | 067470 | 110766 | 000051 | 070314 | 070324 | 106342 | 070230 | 074064 |
| | 074056 | 070270 | | | | | | |
| 001011 | 000 001 | 000022 | | | | | | |
| | 067512 | 073512 | 074016 | 073634 | 067526 | 073570 | 067600 | 110766 |
| | 000052 | | | | | | | |
| 001012 | 000 001 | 000026 | | | | | | |
| | 067532 | 070314 | 114632 | 000020 | 073442 | 110766 | 000053 | 070324 |
| | 114632 | 000022 | 073442 | | | | | |
| 001013 | 000 001 | 000030 | | | | | | |
| | 067556 | 110766 | 000054 | 070364 | 114632 | 000030 | 073442 | 110766 |
| | 000055 | 106244 | 110766 | 000056 | | | | |

| | | | | | | | | |
|---|---|---|---|---|---|---|---|---|
| 001014 | 000 001 | 000022 | | | | | | |
| | 067604 | 070314 | 070324 | 106342 | 070230 | 074064 | 074056 | 070276 |
| | 073512 | | | | | | | |
| 001015 | 000 001 | 000024 | | | | | | |
| | 067624 | 074034 | 073634 | 067636 | 073570 | 070142 | 110766 | 000057 |
| | 070314 | 070304 | | | | | | |
| 001016 | 000 001 | 000024 | | | | | | |
| | 067646 | 073474 | 073364 | 070322 | 110766 | 000060 | 070314 | 070324 |
| | 106342 | 070230 | | | | | | |
| 001017 | 000 001 | 000020 | | | | | | |
| | 067670 | 074064 | 074056 | 070270 | 073512 | 074040 | 073634 | 067712 |
| 001020 | 000 001 | 000024 | | | | | | |
| | 067706 | 073570 | 067526 | 110766 | 000061 | 070314 | 070374 | 073516 |
| | 073364 | 070322 | | | | | | |
| 001021 | 000 001 | 000024 | | | | | | |
| | 067730 | 110766 | 000062 | 070314 | 070324 | 106342 | 070230 | 074064 |
| | 074056 | 070270 | | | | | | |
| 001022 | 000 001 | 000022 | | | | | | |
| | 067752 | 073512 | 074040 | 073634 | 067766 | 073570 | 067526 | 110766 |
| | 000063 | | | | | | | |
| 001023 | 000 001 | 000024 | | | | | | |
| | 067772 | 070314 | 070304 | 073474 | 073364 | 070322 | 110766 | 000064 |
| | 070324 | 070304 | | | | | | |
| 001024 | 000 001 | 000024 | | | | | | |
| | 070014 | 073474 | 073364 | 070332 | 110766 | 000065 | 070314 | 070324 |
| | 106342 | 070230 | | | | | | |
| 001025 | 000 001 | 000020 | | | | | | |
| | 070036 | 074064 | 074056 | 070270 | 073512 | 074040 | 073634 | 070060 |
| 001026 | 000 001 | 000024 | | | | | | |
| | 070054 | 073570 | 067526 | 110766 | 000066 | 070324 | 070374 | 073516 |
| | 073364 | 070332 | | | | | | |
| 001027 | 000 001 | 000024 | | | | | | |
| | 070076 | 110766 | 000067 | 070314 | 070324 | 106342 | 070230 | 074064 |
| | 074056 | 070270 | | | | | | |
| 001030 | 000 001 | 000022 | | | | | | |
| | 070120 | 073512 | 074040 | 073634 | 070134 | 073570 | 067526 | 110766 |
| | 000070 | | | | | | | |
| 001031 | 000 001 | 000022 | | | | | | |
| | 070140 | 106244 | 110766 | 000071 | 070414 | 070304 | 073516 | 073364 |
| | 070422 | | | | | | | |
| 001032 | 000 001 | 000022 | | | | | | |
| | 070160 | 110766 | 000072 | 070414 | 070364 | 073512 | 074014 | 073634 |
| | 070202 | | | | | | | |
| 001033 | 000 001 | 000022 | | | | | | |
| | 070200 | 106244 | 110766 | 000073 | 070424 | 070344 | 073474 | 073364 |
| | 070432 | | | | | | | |
| 001034 | 000 001 | 000050 | | | | | | |
| | 070220 | 110766 | 000074 | 073570 | 067112 | 000000 | 100001 | 000000 |
| | 000000 | 017546 | 000010 | 000134 | 017546 | 000012 | 000134 | 017546 |
| | 000014 | 000134 | 017546 | 000016 | | | | |
| 001035 | 000 001 | 000050 | | | | | | |
| | 070266 | 000134 | 017546 | 000024 | 000134 | 017546 | 000026 | 000134 |
| | 012746 | 000001 | 000134 | 000001 | 016746 | 000002 | 000134 | 000000 |
| | 016746 | 000002 | 000134 | 000000 | | | | |
| 001036 | 000 001 | 000050 | | | | | | |
| | 070334 | 016746 | 000002 | 000134 | 000000 | 016746 | 000002 | 000134 |
| | 000000 | 016746 | 000002 | 000134 | 000000 | 012746 | 000000 | 000134 |
| | 000000 | 012746 | 000002 | 000134 | | | | |
| 001037 | 000 001 | 000034 | | | | | | |
| | 070402 | 000002 | 012746 | 000004 | 000134 | 000004 | 016746 | 000002 |
| | 000134 | 000000 | 016746 | 000002 | 000134 | 000000 | | |
| 001040 | 000 001 | 000050 | | | | | | |
| | 070434 | 004567 | 002630 | 000402 | 005016 | 012767 | 177777 | 073360 |
| | 012767 | 177777 | 073356 | 005067 | 073346 | 005067 | 073346 | 013500 |
| | 001412 | 100002 | 005400 | 000402 | | | | |
| 001041 | 000 001 | 000050 | | | | | | |
| | 070502 | 052700 | 100000 | 010067 | 073320 | 012767 | 000001 | 073310 |
| | 013500 | 001412 | 100002 | 005400 | 000402 | 052700 | 100000 | 010067 |
| | 073274 | 012767 | 000001 | 073264 | | | | |
| 001042 | 000 001 | 000044 | | | | | | |
| | 070550 | 032767 | 000001 | 073252 | 001774 | 032767 | 000001 | 073246 |
| | 001774 | 116716 | 073234 | 116766 | 073234 | 000001 | 042716 | 000401 |
| | 000167 | 002512 | | | | | | |
| 001043 | 000 001 | 000020 | | | | | | |
| | 070612 | 004567 | 002452 | 000401 | 005016 | 113516 | 000167 | 002474 |
| 001044 | 000 001 | 000050 | | | | | | |
| | 070630 | 004567 | 002434 | 000407 | 005067 | 000562 | 012567 | 000374 |
| | 005067 | 000122 | 013567 | 000440 | 013503 | 003002 | 012703 | 000001 |
| | 013504 | 003002 | 012704 | 000001 | | | | |
| 001045 | 000 001 | 000050 | | | | | | |
| | 070676 | 013501 | 012567 | 000204 | 012700 | 000406 | 160300 | 160400 |
| | 100004 | 012735 | 000100 | 000167 | 002376 | 010067 | 000050 | 010367 |
| | 000116 | 010467 | 000120 | 012567 | | | | |
| 001046 | 000 001 | 000050 | | | | | | |
| | 070744 | 000370 | 016700 | 000136 | 016704 | 000104 | 005020 | 005304 |
| | 001375 | 010146 | 010167 | 000240 | 012737 | 000000 | 176762 | 012767 |
| | 000000 | 000204 | 005267 | 000406 | | | | |

| | | | | | | | | |
|---|---|---|---|---|---|---|---|---|
| 001047 | 000 001 | 000050 | | | | | | |
| | 071012 | 012702 | 164010 | 012703 | 000004 | 012705 | 176772 | 012704 |
| | 176770 | 012767 | 000777 | 000044 | 012737 | 071344 | 000340 | 005037 |
| | 000342 | 012767 | 000000 | 000046 | | | | |
| 001050 | 000 001 | 000050 | | | | | | |
| | 071060 | 012767 | 000000 | 000104 | 011501 | 005014 | 105714 | 100376 |
| | 011501 | 012712 | 000140 | 000000 | 012700 | 000000 | 112714 | 000012 |
| | 105714 | 100376 | 011501 | 005327 | | | | |
| 001051 | 000 001 | 000050 | | | | | | |
| | 071126 | 000000 | 001372 | 105714 | 100376 | 011501 | 001004 | 052767 |
| | 000002 | 000254 | 000406 | 022701 | 001777 | 001003 | 052767 | 000004 |
| | 000236 | 060120 | 005327 | 000000 | | | | |
| 001052 | 000 001 | 000050 | | | | | | |
| | 071174 | 001356 | 005767 | 000012 | 001407 | 105714 | 100376 | 011501 |
| | 005327 | 000000 | 001372 | 105014 | 005767 | 000172 | 001375 | 005327 |
| | 000000 | 001261 | 012601 | 012700 | | | | |
| 001053 | 000 001 | 000050 | | | | | | |
| | 071242 | 000000 | 016703 | 177440 | 016704 | 177606 | 012337 | 177304 |
| | 010137 | 177300 | 012737 | 177776 | 177314 | 113720 | 177304 | 005304 |
| | 001365 | 062767 | 000002 | 177464 | | | | |
| 001054 | 000 001 | 000050 | | | | | | |
| | 071310 | 010067 | 177726 | 005327 | 000000 | 001402 | 000167 | 177420 |
| | 005037 | 176762 | 016737 | 000066 | 000000 | 000167 | 001760 | 105067 |
| | 177534 | 012737 | 071366 | 000340 | | | | |
| 001055 | 000 001 | 000050 | | | | | | |
| | 071356 | 012737 | 040040 | 164010 | 000002 | 005767 | 177534 | 001006 |
| | 005767 | 177572 | 001003 | 005767 | 177606 | 001403 | 052767 | 000001 |
| | 000006 | 005027 | 000000 | 000002 | | | | |
| 001056 | 000 001 | 000004 | | | | | | |
| | 071424 | 000000 | | | | | | |
| 001057 | 000 001 | 000030 | | | | | | |
| | 071426 | 004567 | 001636 | 000403 | 013500 | 012501 | 012502 | 112122 |
| | 005300 | 001375 | 000167 | 001650 | | | | |
| 001060 | 000 001 | 000050 | | | | | | |
| | 071454 | 012767 | 000405 | 000060 | 000413 | 012767 | 000403 | 000050 |
| | 000407 | 012767 | 000005 | 000040 | 000403 | 012767 | 000003 | 000030 |
| | 004567 | 001552 | 000403 | 004767 | | | | |
| 001061 | 000 001 | 000050 | | | | | | |
| | 071522 | 000050 | 004767 | 000100 | 013560 | 000014 | 012560 | 000012 |
| | 112760 | 000000 | 000016 | 010246 | 010046 | 104010 | 105767 | 177763 |
| | 001002 | 010046 | 104001 | 000167 | | | | |
| | 000 001 | 000050 | | | | | | |
| 001062 | 071570 | 001532 | 000000 | 013500 | 020027 | 000001 | 101373 | 006300 |
| | 016000 | 072262 | 010002 | 062702 | 000010 | 010001 | 062701 | 000022 |
| | 000207 | 005710 | 001003 | 010046 | | | | |
| 001063 | 000 001 | 000050 | | | | | | |
| | 071636 | 104006 | 000207 | 010046 | 104001 | 000207 | 004567 | 001414 |
| | 000402 | 004767 | 177712 | 012735 | 000001 | 012746 | 071566 | 010046 |
| | 104000 | 005745 | 005035 | 000731 | | | | |
| 001064 | 000 001 | 000050 | | | | | | |
| | 071704 | 004567 | 001360 | 000401 | 004767 | 177656 | 005710 | 001722 |
| | 004767 | 177702 | 010046 | 104007 | 000715 | 004567 | 001330 | 000402 |
| | 004767 | 177626 | 004767 | 177656 | | | | |
| 001065 | 000 001 | 000050 | | | | | | |
| | 071752 | 112711 | 000002 | 013502 | 010146 | 010046 | 104012 | 005302 |
| | 001373 | 000675 | 012767 | 000003 | 000030 | 000403 | 012767 | 000001 |
| | 000020 | 004567 | 001252 | 000401 | | | | |
| 001066 | 000 001 | 000050 | | | | | | |
| | 072020 | 004767 | 177550 | 004767 | 177600 | 112711 | 000000 | 010146 |
| | 010046 | 104012 | 000651 | 012767 | 000004 | 000030 | 000403 | 012767 |
| | 000005 | 000020 | 004567 | 001202 | | | | |
| 001067 | 000 001 | 000050 | | | | | | |
| | 072066 | 000402 | 004767 | 177500 | 004767 | 177530 | 112711 | 000000 |
| | 013561 | 000004 | 010146 | 010046 | 104012 | 000623 | 004567 | 001144 |
| | 000403 | 004767 | 177442 | 004767 | | | | |
| 001070 | 000 001 | 000050 | | | | | | |
| | 072134 | 177472 | 112711 | 000007 | 010146 | 010046 | 104012 | 016135 |
| | 000002 | 016203 | 000004 | 166203 | 000010 | 010335 | 000167 | 001132 |
| | 000000 | 000000 | 052176 | 000001 | | | | |
| 001071 | 000 001 | 000050 | | | | | | |
| | 072202 | 052140 | 000000 | 000000 | 000000 | 000000 | 000000 | 001400 |
| | 000000 | 000000 | 000000 | 000000 | 000000 | 052177 | 000401 | 052140 |
| | 000000 | 000000 | 000000 | 000000 | | | | |
| 001072 | 000 001 | 000020 | | | | | | |
| | 072250 | 000000 | 001400 | 000000 | 000000 | 000000 | 072174 | 072230 |
| 001073 | 000 001 | 000032 | | | | | | |
| | 072266 | 004567 | 000776 | 000403 | 012500 | 013501 | 003404 | 013503 |
| | 010320 | 005301 | 001375 | 000167 | 001006 | | | |
| 001074 | 000 001 | 000044 | | | | | | |
| | 072316 | 004567 | 000746 | 000401 | 013567 | 000024 | 004567 | 000024 |
| | 000402 | 072354 | 072356 | 022626 | 010146 | 010046 | 000167 | 000750 |
| | 000000 | 000001 | | | | | | |
| 001075 | 000 001 | 000050 | | | | | | |
| | 072360 | 004567 | 000704 | 000402 | 013504 | 013503 | 100422 | 020467 |
| | 000050 | 001020 | 004567 | 000252 | 000403 | 072540 | 072420 | 072422 |
| | 022727 | 000000 | 000120 | 003006 | | | | |
| 001076 | 000 001 | 000050 | | | | | | |

|         |                  |        |        |        |        |        |        |        |
|---------|------------------|--------|--------|--------|--------|--------|--------|--------|
|         |                  | 072426 | 022626 | 010146 | 010046 | 000167 | 000664 | 005403 | 010367 |
|         |                  | 177752 | 010427 | 000000 | 012746 | 072450 | 012746 | 072524 | 004467 |
|         |                  | 016262 | 076300 | 000000 | 000000 |        |        |        |        |
| 001077  | 000 001 000046   |        |        |        |        |        |        |        |
|         |                  | 072474 | 073470 | 072532 | 073470 | 000001 | 104214 | 103564 | 072512 |
|         |                  | 016703 | 177702 | 016704 | 177726 | 000727 | 036050 | 040460 | 024461 |
|         |                  | 072540 | 040001 | 000120 |        |        |        |        |        |
| 001100  | 000 001 000050   |        |        |        |        |        |        |        |
|         |                  | 072660 | 004567 | 000404 | 000403 | 005016 | 005066 | 000002 | 012504 |
|         |                  | 010467 | 000326 | 011567 | 000330 | 010403 | 063504 | 005304 | 063503 |
|         |                  | 005002 | 010467 | 000300 | 020403 |        |        |        |        |
| 001101  | 000 001 000050   |        |        |        |        |        |        |        |
|         |                  | 072726 | 103135 | 121427 | 000053 | 001423 | 121427 | 000055 | 001420 |
|         |                  | 121427 | 000056 | 001413 | 121427 | 000060 | 103403 | 121427 | 000071 |
|         |                  | 101406 | 005204 | 000753 | 005304 |        |        |        |        |
| 001102  | 000 001 000050   |        |        |        |        |        |        |        |
|         |                  | 072774 | 005002 | 000773 | 005202 | 005202 | 010401 | 005204 | 020403 |
|         |                  | 103062 | 121427 | 000105 | 001435 | 121427 | 000053 | 001443 | 121427 |
|         |                  | 000055 | 001440 | 121427 | 000060 |        |        |        |        |
| 001103  | 000 001 000050   |        |        |        |        |        |        |        |
|         |                  | 073042 | 103413 | 121427 | 000071 | 101010 | 052702 | 000001 | 032702 |
|         |                  | 000004 | 001751 | 052702 | 000010 | 000746 | 032702 | 000002 | 001030 |
|         |                  | 121427 | 000056 | 001025 | 052702 |        |        |        |        |
| 001104  | 000 001 000050   |        |        |        |        |        |        |        |
|         |                  | 073110 | 000002 | 000735 | 032702 | 000004 | 001017 | 032702 | 000001 |
|         |                  | 001722 | 052702 | 000006 | 000724 | 032702 | 000004 | 001406 | 032702 |
|         |                  | 000010 | 001003 | 052702 | 000010 |        |        |        |        |
| 001105  | 000 001 000050   |        |        |        |        |        |        |        |
|         |                  | 073156 | 000713 | 032702 | 000001 | 001702 | 010467 | 000032 | 010146 |
|         |                  | 010446 | 160116 | 005046 | 005046 | 004767 | 001240 | 012666 | 000006 |
|         |                  | 012666 | 000006 | 022626 | 012700 |        |        |        |        |
| 001106  | 000 001 000022   |        |        |        |        |        |        |        |
|         |                  | 073224 | 000000 | 162700 | 000000 | 005200 | 010037 | 000000 | 000167 |
|         |                  | 000060 |        |        |        |        |        |        |        |
| 001107  | 000 001 000026   |        |        |        |        |        |        |        |
|         |                  | 073244 | 004567 | 000020 | 000403 | 012546 | 013546 | 013546 | 004767 |
|         |                  | 000700 | 000167 | 000034 |        |        |        |        |        |
| 001110  | 000 001 000050   |        |        |        |        |        |        |        |
|         |                  | 073270 | 010446 | 010346 | 010246 | 010146 | 010046 | 010504 | 016605 |
|         |                  | 000012 | 022524 | 001001 | 000114 | 000167 | 000020 | 000205 | 012600 |
|         |                  | 012601 | 012602 | 012603 | 012604 |        |        |        |        |
| 001111  | 000 001 000006   |        |        |        |        |        |        |        |
|         |                  | 073336 | 012605 | 000205 |        |        |        |        |        |
| 001112  | 000 001 000024   |        |        |        |        |        |        |        |
|         |                  | 073342 | 010546 | 005046 | 010616 | 062716 | 000002 | 012746 | 001777 |
|         |                  | 000004 | 000777 |        |        |        |        |        |        |
| 001113  | 000 001 000006   |        |        |        |        |        |        |        |
|         |                  | 073364 | 012634 | 000134 |        |        |        |        |        |
| 001114  | 000 001 000022   |        |        |        |        |        |        |        |
|         |                  | 073370 | 012403 | 012623 | 012623 | 012623 | 012623 | 000134 | 012403 |
|         |                  | 000773 |        |        |        |        |        |        |        |
| 001115  | 000 001 000006   |        |        |        |        |        |        |        |
|         |                  | 073410 | 010634 | 000134 |        |        |        |        |        |
| 001116  | 000 001 000022   |        |        |        |        |        |        |        |
|         |                  | 073414 | 016046 | 000006 | 016046 | 000004 | 016046 | 000002 | 011046 |
|         |                  | 000134 |        |        |        |        |        |        |        |
| 001117  | 000 001 000014   |        |        |        |        |        |        |        |
|         |                  | 073434 | 012620 | 012620 | 012620 | 012620 | 000134 |        |        |
| 001120  | 000 001 000024   |        |        |        |        |        |        |        |
|         |                  | 073446 | 012446 | 000400 | 012403 | 060503 | 011303 | 012613 | 000134 |
|         |                  | 012600 | 000134 |        |        |        |        |        |        |
| 001121  | 000 001 000006   |        |        |        |        |        |        |        |
|         |                  | 073470 | 012446 | 000134 |        |        |        |        |        |
| 001122  | 000 001 000020   |        |        |        |        |        |        |        |
|         |                  | 073474 | 062616 | 102004 | 012700 | 006403 | 004767 | 015372 | 000134 |
| 001123  | 000 001 000006   |        |        |        |        |        |        |        |
|         |                  | 073512 | 162626 | 000134 |        |        |        |        |        |
| 001124  | 000 001 000020   |        |        |        |        |        |        |        |
|         |                  | 073516 | 162616 | 102004 | 012700 | 006403 | 004767 | 015350 | 000134 |
| 001125  | 000 001 000036   |        |        |        |        |        |        |        |
|         |                  | 073534 | 012600 | 020027 | 000001 | 103402 | 020014 | 101404 | 012400 |
|         |                  | 006300 | 060004 | 000134 | 006300 | 060004 | 011404 | 000134 |        |
| 001126  | 000 001 000006   |        |        |        |        |        |        |        |
|         |                  | 073570 | 011404 | 000134 |        |        |        |        |        |
| 001127  | 000 001 000042   |        |        |        |        |        |        |        |
|         |                  | 073574 | 012400 | 012401 | 060501 | 011120 | 012703 | 000003 | 001410 |
|         |                  | 005720 | 012401 | 100403 | 060501 | 017110 | 000000 | 005303 | 000767 |
|         |                  | 000134 |        |        |        |        |        |        |        |
| 001130  | 000 001 000016   |        |        |        |        |        |        |        |
|         |                  | 073634 | 005726 | 001402 | 005724 | 000134 | 011404 | 000134 |        |
| 001131  | 000 001 000006   |        |        |        |        |        |        |        |
|         |                  | 073650 | 010034 | 000134 |        |        |        |        |        |
| 001132  | 000 001 000040   |        |        |        |        |        |        |        |
|         |                  | 073654 | 063474 | 000000 | 102406 | 023434 | 003002 | 011404 | 000134 |
|         |                  | 005724 | 000134 | 022424 | 012700 | 015003 | 004767 | 015172 | 000770 |
| 001133  | 000 001 000050   |        |        |        |        |        |        |        |
|         |                  | 073712 | 004767 | 000034 | 010001 | 004767 | 000026 | 010002 | 004767 |
|         |                  | 000020 | 061112 | 102415 | 021210 | 003402 | 005724 | 000134 | 011404 |

|         |        |        |        |        |        |        |        |        |
|---------|--------|--------|--------|--------|--------|--------|--------|--------|
|         | 000134 | 012400 | 020027 | 000400 |        |        |        |        |
| 001134  | 000 001 | 000024 |        |        |        |        |        |        |
|         | 073760 | 101002 | 060500 | 011000 | 000207 | 012700 | 015003 | 004767 |
|         | 015102 | 000760 |        |        |        |        |        |        |
| 001135  | 000 001 | 000010 |        |        |        |        |        |        |
|         | 074002 | 005116 | 042616 | 000134 |        |        |        |        |
| 001136  | 000 001 | 000006 |        |        |        |        |        |        |
|         | 074010 | 052616 | 000134 |        |        |        |        |        |
| 001137  | 000 001 | 000036 |        |        |        |        |        |        |
|         | 074014 | 001404 | 002403 | 005046 | 000134 | 001375 | 012746 | 177777 |
|         | 000134 | 003374 | 000770 | 002372 | 000766 | 001370 | 000764 |        |
| 001140  | 000 001 | 000016 |        |        |        |        |        |        |
|         | 074050 | 105066 | 000001 | 000134 | 112600 | 010046 | 000134 |        |
| 001141  | 000 001 | 000022 |        |        |        |        |        |        |
|         | 074064 | 111046 | 000134 | 112620 | 000134 | 110046 | 000134 | 112634 |
|         | 000134 |        |        |        |        |        |        |        |
| 001142  | 000 001 | 000050 |        |        |        |        |        |        |
|         | 074104 | 105416 | 000134 | 005416 | 102414 | 000134 | 005766 | 000004 |
|         | 001403 | 062766 | 100000 | 000004 | 005716 | 001402 | 062716 | 100000 |
|         | 000134 | 012700 | 005403 | 004767 |        |        |        |        |
| 001143  | 000 001 | 000006 |        |        |        |        |        |        |
|         | 074152 | 014726 | 000134 |        |        |        |        |        |
| 001144  | 000 001 | 000050 |        |        |        |        |        |        |
|         | 074156 | 012700 | 000166 | 000402 | 012700 | 000154 | 010446 | 016603 |
|         | 000010 | 016602 | 000006 | 002003 | 005002 | 005066 | 000006 | 016604 |
|         | 000004 | 012746 | 000040 | 020027 |        |        |        |        |
| 001145  | 000 001 | 000050 |        |        |        |        |        |        |
|         | 074224 | 000166 | 001405 | 005704 | 002003 | 005404 | 012716 | 000055 |
|         | 005046 | 060700 | 005710 | 001416 | 005001 | 161004 | 103402 | 005201 |
|         | 000774 | 062004 | 005701 | 001002 |        |        |        |        |
| 001146  | 000 001 | 000050 |        |        |        |        |        |        |
|         | 074272 | 005716 | 001764 | 062701 | 000060 | 010146 | 000760 | 060203 |
|         | 062704 | 000060 | 110443 | 005302 | 003410 | 112643 | 001374 | 112613 |
|         | 005302 | 001410 | 112743 | 000040 |        |        |        |        |
| 001147  | 000 001 | 000050 |        |        |        |        |        |        |
|         | 074340 | 000773 | 005726 | 001011 | 022726 | 000040 | 001011 | 012604 |
|         | 012664 | 000004 | 005726 | 006126 | 000207 | 005726 | 001376 | 005726 |
|         | 016603 | 000010 | 112723 | 000052 |        |        |        |        |
| 001150  | 000 001 | 000044 |        |        |        |        |        |        |
|         | 074406 | 005366 | 000006 | 003373 | 005166 | 000006 | 000755 | 023420 |
|         | 001750 | 000144 | 000012 | 000000 | 100000 | 010000 | 001000 | 000100 |
|         | 000010 | 000000 |        |        |        |        |        |        |
| 001151  | 000 001 | 000050 |        |        |        |        |        |        |
|         | 074450 | 005046 | 010046 | 010146 | 010246 | 010346 | 010446 | 010546 |
|         | 005046 | 005046 | 005046 | 012746 | 000101 | 012746 | 000022 | 005046 |
|         | 005046 | 016605 | 000044 | 066666 |        |        |        |        |
| 001152  | 000 001 | 000050 |        |        |        |        |        |        |
|         | 074516 | 000042 | 000044 | 005000 | 005001 | 005002 | 005003 | 112504 |
|         | 042704 | 177600 | 120427 | 000040 | 001005 | 020566 | 000044 | 103767 |
|         | 000167 | 000326 | 120427 | 000053 |        |        |        |        |
| 001153  | 000 001 | 000050 |        |        |        |        |        |        |
|         | 074564 | 001455 | 120427 | 000055 | 001013 | 005266 | 000012 | 000447 |
|         | 112504 | 042704 | 177600 | 120427 | 000040 | 001002 | 012704 | 000060 |
|         | 120427 | 000060 | 002514 | 001010 |        |        |        |        |
| 001154  | 000 001 | 000050 |        |        |        |        |        |        |
|         | 074632 | 005700 | 001006 | 005701 | 001004 | 005702 | 001002 | 005703 |
|         | 001423 | 120427 | 000071 | 003121 | 005366 | 000004 | 002003 | 005266 |
|         | 000014 | 000412 | 162704 | 000060 |        |        |        |        |
| 001155  | 000 001 | 000050 |        |        |        |        |        |        |
|         | 074700 | 004767 | 001004 | 004767 | 001046 | 060403 | 005502 | 005501 |
|         | 005500 | 020566 | 000044 | 103726 | 010516 | 005700 | 001006 | 005701 |
|         | 001004 | 005702 | 001002 | 005703 |        |        |        |        |
| 001156  | 000 001 | 000050 |        |        |        |        |        |        |
|         | 074746 | 001457 | 021605 | 001003 | 166666 | 000036 | 000014 | 005766 |
|         | 000002 | 001002 | 016616 | 000040 | 166616 | 000002 | 161666 | 000014 |
|         | 003003 | 002543 | 000167 | 000446 |        |        |        |        |
| 001157  | 000 001 | 000050 |        |        |        |        |        |        |
|         | 075014 | 020027 | 031462 | 101011 | 004767 | 000662 | 005266 | 000006 |
|         | 005366 | 000014 | 003366 | 000167 | 000416 | 004767 | 000572 | 062766 |
|         | 000003 | 000006 | 000765 | 120427 |        |        |        |        |
| 001160  | 000 001 | 000050 |        |        |        |        |        |        |
|         | 075062 | 000056 | 001006 | 005766 | 000002 | 001003 | 010566 | 000002 |
|         | 000707 | 105166 | 000033 | 005000 | 005001 | 005002 | 005003 | 000167 |
|         | 000450 | 120427 | 000105 | 001403 |        |        |        |        |
| 001161  | 000 001 | 000050 |        |        |        |        |        |        |
|         | 075130 | 120427 | 000104 | 001362 | 010516 | 005316 | 010366 | 000042 |
|         | 005003 | 020566 | 000044 | 103352 | 112504 | 042704 | 177600 | 120427 |
|         | 000053 | 001405 | 120427 | 000055 |        |        |        |        |
| 001162  | 000 001 | 000050 |        |        |        |        |        |        |
|         | 075176 | 001010 | 005266 | 000010 | 020566 | 000044 | 103334 | 112504 |
|         | 042704 | 177600 | 120427 | 000040 | 001002 | 012704 | 000060 | 120427 |
|         | 000060 | 002721 | 120427 | 000071 |        |        |        |        |
| 001163  | 000 001 | 000050 |        |        |        |        |        |        |
|         | 075244 | 003316 | 162704 | 000060 | 006303 | 060304 | 006303 | 006303 |
|         | 060403 | 020566 | 000044 | 103750 | 005766 | 000010 | 001401 | 005403 |
|         | 060366 | 000014 | 016603 | 000042 |        |        |        |        |

| | | | | | | | | |
|---|---|---|---|---|---|---|---|---|
| 001164 | 000 001 | 000050 | | | | | | |
| | 075312 | 000167 | 177412 | 005700 | 002405 | 005366 | 000006 | 004767 |
| | 000424 | 100373 | 012704 | 000020 | 004767 | 000424 | 010346 | 010246 |
| | 010146 | 010046 | 004767 | 000410 | | | | |
| 001165 | 000 001 | 000050 | | | | | | |
| | 075360 | 000241 | 004767 | 000402 | 012705 | 000002 | 000241 | 004767 |
| | 000370 | 066603 | 000006 | 005502 | 005501 | 005500 | 066602 | 000004 |
| | 005501 | 005500 | 066601 | 000002 | | | | |
| 001166 | 000 001 | 000050 | | | | | | |
| | 075426 | 005500 | 061600 | 005305 | 003357 | 005304 | 003345 | 062706 |
| | 000010 | 162766 | 000003 | 000006 | 005266 | 000014 | 002716 | 005366 |
| | 000006 | 004767 | 000264 | 103373 | | | | |
| 001167 | 000 001 | 000050 | | | | | | |
| | 075474 | 062766 | 000200 | 000006 | 003455 | 026627 | 000006 | 000377 |
| | 003051 | 105003 | 150203 | 000303 | 105002 | 150102 | 000302 | 105001 |
| | 150001 | 000301 | 105000 | 156600 | | | | |
| 001170 | 000 001 | 000050 | | | | | | |
| | 075542 | 000006 | 000300 | 006066 | 000012 | 004767 | 000212 | 005503 |
| | 005502 | 005501 | 005500 | 102423 | 103422 | 010066 | 000036 | 010166 |
| | 000040 | 010266 | 000042 | 010366 | | | | |
| 001171 | 000 001 | 000050 | | | | | | |
| | 075610 | 000044 | 062706 | 000016 | 012605 | 012604 | 012603 | 012602 |
| | 012601 | 012600 | 006126 | 000207 | 000167 | 177240 | 020027 | 146314 |
| | 103405 | 000241 | 004767 | 000112 | | | | |
| 001172 | 000 001 | 000050 | | | | | | |
| | 075656 | 005266 | 000010 | 010046 | 010146 | 010246 | 010346 | 000241 |
| | 004767 | 000070 | 000241 | 004767 | 000062 | 000410 | 010046 | 010146 |
| | 010246 | 010346 | 004767 | 000032 | | | | |
| 001173 | 000 001 | 000050 | | | | | | |
| | 075724 | 004767 | 000026 | 062603 | 005502 | 005501 | 005500 | 062602 |
| | 005501 | 005500 | 062601 | 005500 | 062600 | 000207 | 006303 | 006102 |
| | 006101 | 006100 | 000207 | 006000 | | | | |
| 001174 | 000 001 | 000012 | | | | | | |
| | 075772 | 006001 | 006002 | 006003 | 000207 | | | |
| 001175 | 000 001 | 000050 | | | | | | |
| | 076002 | 012746 | 000001 | 000404 | 005046 | 000402 | 012746 | 177777 |
| | 012762 | 076156 | 177776 | 005764 | 000036 | 002454 | 001003 | 105062 |
| | 000030 | 000403 | 112762 | 000001 | | | | |
| 001176 | 000 001 | 000050 | | | | | | |
| | 076050 | 000030 | 010246 | 062716 | 000026 | 010246 | 005766 | 000004 |
| | 001402 | 104004 | 000401 | 104002 | 010246 | 104001 | 005003 | 105762 |
| | 000031 | 001420 | 005203 | 132762 | | | | |
| 001177 | 000 001 | 000050 | | | | | | |
| | 076116 | 000040 | 000031 | 001013 | 005203 | 132762 | 000006 | 000031 |
| | 001006 | 005203 | 132762 | 000100 | 000031 | 001401 | 005203 | 005726 |
| | 000207 | 012703 | 177777 | 000207 | | | | |
| 001200 | 000 001 | 000050 | | | | | | |
| | 076164 | 012762 | 000004 | 000026 | 005716 | 002405 | 001402 | 006262 |
| | 000026 | 006262 | 000026 | 010246 | 062716 | 000026 | 010246 | 104011 |
| | 010246 | 104001 | 005003 | 105762 | | | | |
| 001201 | 000 001 | 000050 | | | | | | |
| | 076232 | 000027 | 001746 | 005203 | 132762 | 000200 | 000027 | 001341 |
| | 005203 | 132762 | 000100 | 000027 | 001334 | 005203 | 132762 | 000010 |
| | 000027 | 001727 | 005203 | 000725 | | | | |
| 001202 | 000 001 | 000050 | | | | | | |
| | 076300 | 012746 | 000001 | 000401 | 005046 | 012746 | 076366 | 005046 |
| | 012746 | 101640 | 005766 | 000006 | 001002 | 012716 | 101640 | 004767 |
| | 005560 | 012705 | 000044 | 006205 | | | | |
| 001203 | 000 001 | 000022 | | | | | | |
| | 076346 | 005046 | 005305 | 001375 | 010605 | 012746 | 000046 | 000167 |
| | 005600 | | | | | | | |
| 001204 | 000 001 | 000050 | | | | | | |
| | 076366 | 005765 | 000042 | 001402 | 000167 | 003070 | 016465 | 000044 |
| | 000042 | 117565 | 000042 | 000012 | 122765 | 000050 | 000012 | 001002 |
| | 000167 | 001332 | 000167 | 001766 | | | | |
| 001205 | 000 001 | 000050 | | | | | | |
| | 076434 | 005000 | 005365 | 000020 | 005065 | 000022 | 004767 | 000240 |
| | 122701 | 000074 | 001014 | 004767 | 000134 | 005700 | 002003 | 005365 |
| | 000022 | 000446 | 005265 | 000022 | | | | |
| 001206 | 000 001 | 000050 | | | | | | |
| | 076502 | 000443 | 004767 | 000202 | 005765 | 000022 | 001006 | 122701 |
| | 000055 | 001003 | 005365 | 000022 | 000765 | 162701 | 000060 | 100416 |
| | 022701 | 000011 | 002413 | 005765 | | | | |
| 001207 | 000 001 | 000050 | | | | | | |
| | 076550 | 000022 | 001002 | 005265 | 000022 | 006300 | 060001 | 006300 |
| | 006300 | 060100 | 000744 | 117565 | 000042 | 000012 | 005765 | 000022 |
| | 002001 | 005400 | 010065 | 000020 | | | | |
| 001210 | 000 001 | 000050 | | | | | | |
| | 076616 | 000207 | 010446 | 010546 | 016503 | 000042 | 005203 | 005203 |
| | 042703 | 000001 | 016405 | 000000 | 010304 | 000134 | 012600 | 012605 |
| | 010465 | 000042 | 004767 | 000022 | | | | |
| 001211 | 000 001 | 000050 | | | | | | |
| | 076664 | 012604 | 000207 | 005265 | 000042 | 117501 | 000042 | 110165 |
| | 000012 | 000207 | 005365 | 000042 | 004767 | 177752 | 122701 | 000040 |
| | 001773 | 000207 | 012700 | 000005 | | | | |
| 001212 | 000 001 | 000050 | | | | | | |

|        |        |        |        |        |        |        |        |        |
|--------|--------|--------|--------|--------|--------|--------|--------|--------|
|        | 076732 | 000402 | 012700 | 000022 | 005001 | 126561 | 000012 | 077056 |
|        | 001405 | 005201 | 020100 | 002771 | 000167 | 001436 | 006301 | 000171 |
|        | 077012 | 012701 | 000002 | 012700 |        |        |        |        |
| 001213 | 000 001 000040 |  |  |  |  |  |  |  |
|        | 077000 | 000022 | 000757 | 012701 | 000001 | 000772 | 077210 | 100120 |
|        | 077560 | 077262 | 077630 | 077762 | 100504 | 100430 | 100450 | 100450 |
| 001214 | 000 001 000050 |  |  |  |  |  |  |  |
|        | 077036 | 100450 | 100464 | 100520 | 100464 | 077454 | 077232 | 077374 |
|        | 077100 | 024454 | 052057 | 024047 | 042101 | 043105 | 044507 | 047514 |
|        | 050110 | 050530 | 005764 | 000042 |  |  |  |  |
| 001215 | 000 001 000050 |  |  |  |  |  |  |  |
|        | 077104 | 001003 | 004767 | 177556 | 000705 | 005765 | 000022 | 001402 |
|        | 000167 | 001274 | 005764 | 000024 | 001002 | 000167 | 001070 | 022764 |
|        | 000002 | 000022 | 001404 | 012700 |        |        |        |        |
| 001216 | 000 001 000050 |  |  |  |  |  |  |  |
|        | 077152 | 000006 | 004767 | 011722 | 016400 | 000026 | 166400 | 000032 |
|        | 010074 | 000024 | 004767 | 177470 | 012765 | 000001 | 000010 | 000207 |
|        | 005765 | 000022 | 001402 | 000167 |        |        |        |        |
| 001217 | 000 001 000050 |  |  |  |  |  |  |  |
|        | 077220 | 001200 | 004767 | 177206 | 000167 | 177540 | 005765 | 000022 |
|        | 001002 | 000167 | 001156 | 016565 | 000020 | 000002 | 004767 | 177156 |
|        | 000167 | 177452 | 005765 | 000022 |        |        |        |        |
| 001220 | 000 001 000050 |  |  |  |  |  |  |  |
|        | 077266 | 001402 | 000167 | 001126 | 004767 | 177134 | 005765 | 000020 |
|        | 003423 | 005365 | 000020 | 066465 | 000032 | 000020 | 026465 | 000030 |
|        | 000000 | 101403 | 016465 | 000030 |        |        |        |        |
| 001221 | 000 001 000050 |  |  |  |  |  |  |  |
|        | 077334 | 000000 | 016564 | 000020 | 000030 | 026464 | 000030 | 000026 |
|        | 103402 | 000167 | 001034 | 005065 | 000020 | 005065 | 000022 | 000167 |
|        | 177332 | 005765 | 000022 | 001403 |        |        |        |        |
| 001222 | 000 001 000050 |  |  |  |  |  |  |  |
|        | 077402 | 003004 | 000167 | 001012 | 005265 | 000020 | 005765 | 000020 |
|        | 001771 | 066564 | 000020 | 000030 | 026464 | 000030 | 000026 | 101402 |
|        | 000167 | 000750 | 004767 | 176764 |        |        |        |        |
| 001223 | 000 001 000050 |  |  |  |  |  |  |  |
|        | 077450 | 000167 | 177260 | 005765 | 000020 | 003002 | 000167 | 000734 |
|        | 016400 | 000030 | 016501 | 000042 | 016502 | 000020 | 060264 | 000030 |
|        | 026464 | 000030 | 000026 | 101402 |        |        |        |        |
| 001224 | 000 001 000050 |  |  |  |  |  |  |  |
|        | 077516 | 000167 | 000672 | 005201 | 005764 | 000042 | 001402 | 112011 |
|        | 000401 | 111120 | 005302 | 001367 | 010165 | 000042 | 004767 | 176660 |
|        | 000167 | 177154 | 005765 | 000022 |        |        |        |        |
| 001225 | 000 001 000050 |  |  |  |  |  |  |  |
|        | 077564 | 001402 | 000167 | 000630 | 026465 | 000030 | 000000 | 103005 |
|        | 016564 | 000000 | 000030 | 005065 | 000000 | 004774 | 000034 | 004767 |
|        | 176610 | 000167 | 177104 | 005765 |        |        |        |        |
| 001226 | 000 001 000050 |  |  |  |  |  |  |  |
|        | 077632 | 000022 | 001402 | 000167 | 000560 | 016400 | 000030 | 016501 |
|        | 000042 | 005201 | 122711 | 000047 | 001414 | 020064 | 000026 | 103402 |
|        | 000167 | 000520 | 005764 | 000042 |        |        |        |        |
| 001227 | 000 001 000050 |  |  |  |  |  |  |  |
|        | 077700 | 001402 | 112011 | 000762 | 111120 | 000760 | 122761 | 000047 |
|        | 000001 | 001010 | 005764 | 000042 | 001002 | 005201 | 000753 | 105061 |
|        | 000001 | 000750 | 010165 | 000042 |        |        |        |        |
| 001230 | 000 001 000050 |  |  |  |  |  |  |  |
|        | 077746 | 010064 | 000030 | 004767 | 176456 | 000167 | 176752 | 005765 |
|        | 000022 | 001403 | 003004 | 000167 | 000424 | 005265 | 000020 | 005765 |
|        | 000020 | 001771 | 005765 | 000040 |        |        |        |        |
| 001231 | 000 001 000050 |  |  |  |  |  |  |  |
|        | 100014 | 001417 | 022765 | 000002 | 000040 | 101005 | 001425 | 012700 |
|        | 000402 | 000167 | 000342 | 016565 | 000042 | 000036 | 016565 | 000020 |
|        | 000030 | 005265 | 000024 | 016565 |        |        |        |        |
| 001232 | 000 001 000050 |  |  |  |  |  |  |  |
|        | 100062 | 000020 | 000032 | 005265 | 000040 | 004767 | 176336 | 000167 |
|        | 176702 | 016565 | 000042 | 000034 | 016565 | 000032 | 000026 | 000760 |
|        | 005765 | 000022 | 001402 | 000167 |        |        |        |        |
| 001233 | 000 001 000050 |  |  |  |  |  |  |  |
|        | 100130 | 000270 | 022765 | 000002 | 000040 | 101030 | 001420 | 005365 |
|        | 000032 | 001407 | 016565 | 000034 | 000042 | 004767 | 176250 | 000167 |
|        | 176544 | 016565 | 000026 | 000032 |        |        |        |        |
| 001234 | 000 001 000050 |  |  |  |  |  |  |  |
|        | 100176 | 005365 | 000040 | 000766 | 005365 | 000032 | 001772 | 016565 |
|        | 000036 | 000042 | 000757 | 005764 | 000024 | 001020 | 005764 | 000042 |
|        | 001013 | 026465 | 000030 | 000000 |        |        |        |        |
| 001235 | 000 001 000050 |  |  |  |  |  |  |  |
|        | 100244 | 103005 | 016564 | 000000 | 000030 | 005065 | 000000 | 004774 |
|        | 000034 | 000167 | 000110 | 005765 | 000024 | 001404 | 012700 | 000002 |
|        | 000167 | 000074 | 026465 | 000030 |        |        |        |        |
| 001236 | 000 001 000050 |  |  |  |  |  |  |  |
|        | 100312 | 000000 | 103005 | 016564 | 000000 | 000030 | 005065 | 000000 |
|        | 004774 | 000034 | 005765 | 000036 | 001006 | 016465 | 000044 | 000042 |
|        | 005265 | 000024 | 000701 | 016565 |        |        |        |        |
| 001237 | 000 001 000050 |  |  |  |  |  |  |  |
|        | 100360 | 000030 | 000032 | 016565 | 000034 | 000042 | 005265 | 000040 |
|        | 000764 | 000207 | 004767 | 010474 | 005264 | 000014 | 000207 | 012700 |
|        | 001402 | 000770 | 012700 | 001002 |        |        |        |        |
| 001240 | 000 001 000050 |  |  |  |  |  |  |  |
|        | 100426 | 000765 | 012746 | 000031 | 012746 | 000020 | 005046 | 012702 |

|        |        |        |        |        |        |        |        |        |
|--------|--------|--------|--------|--------|--------|--------|--------|--------|
|        | 000001 | 000432 | 012746 | 000017 | 012746 | 000007 | 012746 | 177777 |
|        | 000766 | 012746 | 000007 | 005046 |        |        |        |        |
| 001241 | 000 001 | 000050 |       |        |        |        |        |        |
|        | 100474 | 012746 | 000001 | 005002 | 000414 | 012746 | 000010 | 005046 |
|        | 012746 | 000002 | 000770 | 012746 | 000002 | 005046 | 012746 | 000003 |
|        | 000762 | 012665 | 000016 | 012665 |        |        |        |        |
| 001242 | 000 001 | 000050 |       |        |        |        |        |        |
|        | 100542 | 000004 | 012665 | 000006 | 005764 | 000042 | 001402 | 062701 |
|        | 000020 | 162701 | 000014 | 016165 | 100710 | 000014 | 005765 | 000022 |
|        | 001403 | 003004 | 000167 | 177612 |        |        |        |        |
| 001243 | 000 001 | 000050 |       |        |        |        |        |        |
|        | 100610 | 005265 | 000020 | 016565 | 000020 | 000010 | 001770 | 004767 |
|        | 175604 | 005765 | 000022 | 002763 | 001422 | 016565 | 000020 | 000006 |
|        | 001756 | 005702 | 001414 | 022765 |        |        |        |        |
| 001244 | 000 001 | 000050 |       |        |        |        |        |        |
|        | 100656 | 000056 | 000012 | 001350 | 004767 | 175544 | 005765 | 000022 |
|        | 003743 | 016565 | 000020 | 000004 | 000167 | 000040 | 101522 | 111014 |
|        | 111014 | 111014 | 111014 | 074164 |        |        |        |        |
| 001245 | 000 001 | 000020 |       |        |        |        |        |        |
|        | 100724 | 111000 | 074156 | 101564 | 074450 | 074450 | 074450 | 074450 |
| 001246 | 000 001 | 000050 |       |        |        |        |        |        |
|        | 100742 | 111030 | 111044 | 111030 | 005764 | 000024 | 001002 | 000167 |
|        | 177246 | 016446 | 000030 | 005764 | 000042 | 001461 | 011600 | 005001 |
|        | 022765 | 000002 | 000016 | 001442 |        |        |        |        |
| 001247 | 000 001 | 000050 |       |        |        |        |        |        |
|        | 101010 | 026501 | 000006 | 001450 | 026400 | 000026 | 101406 | 122710 |
|        | 000054 | 001403 | 005201 | 005200 | 000764 | 005701 | 001414 | 010146 |
|        | 005201 | 060164 | 000030 | 026464 |        |        |        |        |
| 001250 | 000 001 | 000050 |       |        |        |        |        |        |
|        | 101054 | 000026 | 000030 | 101003 | 016464 | 000026 | 000030 | 000433 |
|        | 012716 | 101112 | 012746 | 000001 | 005264 | 000030 | 000761 | 020040 |
|        | 026501 | 000006 | 001406 | 026400 |        |        |        |        |
| 001251 | 000 001 | 000050 |       |        |        |        |        |        |
|        | 101124 | 000026 | 101744 | 005200 | 005201 | 000767 | 016546 | 000006 |
|        | 061664 | 000030 | 026464 | 000030 | 000026 | 101402 | 000167 | 177232 |
|        | 005765 | 000016 | 003004 | 016546 |        |        |        |        |
| 001252 | 000 001 | 000050 |       |        |        |        |        |        |
|        | 101172 | 000004 | 016546 | 000002 | 005764 | 000042 | 001046 | 012700 |
|        | 000002 | 005765 | 000016 | 003007 | 026427 | 000022 | 000010 | 001413 |
|        | 005046 | 005046 | 000411 | 020065 |        |        |        |        |
| 001253 | 000 001 | 000050 |       |        |        |        |        |        |
|        | 101240 | 000016 | 101007 | 001526 | 117400 | 000024 | 010046 | 000422 |
|        | 006300 | 006300 | 016401 | 000024 | 060001 | 006200 | 005746 | 114166 |
|        | 000001 | 114116 | 005300 | 001372 |        |        |        |        |
| 001254 | 000 001 | 000050 |       |        |        |        |        |        |
|        | 101306 | 026427 | 000020 | 000001 | 001002 | 105066 | 000001 | 004775 |
|        | 000014 | 006003 | 005764 | 000042 | 001446 | 012700 | 000002 | 005765 |
|        | 000016 | 003022 | 026427 | 000022 |        |        |        |        |
| 001255 | 000 001 | 000050 |       |        |        |        |        |        |
|        | 101354 | 000010 | 001424 | 006166 | 000004 | 012602 | 010266 | 000002 |
|        | 012402 | 010266 | 000002 | 005564 | 000002 | 005516 | 102423 | 103422 |
|        | 000407 | 020064 | 000020 | 101405 |        |        |        |        |
| 001256 | 000 001 | 000050 |       |        |        |        |        |        |
|        | 101422 | 112674 | 000024 | 000411 | 006300 | 006300 | 016401 | 000024 |
|        | 010602 | 112221 | 005300 | 001375 | 010206 | 006103 | 103004 | 012700 |
|        | 000006 | 004767 | 007414 | 000207 |        |        |        |        |
| 001257 | 000 001 | 000050 |       |        |        |        |        |        |
|        | 101470 | 005365 | 000010 | 001402 | 000167 | 177246 | 005065 | 000024 |
|        | 005065 | 000022 | 005065 | 000020 | 000167 | 175204 | 016401 | 000024 |
|        | 012602 | 012600 | 016403 | 000020 |        |        |        |        |
| 001260 | 000 001 | 000050 |       |        |        |        |        |        |
|        | 101536 | 020302 | 103003 | 060200 | 160300 | 010302 | 112120 | 005302 |
|        | 001375 | 005003 | 000167 | 177666 | 005726 | 012602 | 012601 | 016400 |
|        | 000024 | 016403 | 000020 | 020302 |        |        |        |        |
| 001261 | 000 001 | 000036 |       |        |        |        |        |        |
|        | 101604 | 001761 | 101004 | 060201 | 160301 | 010302 | 000754 | 060300 |
|        | 160203 | 112740 | 000040 | 005303 | 001374 | 160200 | 000744 |        |
| 001262 | 000 001 | 000050 |       |        |        |        |        |        |
|        | 101640 | 017400 | 000046 | 004767 | 011334 | 005701 | 001004 | 012703 |
|        | 000014 | 000167 | 002142 | 004767 | 010766 | 005764 | 000032 | 001162 |
|        | 132761 | 000003 | 000015 | 001014 |        |        |        |        |
| 001263 | 000 001 | 000050 |       |        |        |        |        |        |
|        | 101706 | 004767 | 011476 | 004767 | 003616 | 005703 | 001406 | 005703 |
|        | 002402 | 062703 | 000003 | 000167 | 002070 | 132761 | 000002 | 000015 |
|        | 001404 | 012703 | 000013 | 000167 |        |        |        |        |
| 001264 | 000 001 | 000050 |       |        |        |        |        |        |
|        | 101754 | 002050 | 122761 | 000004 | 000004 | 001014 | 005764 | 000042 |
|        | 001060 | 016162 | 000000 | 000000 | 004767 | 011244 | 005703 | 001736 |
|        | 000167 | 002010 | 005764 | 000042 |        |        |        |        |
| 001265 | 000 001 | 000050 |       |        |        |        |        |        |
|        | 102022 | 001364 | 012700 | 000210 | 016162 | 000000 | 000000 | 010203 |
|        | 062703 | 000034 | 010346 | 112723 | 000040 | 005300 | 001374 | 012700 |
|        | 000205 | 010246 | 104013 | 005726 |        |        |        |        |
| 001266 | 000 001 | 000050 |       |        |        |        |        |        |
|        | 102070 | 012703 | 102566 | 005713 | 001404 | 022316 | 001374 | 005266 |
|        | 000004 | 022626 | 012603 | 010364 | 000032 | 010364 | 000030 | 060003 |
|        | 010364 | 000026 | 000207 | 016162 |        |        |        |        |
| 001267 | 000 001 | 000050 |       |        |        |        |        |        |

|        |        |        |        |        |        |        |        |        |
|--------|--------|--------|--------|--------|--------|--------|--------|--------|
|        | 102136 | 000000 | 000000 | 012762 | 000210 | 000026 | 004767 | 173640 |
|        | 005703 | 001402 | 000167 | 001642 | 005261 | 000020 | 062702 | 000034 |
|        | 010201 | 066202 | 177776 | 005302 |        |        |        |        |
| 001270 | 000 001 | 000050 |        |        |        |        |        |        |
|        | 102204 | 010103 | 122712 | 000011 | 101007 | 122712 | 000015 | 103404 |
|        | 005302 | 122712 | 000015 | 001401 | 005202 | 010200 | 160300 | 000725 |
|        | 005764 | 000042 | 001332 | 016162 |        |        |        |        |
| 001271 | 000 001 | 000050 |        |        |        |        |        |        |
|        | 102252 | 000000 | 000000 | 012762 | 000210 | 000026 | 010246 | 104013 |
|        | 005726 | 012616 | 012703 | 102566 | 005713 | 001404 | 022316 | 001374 |
|        | 005726 | 000430 | 005726 | 112774 |        |        |        |        |
| 001272 | 000 001 | 000050 |        |        |        |        |        |        |
|        | 102320 | 000015 | 000030 | 005264 | 000030 | 112774 | 000012 | 000030 |
|        | 166464 | 000032 | 000030 | 005264 | 000030 | 016462 | 000030 | 000032 |
|        | 004767 | 173426 | 005703 | 001076 |        |        |        |        |
| 001273 | 000 001 | 000050 |        |        |        |        |        |        |
|        | 102366 | 005261 | 000020 | 000614 | 112774 | 000015 | 000030 | 005264 |
|        | 000030 | 112774 | 000013 | 000030 | 105062 | 000034 | 126227 | 000035 |
|        | 000053 | 001005 | 005062 | 000034 |        |        |        |        |
| 001274 | 000 001 | 000050 |        |        |        |        |        |        |
|        | 102434 | 005364 | 000032 | 000736 | 126227 | 000035 | 000061 | 001004 |
|        | 012762 | 006015 | 000034 | 000430 | 126227 | 000035 | 000044 | 001005 |
|        | 005364 | 000030 | 112774 | 000013 |        |        |        |        |
| 001275 | 000 001 | 000050 |        |        |        |        |        |        |
|        | 102502 | 000030 | 116203 | 000035 | 012762 | 005015 | 000034 | 120327 |
|        | 000060 | 001007 | 012762 | 000002 | 000032 | 004767 | 173252 | 005703 |
|        | 001010 | 012762 | 000002 | 000032 |        |        |        |        |
| 001276 | 000 001 | 000020 |        |        |        |        |        |        |
|        | 102550 | 004767 | 173234 | 005703 | 001001 | 000723 | 000167 | 001240 |
| 001277 | 000 001 | 000022 |        |        |        |        |        |        |
|        | 102566 | 046600 | 042420 | 100040 | 046636 | 046637 | 046601 | 046602 |
|        | 000000 |        |        |        |        |        |        |        |
| 001300 | 000 001 | 000050 |        |        |        |        |        |        |
|        | 102606 | 012746 | 000001 | 000401 | 005046 | 012746 | 102676 | 012746 |
|        | 177777 | 012746 | 103044 | 005766 | 000006 | 001002 | 012716 | 103044 |
|        | 004767 | 001250 | 012705 | 000006 |        |        |        |        |
| 001301 | 000 001 | 000024 |        |        |        |        |        |        |
|        | 102654 | 004205 | 005046 | 005305 | 001375 | 010605 | 012746 | 000010 |
|        | 000167 | 001270 |        |        |        |        |        |        |
| 001302 | 000 001 | 000050 |        |        |        |        |        |        |
|        | 102676 | 016400 | 000020 | 016401 | 000024 | 016402 | 000030 | 010203 |
|        | 005764 | 000042 | 001002 | 010102 | 010301 | 020364 | 000026 | 103424 |
|        | 005765 | 000002 | 001432 | 010046 |        |        |        |        |
| 001303 | 000 001 | 000050 |        |        |        |        |        |        |
|        | 102744 | 010146 | 010246 | 004774 | 000034 | 012602 | 012601 | 012600 |
|        | 016403 | 000030 | 005764 | 000042 | 001402 | 010302 | 000753 | 010301 |
|        | 000751 | 112221 | 005203 | 005365 |        |        |        |        |
| 001304 | 000 001 | 000034 |        |        |        |        |        |        |
|        | 103012 | 000002 | 005300 | 001343 | 010364 | 000030 | 000207 | 012700 |
|        | 001402 | 004767 | 006044 | 005264 | 000014 | 000207 |        |        |
| 001305 | 000 001 | 000050 |        |        |        |        |        |        |
|        | 103044 | 017400 | 000046 | 004767 | 010130 | 005701 | 001576 | 004767 |
|        | 007572 | 005764 | 000032 | 001161 | 132761 | 000003 | 000015 | 001020 |
|        | 004767 | 010302 | 004767 | 002422 |        |        |        |        |
| 001306 | 000 001 | 000050 |        |        |        |        |        |        |
|        | 103112 | 005703 | 001412 | 020327 | 000006 | 001157 | 105761 | 000004 |
|        | 001154 | 112761 | 000177 | 000004 | 000760 | 132761 | 000002 | 000015 |
|        | 001577 | 132761 | 000001 | 000015 |        |        |        |        |
| 001307 | 000 001 | 000050 |        |        |        |        |        |        |
|        | 103160 | 001573 | 016165 | 000032 | 000002 | 016165 | 000026 | 000004 |
|        | 016165 | 000030 | 000000 | 017446 | 000044 | 003562 | 021665 | 000000 |
|        | 101157 | 005316 | 016146 | 000032 |        |        |        |        |
| 001310 | 000 001 | 000050 |        |        |        |        |        |        |
|        | 103226 | 016146 | 000024 | 004767 | 004724 | 005726 | 012664 | 000032 |
|        | 012603 | 020361 | 000020 | 001442 | 010361 | 000020 | 016162 | 000000 |
|        | 000000 | 016162 | 000020 | 000030 |        |        |        |        |
| 001311 | 000 001 | 000050 |        |        |        |        |        |        |
|        | 103274 | 016162 | 000022 | 000032 | 016162 | 000024 | 000034 | 005764 |
|        | 000042 | 001012 | 005764 | 000032 | 001007 | 026561 | 000002 | 000024 |
|        | 103403 | 004767 | 172442 | 000402 |        |        |        |        |
| 001312 | 000 001 | 000050 |        |        |        |        |        |        |
|        | 103342 | 004767 | 172446 | 005703 | 001075 | 016261 | 000032 | 000022 |
|        | 016103 | 000022 | 016400 | 000032 | 010002 | 060300 | 010064 | 000032 |
|        | 010064 | 000030 | 005402 | 066102 |        |        |        |        |
| 001313 | 000 001 | 000050 |        |        |        |        |        |        |
|        | 103410 | 000024 | 020265 | 000002 | 101402 | 016502 | 000002 | 060002 |
|        | 010264 | 000026 | 000207 | 005764 | 000042 | 001415 | 005261 | 000020 |
|        | 005064 | 000032 | 000702 | 012703 |        |        |        |        |
| 001314 | 000 001 | 000050 |        |        |        |        |        |        |
|        | 103456 | 000014 | 000431 | 005703 | 002427 | 062703 | 000003 | 000424 |
|        | 016162 | 000000 | 000000 | 016162 | 000020 | 000030 | 016162 | 000022 |
|        | 000032 | 016162 | 000024 | 000034 |        |        |        |        |
| 001315 | 000 001 | 000042 |        |        |        |        |        |        |
|        | 103524 | 004767 | 172260 | 005703 | 001004 | 005765 | 000002 | 001340 |
|        | 000207 | 000167 | 000256 | 012703 | 000013 | 000773 | 012703 | 000015 |
|        | 000770 |        |        |        |        |        |        |        |

| | | | | | | | | |
|---|---|---|---|---|---|---|---|---|
| 001316 | 000 001 | 000050 | | | | | | |
| | 103564 | 010605 | 061505 | 062705 | 000004 | 010445 | 005745 | 010504 |
| | 010605 | 005725 | 005064 | 000024 | 005064 | 000020 | 005064 | 000022 |
| | 005764 | 000036 | 001457 | 002402 | | | | |
| 001317 | 000 001 | 000050 | | | | | | |
| | 103632 | 000167 | 000004 | 000167 | 000042 | 005764 | 000042 | 001407 |
| | 036527 | 000000 | 000002 | 001010 | 004774 | 000034 | 000771 | 052765 |
| | 000002 | 000000 | 004774 | 000034 | | | | |
| 001320 | 000 001 | 000050 | | | | | | |
| | 103700 | 000167 | 000074 | 005764 | 000042 | 001017 | 016400 | 000030 |
| | 016401 | 000026 | 020001 | 001404 | 005365 | 000002 | 105020 | 000772 |
| | 004774 | 000034 | 005765 | 000002 | | | | |
| 001321 | 000 001 | 000050 | | | | | | |
| | 103746 | 001361 | 017400 | 000044 | 005200 | 010075 | 000004 | 000167 |
| | 000012 | 005764 | 000014 | 001002 | 004774 | 000040 | 010400 | 010406 |
| | 012005 | 012004 | 012003 | 012002 | | | | |
| 001322 | 000 001 | 000050 | | | | | | |
| | 104014 | 012001 | 012000 | 062706 | 000050 | 000134 | 005703 | 002005 |
| | 012700 | 000400 | 004767 | 005040 | 000424 | 016400 | 000016 | 022703 |
| | 000004 | 001007 | 005710 | 001410 | | | | |
| 001323 | 000 001 | 000040 | | | | | | |
| | 104062 | 004767 | 006606 | 011064 | 000002 | 000742 | 005720 | 005710 |
| | 001370 | 000303 | 005203 | 010300 | 004767 | 004766 | 004767 | 006722 |
| 001324 | 000 001 | 000050 | | | | | | |
| | 104120 | 005046 | 005046 | 005046 | 005046 | 005046 | 010446 | 005046 |
| | 010046 | 010146 | 010246 | 010346 | 010446 | 010546 | 010604 | 016646 |
| | 000032 | 005066 | 000034 | 000207 | | | | |
| 001325 | 000 001 | 000030 | | | | | | |
| | 104166 | 004774 | 000034 | 010400 | 012005 | 012004 | 012003 | 012002 |
| | 012001 | 012000 | 022424 | 000134 | | | | |
| 001326 | 000 001 | 000050 | | | | | | |
| | 104214 | 005046 | 000421 | 012746 | 000001 | 000416 | 012746 | 000002 |
| | 000413 | 012746 | 000004 | 000410 | 012746 | 000005 | 000405 | 012746 |
| | 000010 | 000402 | 012746 | 000006 | | | | |
| 001327 | 000 001 | 000050 | | | | | | |
| | 104262 | 016605 | 000002 | 006305 | 022525 | 060605 | 061505 | 062705 |
| | 000014 | 010045 | 010145 | 010245 | 010345 | 010445 | 005745 | 010504 |
| | 016605 | 000002 | 006305 | 060605 | | | | |
| 001330 | 000 001 | 000050 | | | | | | |
| | 104330 | 022525 | 005725 | 004767 | 000132 | 012664 | 000022 | 001456 |
| | 016464 | 000022 | 000020 | 022764 | 000004 | 000020 | 103003 | 042764 |
| | 000003 | 000020 | 011603 | 006303 | | | | |
| 001331 | 000 001 | 000050 | | | | | | |
| | 104376 | 060603 | 011364 | 000024 | 004774 | 000040 | 004767 | 000056 |
| | 022764 | 000006 | 000022 | 001007 | 062764 | 000004 | 000024 | 004774 |
| | 000040 | 004767 | 000030 | 005316 | | | | |
| 001332 | 000 001 | 000050 | | | | | | |
| | 104444 | 001352 | 005745 | 010506 | 010400 | 012005 | 012004 | 012003 |
| | 012002 | 012001 | 012000 | 000134 | 005764 | 000014 | 001363 | 000207 |
| | 011603 | 006303 | 060603 | 011302 | | | | |
| 001333 | 000 001 | 000050 | | | | | | |
| | 104512 | 012264 | 000024 | 012201 | 110164 | 000020 | 005000 | 006101 |
| | 006100 | 006101 | 006100 | 006101 | 006101 | 006101 | 006101 | 042701 |
| | 177770 | 016464 | 000020 | 000022 | | | | |
| 001334 | 000 001 | 000050 | | | | | | |
| | 104560 | 022701 | 000003 | 101003 | 103411 | 122121 | 000417 | 026427 |
| | 000020 | 000004 | 002415 | 006264 | 000020 | 000412 | 022701 | 000004 |
| | 001002 | 006301 | 000403 | 005201 | | | | |
| 001335 | 000 001 | 000050 | | | | | | |
| | 104626 | 006264 | 000020 | 010164 | 000022 | 010446 | 012704 | 104666 |
| | 160004 | 160004 | 012246 | 005300 | 001375 | 000134 | 106474 | 106474 |
| | 104666 | 012600 | 012604 | 010046 | | | | |
| 001336 | 000 001 | 000050 | | | | | | |
| | 104674 | 004774 | 000040 | 004767 | 177566 | 066464 | 000020 | 000024 |
| | 022764 | 000004 | 000022 | 001410 | 022764 | 000006 | 000022 | 001007 |
| | 004774 | 000040 | 004767 | 177530 | | | | |
| 001337 | 000 001 | 000026 | | | | | | |
| | 104742 | 066464 | 000020 | 000024 | 012600 | 005300 | 001346 | 005316 |
| | 001250 | 000167 | 177460 | | | | | |
| 001340 | 000 001 | 000050 | | | | | | |
| | 104766 | 013400 | 004767 | 006210 | 005701 | 001427 | 132761 | 000004 |
| | 000015 | 001403 | 062704 | 000006 | 000134 | 132761 | 000003 | 000015 |
| | 001021 | 013461 | 000030 | 013461 | | | | |
| 001341 | 000 001 | 000050 | | | | | | |
| | 105034 | 000032 | 006361 | 000032 | 012461 | 000026 | 152761 | 000004 |
| | 000015 | 000134 | 012700 | 006001 | 004767 | 004014 | 000750 | 012700 |
| | 005401 | 004767 | 004002 | 004767 | | | | |
| 001342 | 000 001 | 000004 | | | | | | |
| | 105102 | 005736 | | | | | | |
| 001343 | 000 001 | 000050 | | | | | | |
| | 105104 | 010546 | 004767 | 005524 | 010004 | 111503 | 001570 | 005725 |
| | 013501 | 003573 | 020114 | 003171 | 006301 | 060104 | 016404 | 000002 |
| | 005303 | 001555 | 132764 | 000003 | | | | |
| 001344 | 000 001 | 000050 | | | | | | |
| | 105152 | 000015 | 001164 | 012501 | 012700 | 000005 | 012746 | 020040 |
| | 005300 | 001374 | 010602 | 012700 | 000006 | 010046 | 000406 | 121127 |
| | 000060 | 002414 | 121127 | 000071 | | | | |
| 001345 | 000 001 | 000050 | | | | | | |

|        |        |        |        |        |        |        |        |        |
|--------|--------|--------|--------|--------|--------|--------|--------|--------|
|        | 105220 | 003406 | 121127 | 000101 | 002406 | 121127 | 000132 | 003003 |
|        | 112122 | 005300 | 001361 | 005716 | 001414 | 020016 | 001426 | 122721 |
|        | 000056 | 001007 | 005016 | 010602 |        |        |        |        |
| 001346 | 000 001 | 000050 |        |        |        |        |        |        |
|        | 105266 | 062702 | 000010 | 012700 | 000003 | 000743 | 010401 | 062701 |
|        | 000004 | 012700 | 000002 | 010616 | 060016 | 005046 | 104042 | 012621 |
|        | 005300 | 002373 | 062706 | 000014 |        |        |        |        |
| 001347 | 000 001 | 000050 |        |        |        |        |        |        |
|        | 105334 | 005303 | 001460 | 011564 | 000036 | 005035 | 005303 | 001453 |
|        | 012546 | 005046 | 104042 | 012664 | 000002 | 005726 | 005303 | 001443 |
|        | 117564 | 000000 | 000005 | 005725 |        |        |        |        |
| 001350 | 000 001 | 000050 |        |        |        |        |        |        |
|        | 105402 | 005303 | 001435 | 013564 | 000034 | 005303 | 001431 | 117564 |
|        | 000000 | 000014 | 005725 | 005303 | 001423 | 027527 | 000000 | 000002 |
|        | 001414 | 023527 | 000001 | 001017 |        |        |        |        |
| 001351 | 000 001 | 000050 |        |        |        |        |        |        |
|        | 105450 | 020327 | 000003 | 001014 | 013500 | 006300 | 010064 | 000032 |
|        | 013564 | 000030 | 112764 | 000177 | 000004 | 012605 | 000167 | 007110 |
|        | 012774 | 177777 | 000036 | 012700 |        |        |        |        |
| 001352 | 000 001 | 000020 |        |        |        |        |        |        |
|        | 105516 | 007404 | 004767 | 003356 | 000765 | 012700 | 010004 | 000772 |
| 001353 | 000 001 | 000050 |        |        |        |        |        |        |
|        | 105534 | 005003 | 005764 | 000036 | 002005 | 136127 | 000015 | 000004 |
|        | 001533 | 000404 | 136127 | 000015 | 000004 | 001131 | 012762 | 106056 |
|        | 177776 | 010246 | 104006 | 012762 |        |        |        |        |
| 001354 | 000 001 | 000050 |        |        |        |        |        |        |
|        | 105602 | 106064 | 177776 | 105761 | 000004 | 001426 | 012762 | 106104 |
|        | 000010 | 016146 | 000032 | 016146 | 000030 | 012746 | 000200 | 004767 |
|        | 004320 | 005726 | 005726 | 001401 |        |        |        |        |
| 001355 | 000 001 | 000050 |        |        |        |        |        |        |
|        | 105650 | 005216 | 010246 | 062716 | 000014 | 010246 | 104015 | 005226 |
|        | 001107 | 005203 | 005764 | 000036 | 002013 | 010246 | 104013 | 022626 |
|        | 011661 | 000024 | 062661 | 000024 |        |        |        |        |
| 001356 | 000 001 | 000050 |        |        |        |        |        |        |
|        | 105716 | 012761 | 177777 | 000020 | 000405 | 006303 | 005764 | 000042 |
|        | 001401 | 006303 | 110362 | 000012 | 010246 | 104013 | 012603 | 022626 |
|        | 032703 | 000400 | 001010 | 012762 |        |        |        |        |
| 001357 | 000 001 | 000050 |        |        |        |        |        |        |
|        | 105764 | 106114 | 000010 | 010246 | 062716 | 000014 | 010246 | 104016 |
|        | 116261 | 000012 | 000004 | 016403 | 000036 | 002002 | 012703 | 000002 |
|        | 005203 | 150361 | 000015 | 016261 |        |        |        |        |
| 001360 | 000 001 | 000050 |        |        |        |        |        |        |
|        | 106032 | 000000 | 000000 | 005003 | 000207 | 012703 | 000003 | 000207 |
|        | 012703 | 000004 | 000207 | 012703 | 177777 | 000207 | 012703 | 177777 |
|        | 010246 | 012762 | 106056 | 177776 |        |        |        |        |
| 001361 | 000 001 | 000050 |        |        |        |        |        |        |
|        | 106100 | 104007 | 000207 | 005726 | 012703 | 000002 | 000766 | 122762 |
|        | 000002 | 000012 | 001010 | 122762 | 000002 | 000013 | 001004 | 112762 |
|        | 000013 | 000012 | 000707 | 012703 |        |        |        |        |
| 001362 | 000 001 | 000032 |        |        |        |        |        |        |
|        | 106146 | 000005 | 122762 | 000006 | 000013 | 001744 | 005203 | 122762 |
|        | 000002 | 000013 | 001737 | 005203 | 000735 |        |        |        |
| 001363 | 000 001 | 000050 |        |        |        |        |        |        |
|        | 106176 | 022764 | 055740 | 000006 | 001004 | 010446 | 004767 | 000056 |
|        | 012604 | 004767 | 004406 | 062700 | 000006 | 011001 | 010420 | 010124 |
|        | 011024 | 005010 | 022424 | 000134 |        |        |        |        |
| 001364 | 000 001 | 000030 |        |        |        |        |        |        |
|        | 106244 | 010046 | 004767 | 004356 | 062700 | 000006 | 011004 | 012420 |
|        | 012410 | 012600 | 000167 | 006324 |        |        |        |        |
| 001365 | 000 001 | 000004 |        |        |        |        |        |        |
|        | 106272 | 000207 |        |        |        |        |        |        |
| 001366 | 000 001 | 000042 |        |        |        |        |        |        |
|        | 106274 | 105426 | 000410 | 005426 | 000404 | 012666 | 000002 | 005726 |
|        | 012616 | 005426 | 102403 | 003003 | 001401 | 005724 | 005724 | 011404 |
|        | 000134 |        |        |        |        |        |        |        |
| 001367 | 000 001 | 000050 |        |        |        |        |        |        |
|        | 106334 | 012403 | 005000 | 000423 | 012403 | 005000 | 000410 | 012403 |
|        | 012602 | 005302 | 002430 | 016301 | 000006 | 004767 | 000070 | 012602 |
|        | 005302 | 002422 | 060002 | 016301 |        |        |        |        |
| 001370 | 000 001 | 000050 |        |        |        |        |        |        |
|        | 106402 | 000004 | 004767 | 000050 | 012602 | 005302 | 002413 | 060200 |
|        | 116302 | 000002 | 006202 | 001402 | 006300 | 000774 | 061300 | 000134 |
|        | 005726 | 005724 | 012700 | 000007 |        |        |        |        |
| 001371 | 000 001 | 000026 |        |        |        |        |        |        |
|        | 106450 | 004767 | 002426 | 011300 | 000134 | 012700 | 177304 | 010120 |
|        | 010210 | 014000 | 000207 |        |        |        |        |        |
| 001372 | 000 001 | 000042 |        |        |        |        |        |        |
|        | 106474 | 012700 | 177304 | 012620 | 012610 | 014046 | 132767 | 000002 |
|        | 070575 | 001401 | 000134 | 005016 | 012700 | 007003 | 004767 | 002350 |
|        | 000134 |        |        |        |        |        |        |        |
| 001373 | 000 001 | 000050 |        |        |        |        |        |        |
|        | 106534 | 010446 | 010546 | 012704 | 177304 | 012705 | 100000 | 016614 |
|        | 000012 | 016614 | 000010 | 001565 | 005237 | 177314 | 106037 | 177311 |
|        | 006146 | 012446 | 105016 | 000316 |        |        |        |        |
| 001374 | 000 001 | 000050 |        |        |        |        |        |        |
|        | 106602 | 012737 | 000007 | 177314 | 011446 | 050544 | 012446 | 016614 |

|        |        |        |        |        |        |        |        |        |
|--------|--------|--------|--------|--------|--------|--------|--------|--------|
|        | 000016 | 016644 | 000014 | 001526 | 005237 | 177314 | 106037 | 177311 |
|        | 005566 | 000006 | 011403 | 105003 |        |        |        |        |
| 001375 | 000 001 | 000050 |        |        |        |        |        |        |
|        | 106650 | 000303 | 060366 | 000004 | 012737 | 000007 | 177314 | 012402 |
|        | 050502 | 005000 | 005001 | 012403 | 001002 | 005744 | 000407 | 011614 |
|        | 024444 | 060314 | 005703 | 100001 |        |        |        |        |
| 001376 | 000 001 | 000050 |        |        |        |        |        |        |
|        | 106716 | 061614 | 012401 | 016624 | 000002 | 001002 | 005744 | 000412 |
|        | 010214 | 024444 | 066614 | 000002 | 005766 | 000002 | 100001 | 060214 |
|        | 062401 | 005500 | 010224 | 060200 |        |        |        |        |
| 001377 | 000 001 | 000050 |        |        |        |        |        |        |
|        | 106764 | 011614 | 062600 | 064401 | 005500 | 064400 | 005726 | 012604 |
|        | 006101 | 006100 | 103403 | 006101 | 006100 | 005304 | 162704 | 000200 |
|        | 003437 | 022704 | 000377 | 002430 |        |        |        |        |
| 001400 | 000 001 | 000050 |        |        |        |        |        |        |
|        | 107032 | 105001 | 150001 | 000301 | 105000 | 150400 | 000300 | 006026 |
|        | 006000 | 006001 | 005501 | 005500 | 103415 | 102414 | 010066 | 000010 |
|        | 010166 | 000012 | 012605 | 012604 |        |        |        |        |
| 001401 | 000 001 | 000044 |        |        |        |        |        |        |
|        | 107100 | 022626 | 000134 | 022626 | 022626 | 000411 | 005726 | 012700 |
|        | 006003 | 000403 | 012700 | 003405 | 005726 | 004767 | 001746 | 005000 |
|        | 005001 | 000751 |        |        |        |        |        |        |
| 001402 | 000 001 | 000032 |        |        |        |        |        |        |
|        | 107142 | 017500 | 000002 | 002002 | 005400 | 102402 | 000167 | 005436 |
|        | 012700 | 003404 | 004767 | 001712 | 000771 |        |        |        |
| 001403 | 000 001 | 000050 |        |        |        |        |        |        |
|        | 107172 | 011646 | 011646 | 005066 | 000002 | 005066 | 000004 | 005046 |
|        | 016601 | 000002 | 003002 | 001433 | 005401 | 006146 | 012702 | 000217 |
|        | 105066 | 000004 | 012703 | 177304 |        |        |        |        |
| 001404 | 000 001 | 000050 |        |        |        |        |        |        |
|        | 107240 | 005013 | 010143 | 012700 | 177312 | 005010 | 162002 | 012710 |
|        | 000002 | 011301 | 110166 | 000005 | 105001 | 150201 | 000301 | 006026 |
|        | 006001 | 106066 | 000003 | 010116 |        |        |        |        |
| 001405 | 000 001 | 000004 |        |        |        |        |        |        |
|        | 107306 | 000134 |        |        |        |        |        |        |
| 001406 | 000 001 | 000050 |        |        |        |        |        |        |
|        | 107310 | 010446 | 010546 | 005000 | 005001 | 005046 | 006366 | 000012 |
|        | 006116 | 005046 | 005766 | 000010 | 001453 | 156616 | 000015 | 001446 |
|        | 156600 | 000014 | 000300 | 000261 |        |        |        |        |
| 001407 | 000 001 | 000050 |        |        |        |        |        |        |
|        | 107356 | 006000 | 156600 | 000017 | 156601 | 000016 | 000301 | 005002 |
|        | 005003 | 006366 | 000010 | 005566 | 000002 | 156602 | 000011 | 160216 |
|        | 005002 | 156602 | 000010 | 000302 |        |        |        |        |
| 001410 | 000 001 | 000050 |        |        |        |        |        |        |
|        | 107424 | 000261 | 006002 | 156602 | 000013 | 156603 | 000012 | 000303 |
|        | 000241 | 006000 | 006001 | 006002 | 006003 | 020002 | 103430 | 103024 |
|        | 022626 | 000415 | 005726 | 012700 |        |        |        |        |
| 001411 | 000 001 | 000050 |        |        |        |        |        |        |
|        | 107472 | 004003 | 000406 | 005746 | 012700 | 003003 | 000402 | 012700 |
|        | 001405 | 005726 | 004767 | 001362 | 005066 | 000010 | 005066 | 000012 |
|        | 000472 | 006000 | 006001 | 005216 |        |        |        |        |
| 001412 | 000 001 | 000050 |        |        |        |        |        |        |
|        | 107540 | 000241 | 006003 | 006000 | 006001 | 012705 | 177304 | 010115 |
|        | 010045 | 010245 | 005725 | 012501 | 012504 | 010315 | 005745 | 006201 |
|        | 160145 | 005337 | 177316 | 010245 |        |        |        |        |
| 001413 | 000 001 | 000050 |        |        |        |        |        |        |
|        | 107606 | 022525 | 005415 | 012737 | 000002 | 177316 | 060445 | 005037 |
|        | 177312 | 163716 | 177312 | 012737 | 177772 | 177314 | 012566 | 000014 |
|        | 011505 | 012604 | 062704 | 000200 |        |        |        |        |
| 001414 | 000 001 | 000050 |        |        |        |        |        |        |
|        | 107654 | 003714 | 022704 | 000377 | 002706 | 110466 | 000013 | 006026 |
|        | 006066 | 000010 | 006005 | 005505 | 005566 | 000010 | 010566 | 000012 |
|        | 103671 | 102670 | 012605 | 012604 |        |        |        |        |
| 001415 | 000 001 | 000006 |        |        |        |        |        |        |
|        | 107722 | 022626 | 000134 |        |        |        |        |        |
| 001416 | 000 001 | 000040 |        |        |        |        |        |        |
|        | 107726 | 012700 | 177304 | 012601 | 001406 | 012610 | 005740 | 010140 |
|        | 022020 | 011046 | 000134 | 012700 | 002403 | 004767 | 001120 | 000134 |
| 001417 | 000 001 | 000024 |        |        |        |        |        |        |
|        | 107764 | 016501 | 000002 | 012100 | 006100 | 000241 | 006000 | 011101 |
|        | 000167 | 004610 |        |        |        |        |        |        |
| 001420 | 000 001 | 000050 |        |        |        |        |        |        |
|        | 110006 | 062716 | 100000 | 010446 | 005046 | 005002 | 005003 | 006366 |
|        | 000006 | 006166 | 000004 | 156603 | 000005 | 001546 | 106116 | 006366 |
|        | 000012 | 006166 | 000010 | 156602 |        |        |        |        |
| 001421 | 000 001 | 000050 |        |        |        |        |        |        |
|        | 110054 | 000011 | 001014 | 106016 | 006066 | 000004 | 006066 | 000006 |
|        | 016666 | 000004 | 000010 | 016666 | 000006 | 000012 | 000522 | 106166 |
|        | 000001 | 112766 | 000001 | 000011 |        |        |        |        |
| 001422 | 000 001 | 000050 |        |        |        |        |        |        |
|        | 110122 | 112766 | 000001 | 000005 | 160302 | 003005 | 016600 | 000010 |
|        | 016601 | 000012 | 000415 | 060203 | 016600 | 000004 | 016601 | 000006 |
|        | 016666 | 000010 | 000004 | 016666 |        |        |        |        |
| 001423 | 000 001 | 000050 |        |        |        |        |        |        |
|        | 110170 | 000012 | 000006 | 000316 | 005402 | 126616 | 000001 | 001403 |
|        | 005401 | 005500 | 005400 | 005702 | 001422 | 022702 | 177747 | 003405 |
|        | 016600 | 000004 | 016601 | 000006 |        |        |        |        |
| 001424 | 000 001 | 000050 |        |        |        |        |        |        |

|         |        |        |        |        |        |        |        |        |
|---------|--------|--------|--------|--------|--------|--------|--------|--------|
|         | 110236 | 000430 | 010137 | 177304 | 010037 | 177302 | 010237 | 177316 |
|         | 013701 | 177304 | 013700 | 177302 | 066600 | 000004 | 066601 | 000006 |
|         | 005500 | 126616 | 000001 | 001035 |        |        |        |        |
| 001425  | 000 001 | 000050 |       |        |        |        |        |        |
|         | 110304 | 030027 | 001000 | 001403 | 006200 | 006001 | 005203 | 000303 |
|         | 001020 | 150003 | 006016 | 006003 | 006001 | 005501 | 005503 | 102411 |
|         | 103410 | 010366 | 000010 | 010166 |        |        |        |        |
| 001426  | 000 001 | 000050 |       |        |        |        |        |        |
|         | 110352 | 000012 | 005726 | 012604 | 022626 | 000134 | 012700 | 001003 |
|         | 004767 | 000506 | 000767 | 005700 | 003005 | 001441 | 005400 | 005401 |
|         | 005600 | 000316 | 030027 | 000700 |        |        |        |        |
| 001427  | 000 001 | 000050 |       |        |        |        |        |        |
|         | 110420 | 001023 | 010137 | 177304 | 010037 | 177302 | 005037 | 177312 |
|         | 163703 | 177312 | 012737 | 177772 | 177316 | 062703 | 000006 | 003421 |
|         | 013700 | 177302 | 013701 | 177304 |        |        |        |        |
| 001430  | 000 001 | 000050 |       |        |        |        |        |        |
|         | 110466 | 000714 | 030027 | 000400 | 001007 | 005303 | 006301 | 006100 |
|         | 000771 | 005701 | 001341 | 000407 | 005703 | 003300 | 012700 | 001005 |
|         | 004767 | 000352 | 005001 | 005003 |        |        |        |        |
| 001431  | 000 001 | 000004 |       |        |        |        |        |        |
|         | 110534 | 000703 |        |        |        |        |        |        |
| 001432  | 000 001 | 000050 |       |        |        |        |        |        |
|         | 110536 | 012666 | 000002 | 012666 | 000002 | 005002 | 005202 | 012601 |
|         | 006116 | 006101 | 006144 | 110103 | 105001 | 000301 | 162701 | 000201 |
|         | 002436 | 001416 | 022701 | 000017 |        |        |        |        |
| 001433  | 000 001 | 000050 |       |        |        |        |        |        |
|         | 110604 | 002425 | 000303 | 105003 | 156603 | 000003 | 012700 | 177304 |
|         | 010310 | 010240 | 010137 | 177314 | 011002 | 005402 | 102406 | 003007 |
|         | 006026 | 103401 | 005402 | 010216 |        |        |        |        |
| 001434  | 000 001 | 000026 |       |        |        |        |        |        |
|         | 110652 | 000134 | 006026 | 103774 | 005746 | 012700 | 013003 | 004767 |
|         | 000210 | 005002 | 000762 |        |        |        |        |        |
| 001435  | 000 001 | 000050 |       |        |        |        |        |        |
|         | 110476 | 012702 | 000001 | 010201 | 017500 | 000002 | 020027 | 000017 |
|         | 101013 | 000241 | 005300 | 002402 | 006101 | 000774 | 030137 | 177570 |
|         | 001001 | 005202 | 010275 | 000004 |        |        |        |        |
| 001436  | 000 001 | 000006 |       |        |        |        |        |        |
|         | 110744 | 000167 | 003646 |        |        |        |        |        |
| 001437  | 000 001 | 000006 |       |        |        |        |        |        |
|         | 110750 | 005726 | 000134 |        |        |        |        |        |
| 001440  | 000 001 | 000014 |       |        |        |        |        |        |
|         | 110754 | 010346 | 010246 | 010146 | 010046 | 000134 |        |        |
| 001441  | 000 001 | 000014 |       |        |        |        |        |        |
|         | 110766 | 004767 | 001636 | 012460 | 000010 | 000134 |        |        |
| 001442  | 000 001 | 000016 |       |        |        |        |        |        |
|         | 111000 | 012700 | 000010 | 004767 | 000072 | 004767 | 002026 |        |
| 001443  | 000 001 | 000016 |       |        |        |        |        |        |
|         | 111014 | 012700 | 000010 | 004767 | 000056 | 004567 | 002012 |        |
| 001444  | 000 001 | 000016 |       |        |        |        |        |        |
|         | 111030 | 012700 | 000010 | 004767 | 000042 | 004767 | 001776 |        |
| 001445  | 000 001 | 000016 |       |        |        |        |        |        |
|         | 111044 | 012700 | 000010 | 004767 | 000026 | 004767 | 001762 |        |
| 001446  | 000 001 | 000050 |       |        |        |        |        |        |
|         | 111060 | 010046 | 016500 | 000002 | 004767 | 000010 | 012600 | 000205 |
|         | 010046 | 000772 | 010046 | 010146 | 010246 | 010346 | 010446 | 010546 |
|         | 110003 | 002411 | 010002 | 004767 |        |        |        |        |
| 001447  | 000 001 | 000050 |       |        |        |        |        |        |
|         | 111126 | 001500 | 010005 | 016504 | 000004 | 020364 | 177776 | 101402 |
|         | 005000 | 000763 | 004767 | 001534 | 060300 | 112710 | 000001 | 010200 |
|         | 006303 | 006303 | 006303 | 060304 |        |        |        |        |
| 001450  | 000 001 | 000050 |       |        |        |        |        |        |
|         | 111174 | 000300 | 110003 | 002761 | 120314 | 003357 | 022764 | 177777 |
|         | 000004 | 001424 | 002435 | 022764 | 177776 | 000004 | 001007 | 012765 |
|         | 000003 | 000012 | 012764 | 113042 |        |        |        |        |
| 001451  | 000 001 | 000050 |       |        |        |        |        |        |
|         | 111242 | 000002 | 000410 | 160300 | 006300 | 060300 | 010046 | 016746 |
|         | 000002 | 000004 | 001430 | 010400 | 012605 | 012604 | 012603 | 012602 |
|         | 012601 | 016000 | 000002 | 000200 |        |        |        |        |
| 001452  | 000 001 | 000050 |       |        |        |        |        |        |
|         | 111310 | 000207 | 010046 | 004767 | 001310 | 012005 | 011002 | 012600 |
|         | 016501 | 000002 | 001463 | 006301 | 060501 | 016101 | 000002 | 001456 |
|         | 136127 | 000015 | 000006 | 001052 |        |        |        |        |
| 001453  | 000 001 | 000050 |       |        |        |        |        |        |
|         | 111356 | 105761 | 000004 | 001405 | 126127 | 000004 | 000002 | 001043 |
|         | 000454 | 010046 | 016500 | 000002 | 004767 | 002000 | 012600 | 110003 |
|         | 012762 | 111476 | 177776 | 012762 |        |        |        |        |
| 001454  | 000 001 | 000050 |       |        |        |        |        |        |
|         | 111424 | 111476 | 000010 | 010246 | 104006 | 112762 | 000002 | 000012 |
|         | 010246 | 062716 | 000014 | 010246 | 104016 | 116261 | 000012 | 000004 |
|         | 105261 | 000015 | 016261 | 000000 |        |        |        |        |
| 001455  | 000 001 | 000050 |       |        |        |        |        |        |
|         | 111472 | 000000 | 000414 | 010246 | 104007 | 160300 | 006300 | 060300 |
|         | 010046 | 016746 | 000006 | 000004 | 000167 | 000376 | 000353 | 016162 |
|         | 000000 | 000000 | 005062 | 177776 |        |        |        |        |
| 001456  | 000 001 | 000050 |       |        |        |        |        |        |
|         | 111540 | 014505 | 001524 | 005715 | 001012 | 010544 | 104006 | 012765 |

|        |        |        |        |        |        |        |        |        |
|--------|--------|--------|--------|--------|--------|--------|--------|--------|
|        | 112010 | 000010 | 010546 | 062716 | 000014 | 010546 | 104016 | 012746 |
|        | 000100 | 005046 | 116416 | 000001 |        |        |        |        |
| 001457 | 000 001 000050 |   |        |        |        |        |        |        |
|        | 111606 | 060316 | 010546 | 104013 | 022626 | 006316 | 004767 | 000336 |
|        | 005726 | 012600 | 012665 | 000030 | 010546 | 062716 | 000026 | 010546 |
|        | 104011 | 010546 | 104001 | 016505 |        |        |        |        |
| 001460 | 000 001 000050 |   |        |        |        |        |        |        |
|        | 111654 | 000032 | 060005 | 010500 | 005720 | 012703 | 000037 | 005303 |
|        | 002403 | 022720 | 020040 | 001373 | 012740 | 005015 | 012715 | 005015 |
|        | 012762 | 000100 | 000002 | 006303 |        |        |        |        |
| 001461 | 000 001 000050 |   |        |        |        |        |        |        |
|        | 111722 | 160362 | 000002 | 016262 | 000002 | 000006 | 010562 | 000010 |
|        | 112762 | 000004 | 000004 | 010246 | 062716 | 000002 | 010246 | 104002 |
|        | 010246 | 104001 | 132762 | 000100 |        |        |        |        |
| 001462 | 000 001 000050 |   |        |        |        |        |        |        |
|        | 111770 | 000005 | 001447 | 010146 | 016746 | 000004 | 000004 | 000446 |
|        | 000352 | 010546 | 104007 | 105000 | 000300 | 010046 | 010346 | 004767 |
|        | 000600 | 010005 | 062705 | 000014 |        |        |        |        |
| 001463 | 000 001 000050 |   |        |        |        |        |        |        |
|        | 112036 | 010546 | 022525 | 062716 | 000007 | 012746 | 000003 | 104042 |
|        | 010546 | 012746 | 000003 | 104042 | 012765 | 005015 | 000010 | 012715 |
|        | 052122 | 012745 | 047506 | 005745 |        |        |        |        |
| 001464 | 000 001 000050 |   |        |        |        |        |        |        |
|        | 112104 | 012703 | 000031 | 000674 | 004767 | 000204 | 005703 | 001325 |
|        | 005764 | 000004 | 001002 | 000167 | 177132 | 005264 | 000006 | 026464 |
|        | 000006 | 000004 | 002770 | 012760 |        |        |        |        |
| 001465 | 000 001 000012 |   |        |        |        |        |        |        |
|        | 112152 | 000002 | 000012 | 000167 | 177054 |        |        |        |
| 001466 | 000 001 000050 |   |        |        |        |        |        |        |
|        | 112162 | 010046 | 010146 | 010246 | 010346 | 010446 | 016603 | 000020 |
|        | 016604 | 000016 | 005000 | 005002 | 005001 | 000241 | 006004 | 103003 |
|        | 060301 | 005500 | 060200 | 006303 |        |        |        |        |
| 001467 | 000 001 000050 |   |        |        |        |        |        |        |
|        | 112230 | 006102 | 005704 | 001366 | 005004 | 005002 | 016603 | 000014 |
|        | 006203 | 001405 | 006200 | 006001 | 006002 | 005204 | 000771 | 005000 |
|        | 006302 | 006100 | 005304 | 001374 |        |        |        |        |
| 001470 | 000 001 000026 |   |        |        |        |        |        |        |
|        | 112276 | 010166 | 000020 | 010066 | 000016 | 012604 | 012603 | 012602 |
|        | 012601 | 012600 | 000207 |        |        |        |        |        |
| 001471 | 000 001 000050 |   |        |        |        |        |        |        |
|        | 112322 | 010046 | 010146 | 010446 | 004767 | 000274 | 010003 | 005763 |
|        | 000006 | 001525 | 010501 | 012700 | 000014 | 112721 | 000040 | 005300 |
|        | 001374 | 012711 | 005015 | 112765 |        |        |        |        |
| 001472 | 000 001 000050 |   |        |        |        |        |        |        |
|        | 112370 | 000011 | 000006 | 012715 | 040516 | 012765 | 042515 | 000002 |
|        | 112765 | 000123 | 000007 | 012765 | 050505 | 000010 | 012700 | 000020 |
|        | 004767 | 000102 | 016304 | 000006 |        |        |        |        |
| 001473 | 000 001 000050 |   |        |        |        |        |        |        |
|        | 112436 | 016301 | 000010 | 010146 | 010546 | 062716 | 000007 | 012746 |
|        | 000003 | 104042 | 016446 | 000006 | 016446 | 000004 | 010546 | 012746 |
|        | 000001 | 104042 | 010546 | 062716 |        |        |        |        |
| 001474 | 000 001 000050 |   |        |        |        |        |        |        |
|        | 112504 | 000003 | 012746 | 000001 | 104042 | 004767 | 000014 | 016401 |
|        | 000002 | 011404 | 001345 | 000167 | 000062 | 010062 | 000002 | 010062 |
|        | 000006 | 010562 | 000010 | 012762 |        |        |        |        |
| 001475 | 000 001 000050 |   |        |        |        |        |        |        |
|        | 112552 | 000004 | 000004 | 010246 | 062716 | 000002 | 010246 | 104002 |
|        | 010246 | 104001 | 132762 | 000100 | 000005 | 001001 | 000207 | 005003 |
|        | 005203 | 005726 | 000401 | 005003 |        |        |        |        |
| 001476 | 000 001 000012 |   |        |        |        |        |        |        |
|        | 112620 | 012604 | 012601 | 012600 | 000207 |        |        |        |
| 001477 | 000 001 000050 |   |        |        |        |        |        |        |
|        | 112630 | 012700 | 113356 | 000207 | 004767 | 177766 | 011000 | 000207 |
|        | 004767 | 177764 | 005720 | 000207 | 010046 | 004767 | 177744 | 016002 |
|        | 000002 | 012600 | 000207 | 005761 |        |        |        |        |
| 001500 | 000 001 000022 |   |        |        |        |        |        |        |
|        | 112674 | 000034 | 001402 | 010371 | 000036 | 000207 | 012700 | 113030 |
|        | 000207 |        |        |        |        |        |        |        |
| 001501 | 000 001 000050 |   |        |        |        |        |        |        |
|        | 112716 | 000010 | 000005 | 111310 | 177775 | 000000 | 003021 | 111310 |
|        | 000000 | 000000 | 014005 | 111310 | 000001 | 000000 | 017036 | 111310 |
|        | 000003 | 000000 | 036424 | 111310 |        |        |        |        |
| 001502 | 000 001 000050 |   |        |        |        |        |        |        |
|        | 112764 | 000004 | 000000 | 051014 | 111310 | 177777 | 000000 | 057403 |
|        | 111310 | 000000 | 000000 | 061412 | 111310 | 000007 | 000000 | 067005 |
|        | 111310 | 000001 | 000000 | 000000 |        |        |        |        |
| 001503 | 000 001 000011 |   |        |        |        |        |        |        |
|        | 113032 | 000000 | 000000 | 000000 | 000    |        |        |        |
| 001504 | 000 001 000042 |   |        |        |        |        |        |        |
|        | 113042 | 004767 | 000034 | 004767 | 177556 | 016000 | 000012 | 001001 |
|        | 104060 | 005300 | 001775 | 010046 | 016746 | 000004 | 000004 | 000770 |
|        | 000351 |        |        |        |        |        |        |        |
| 001505 | 000 001 000050 |   |        |        |        |        |        |        |
|        | 113102 | 004767 | 177522 | 010004 | 005000 | 005200 | 002432 | 020074 |
|        | 000000 | 003023 | 004767 | 000054 | 005701 | 001767 | 136127 | 000015 |
|        | 000003 | 001763 | 016402 | 000002 |        |        |        |        |
| 001506 | 000 001 000036 |   |        |        |        |        |        |        |
|        | 113150 | 016162 | 000000 | 000000 | 004767 | 000070 | 016261 | 000000 |

| | | | | | | | | |
|---|---|---|---|---|---|---|---|---|
| | | 000000 | 000750 | 011400 | 016000 | 000002 | 002751 | 000207 |
| 001507 | 000 001 | 000050 | | | | | | |
| | | 113204 | 010001 | 004767 | 177424 | 010003 | 010100 | 003410 | 020013 |
| | | 003011 | 006301 | 060301 | 016101 | 000002 | 001404 | 000207 | 020027 |
| | | 177775 | 001767 | 005001 | 000207 | | | |
| 001510 | 000 001 | 000050 | | | | | | |
| | | 113252 | 012762 | 113350 | 177776 | 010246 | 104013 | 012603 | 022626 |
| | | 032703 | 000400 | 001002 | 010246 | 104017 | 010246 | 104007 | 105061 |
| | | 000004 | 142761 | 000007 | 000015 | | | |
| 001511 | 000 001 | 000040 | | | | | | |
| | | 113320 | 005061 | 000016 | 005061 | 000020 | 005061 | 000022 | 005061 |
| | | 000024 | 005061 | 000000 | 005003 | 000207 | 012703 | 177777 | 000207 |
| 001512 | 000 001 | 000016 | | | | | | |
| | | 113356 | 113604 | 114332 | 112720 | 000000 | 000000 | 000000 |
| 001513 | 000 001 | 000050 | | | | | | |
| | | 113410 | 005062 | 000000 | 016162 | 000002 | 000006 | 116162 | 000005 |
| | | 000005 | 005062 | 000012 | 016162 | 000006 | 000014 | 016162 | 000010 |
| | | 000016 | 016162 | 000012 | 000020 | | | |
| 001514 | 000 001 | 000050 | | | | | | |
| | | 113456 | 016162 | 000034 | 000022 | 116162 | 000014 | 000024 | 010046 |
| | | 004767 | 177130 | 010003 | 012600 | 062703 | 000014 | 020027 | 177775 |
| | | 001425 | 010046 | 010346 | 012746 | | | |
| 001515 | 000 001 | 000050 | | | | | | |
| | | 113524 | 000003 | 104042 | 005723 | 122713 | 000060 | 001005 | 005203 |
| | | 112763 | 000040 | 000002 | 000770 | 010346 | 005046 | 104042 | 012662 |
| | | 000002 | 005726 | 000207 | 012762 | | | |
| 001516 | 000 001 | 000010 | | | | | | |
| | | 113572 | 012327 | 000002 | 000207 | | | |
| 001517 | 000 001 | 000050 | | | | | | |
| | | 113600 | 114230 | 114272 | 000010 | 177775 | 113630 | 113670 | 113730 |
| | | 113770 | 114030 | 114070 | 114130 | 114170 | 000000 | 042420 | 000000 |
| | | 023752 | 140117 | 014474 | 000233 | | | |
| 001520 | 000 001 | 000050 | | | | | | |
| | | 113446 | 000000 | 000000 | 000000 | 000000 | 000000 | 000000 | 000000 |
| | | 000000 | 000000 | 000000 | 042420 | 000000 | 023752 | 140120 | 014474 |
| | | 000233 | 000000 | 000000 | 000000 | | | |
| 001521 | 000 001 | 000050 | | | | | | |
| | | 113714 | 000000 | 000000 | 000000 | 000000 | 000000 | 000000 | 000000 |
| | | 012620 | 000000 | 023752 | 140121 | 014474 | 000233 | 000000 | 000000 |
| | | 000000 | 000000 | 000000 | 000000 | | | |
| 001522 | 000 001 | 000050 | | | | | | |
| | | 113762 | 000000 | 000000 | 000000 | 000000 | 052140 | 000000 | 023752 |
| | | 140122 | 014474 | 000233 | 000000 | 000000 | 000000 | 000000 | 000000 |
| | | 000000 | 000000 | 000000 | 000000 | | | |
| 001523 | 000 001 | 000050 | | | | | | |
| | | 114030 | 000000 | 046600 | 000000 | 023752 | 140123 | 014474 | 000233 |
| | | 000000 | 000000 | 000000 | 000000 | 000000 | 000000 | 000000 | 000000 |
| | | 000000 | 000000 | 075250 | 000000 | | | |
| 001524 | 000 001 | 000050 | | | | | | |
| | | 114076 | 023752 | 140124 | 014474 | 000233 | 000000 | 000000 | 000000 |
| | | 000000 | 000000 | 000000 | 000000 | 000000 | 000000 | 000000 | 075250 |
| | | 000000 | 023752 | 140125 | 014474 | | | |
| 001525 | 000 001 | 000050 | | | | | | |
| | | 114144 | 000233 | 000000 | 000000 | 000000 | 000000 | 000000 | 000000 |
| | | 000000 | 000000 | 000000 | 000000 | 066540 | 000000 | 023752 | 140126 |
| | | 014474 | 000233 | 000000 | 000000 | | | |
| 001526 | 000 001 | 000050 | | | | | | |
| | | 114212 | 000000 | 000000 | 000000 | 000000 | 000000 | 000000 | 000000 |
| | | 000000 | 042420 | 000000 | 023752 | 012327 | 014474 | 000233 | 000000 |
| | | 000000 | 000000 | 000000 | 000000 | | | |
| 001527 | 000 001 | 000050 | | | | | | |
| | | 114260 | 000000 | 000000 | 000000 | 000000 | 000000 | 000000 | 021042 |
| | | 000001 | 075250 | 000000 | 000004 | 023752 | 071726 | 015046 | 000401 |
| | | 000322 | 000004 | 000000 | 000000 | | | |
| 001530 | 000 001 | 000004 | | | | | | |
| | | 114326 | 000000 | | | | | | |
| 001531 | 000 001 | 000040 | | | | | | |
| | | 114330 | 000000 | 000000 | 000000 | 000001 | 000000 | 000000 | 000000 |
| | | 000000 | 000000 | 000000 | 000000 | 000000 | 000210 | 000000 | 000000 |
| 001532 | 000 001 | 000050 | | | | | | |
| | | 114576 | 010546 | 010405 | 000135 | 010546 | 010500 | 010405 | 062500 |
| | | 000130 | 000205 | 005726 | 000134 | 005726 | 062406 | 000134 | 012400 |
| | | 060500 | 011000 | 000134 | 012402 | | | |
| 001533 | 000 001 | 000010 | | | | | | |
| | | 114644 | 060502 | 011234 | 000134 | | | |
| 001534 | 000 001 | 000050 | | | | | | |
| | | 114652 | 012701 | 114724 | 000440 | 012701 | 114730 | 000435 | 012701 |
| | | 114734 | 000432 | 012701 | 114740 | 000427 | 012701 | 114750 | 000424 |
| | | 012701 | 114744 | 000421 | 012701 | | | |
| 001535 | 000 001 | 000050 | | | | | | |
| | | 114720 | 114754 | 000416 | 000002 | 000001 | 000004 | 000001 | 000010 |
| | | 000001 | 000004 | 000002 | 000010 | 000002 | 000004 | 000004 | 000010 |
| | | 000004 | 010602 | 162106 | 010600 | | | |
| 001536 | 000 001 | 000042 | | | | | | |
| | | 114766 | 011103 | 012220 | 005303 | 001375 | 014103 | 006203 | 012402 |
| | | 012220 | 005303 | 001375 | 000134 | 011646 | 113401 | 010166 | 000002 |
| | | 000134 | | | | | | | |
| 001537 | 000 001 | 000002 | | | | | | |
| | | 036710 | | | | | | | |

END OF FILE

What is claimed is:

1. An apparatus for automatically classifying red blood cells in a blood specimen comprising means for examining a plurality of red blood cells in the blood specimen, means for classifying individual abnormal red blood cells examined by its respective features into one of several abnormal cell subpopulations, and means for reporting the red blood cells in at least one of the respective abnormal cell subpopulations.

2. An apparatus for classifying red blood cells in a blood specimen comprising means for examining a plurality of red blood cells by an analysis of their respective outer peripheral shape and size features, means for optically analyzing the internal regions of the cells for optical density within the internal region of each cell, means for classifying the abnormal red blood cells by their respective features into abnormal cell subpopulations, and means for reporting at least one of said abnormal cell subpopulations.

3. An apparatus for classifying red blood cells comprising means for examining an image having a plurality of red blood cells therein, means for locating each red blood cell in said image, means for examining the peripheral boundary of each cell to extract features concerning the shape thereof, means for examining a center portion of each red blood cell for a substantially different density than said outer portion to provide an inner region feature, and means for classifying abnormal red blood cells into abnormal cell subpopulations based on each cell's respective features.

4. An apparatus for classifying red blood cells comprising means for examining a plurality of red blood cells for identifying features including a central pallor or a lack thereof, and means for classifying into one of several different and mutually exclusive subpopulations those red cells having a central pallor and those red cells lacking a central pallor.

5. An apparatus for classifying red blood cells in a blood specimen comprising means for examining a plurality of red blood cells in the blood specimen, means for classifying abnormal red blood cells by features into subpopulations, and means for determining and reporting a hemoglobin parameter for at least one of said abnormal red blood cell subpopulations.

6. An apparatus for classifying red blood cells by image analysis comprising means for generating a microscopic image of a monolayer of red blood cells on a blood cell slide, means for converting said image by digitization into a quantized image and storing the latter, means for classifying abnormal red blood cells in said quantized image into subpopulations by examining their respective features, and means for reporting a hemoglobin parameter for at least one predetermined subpopulation of abnormal red blood cells.

7. An apparatus for classifying red blood cells on a slide by image analysis without staining of the red blood cells comprising means for fixing the central pallor of the blood cells on the slide without staining the red blood cells, means for examining the red blood cells optically at a light at which the white blood cells and other artifacts are transparent, means for digitizing an optical image of the red blood cells to form quantized images, means for locating the red blood cells in the quantized image, means for determining the size and shape features of the red blood cells, means for examining each cell for a central pallor feature or the lack thereof feature, means for measuring an optical density feature representative of a cell's hemoglobin content, means for classifying said red blood cells into subpopulations in accordance with said features, and means for reporting a hemoglobin parameter for at least one predetermined subpopulation of red blood cells in the blood specimen.

8. An apparatus for classifying red blood cells comprising, means for generating a microscopic red blood cell image containing a plurality of red blood cells therein, means for converting said image by digitization into a quantized image and storing the quantized image in a digital computer, means for scanning the quantized image to find critical thresholds for picture elements of the quantized image indicating individual red blood cells in the original image, means for labeling each picture element connected to an initially located threshold picture element as a portion of and as defining a contiguous outer region for each cell, means for summing levels of the optical densities of the picture elements within each region to define a measure corresponding to the hemoglobin content for each red blood cell, means for examining each of the red blood cells of the digitized image to locate a central pallor boundary or the absence thereof, means for classifying the red blood cells into subpopulations having central pallor and no central pallors and in accordance with their sizes and shapes, and means for reporting parameters for said subpopulations including a hemoglobin characteristic for at least one subpopulation of said red blood cells.

9. An apparatus for classifying red blood cells in a blood specimen comprising means for examining a plurality of red blood cells in the blood specimen, means for classifying individual abnormal red blood cells examined by their respective features into one of several abnormal cell subpopulations, and means for reporting for each abnormal cell subpopulation the following parameters: a quantification in percent of the total population, the mean cell size, the mean cell hemoglobin, and the mean cell hemoglobin density.

10. An apparatus for classifying red blood cells in a blood specimen comprising means for examining a plurality of red blood cells in the blood specimen, means for classifying each individual red blood cell examined by its respective features and for classifying abnormal red blood cells into one of several cell subpopulations, and means for reporting only those subpopulations of abnormal red cells actually found in and classified from the specimen.

11. An apparatus for automatically classifying red blood cells in a blood specimen comprising means for examining a plurality of red blood cells in the blood specimen, means for differentiating and classifying each individual red blood cell examined by its respective features as either a normal erythrocyte or as an abnormal erythrocyte, and means for reporting the presence or absence of at least the abnormal erythrocytes.

12. An apparatus for classifying red blood cells in a blood specimen comprising means for examining a plurality of red blood cells in the blood specimen, means for classifying each individual red blood cell examined by its respective features into cell subpopulations by differentiating the round blood cells from the non-round blood cells, means for further differentiating the round cells by analysis of their individual internal cell regions into subpopulations, and means for further differentiating the non-round cells into subpopulations.

13. An apparatus for classifying red blood cells comprising means for examining a plurality of red blood cells for identifying features including their respective internal cell morphologies and their individual hemoglobin content, and means for classifying the abnormal red blood cells into subpopulations of abnormal cells based on their respective internal cell morphologies and hemoglobin contents.

14. An apparatus for classifying abnormal red blood cells in a blood specimen comprising means for examining a plurality of red blood cells in the blood specimen, means for classifying each of the red blood cells examined by analysis of their individual cell hemoglobin content, and means for separately classifying into subpopulations of spherocyte cells and microcyte cells by analyses of said internal cell regions and hemoglobin contents.

15. An apparatus for classifying abnormal red blood cells in a blood specimen comprising means for examining a plurality of red blood cells in the blood specimen, means for classifying each of the red blood cells examined by their respective size, internal cell regions, and optical densities, and means for separately classifying target cells from macrocytes, normocytes, and other round cells by analysis of the internal central regions of said cells.

16. An apparatus for classifying red blood cells comprising means for examining the red blood cells to determine their outer peripheral boundary, means for generating a chain code representative of the peripheral boundary for each cell, means for analyzing the chain code to determine parameters of size, roundness, spicularity, and perimeter length for each cell, means for differentiating round cells from non-round cells on the basis of said parameters, and means for classifying some of red blood cells as abnormal red blood cells.

17. An apparatus for classifying red blood cells in a blood specimen comprising means for examining a plurality of red blood cells in the blood specimen, means for generating for each of the red blood cells examined a chain code, means for dividing the red cells into round and non-round categories based on an analysis of their respective chain codes, and means for classifying the non-round category cells into subpopulations based on an analysis of their spiculed, elongated, and size features obtained from their respective chain codes and for reporting out subpopulations of abnormal red cells.

18. An apparatus for classifying red blood cells in a blood specimen comprising the steps of: means for examining a plurality of red blood cells in the blood specimen, means for examining each cell for first, second and third hematologically linguistic descriptors each having predetermined hematological liguistically descriptive modifiers, means for classifying abnormal red blood cells into subpopulations having mutually exclusive descriptors and mutually exclusive descriptive modifiers, and means reporting each subpopulation of red blood cells classified by its hematologically descriptive modifiers and descriptor.

* * * * *

UNITED STATES PATENT AND TRADEMARK OFFICE
CERTIFICATE OF CORRECTION

PATENT NO. : 4,097,845            Page 1 of 4

DATED : June 27, 1978

INVENTOR(S) : JAMES W. BACUS

It is certified that error appears in the above—identified patent and that said Letters Patent are hereby corrected as shown below:

Col. 5, line 14 "coverts" should be --converts--

Col. 7, line 5 "means" should be --mean--

Col. 7, line 7 "means" should be --mean--

Col. 7, Table I, Last column heading has no closing parenthesis.

Col. 9, line 10 "evaluaitons" should be --evaluations--

Col. 10, line 22 "fo" should be --of--

Col. 10, line 28 after "representing" insert --a--

Col. 10, line 38 "digitize" should be --digitized--

Col. 10, line 60 "thereiwth" should be --therewith--

Col. 11, line 14, "sene" should be --scene--

Col. 11, line 21 "intergrated" should be --integrated--

UNITED STATES PATENT AND TRADEMARK OFFICE
CERTIFICATE OF CORRECTION

PATENT NO. : 4,097,845

DATED : June 27, 1978

INVENTOR(S) : JAMES W. BACUS

It is certified that error appears in the above–identified patent and that said Letters Patent are hereby corrected as shown below:

Col. 7, line 58 "euipment" should be --equipment--

Col. 8, line 43 "acurately" should be --accurately--

Col. 9, line 11 "requre" should be --require--

Col. 11, lines 40-41 "and it is labeled initial threshold pixel 48Y for the cell 49C" should be deleted"

Col. 13, Table 2 "4" should be added in the first vertical column

Col. 13, Table 3 "4" should be added to the horizontal heading.

Col. 13, Lines 54-57 "$\rightarrow$" should be --$\Rightarrow$--

Col. 14, line 66 Under "Description" column "$\Sigma$ grey" should be --$\Sigma$ grey levels/area--

"A measure of cell hemoglobin" should be under "How Determined" column with addition of --density (CHD), i.e. F5/F1--

UNITED STATES PATENT AND TRADEMARK OFFICE
CERTIFICATE OF CORRECTION

PATENT NO. : 4,097,845
DATED : June 27, 1978
INVENTOR(S) : JAMES W. BACUS

It is certified that error appears in the above-identified patent and that said Letters Patent are hereby corrected as shown below:

Col. 15, lines 1-4 "(levels area density (CHD), i.e. F5/F1 should be:

| Feature | Description | How Determined |
|---|---|---|
| F8 | Pallor (target flag) | Set if search to center of cell crosses inner threshold |
| F9 | Pallor (grey level) | Edge of cell grey level minus center of cell grey level |
| F10 | $\sum$ grey levels/area | A measure of cell hemoglobin Density (CHD), i.e. F5/F1 |

Col. 18, line 56 "if" should be --It--

Col. 18, line 18 "homoglobin" should be --hemoglobin--

Col. 19, Table 6 - first column heading "thre-" should be --threshold--

UNITED STATES PATENT AND TRADEMARK OFFICE
CERTIFICATE OF CORRECTION

PATENT NO. : 4,097,845

DATED : June 27, 1978

INVENTOR(S) : JAMES W. BACUS

It is certified that error appears in the above-identified patent and that said Letters Patent are hereby corrected as shown below:

In the second vertical column "$20_{pg}$" should be --20 pg-- and "$83_{pg/u}2$" should be --83 pg2--

$\overline{u^2}$

Col. 21, Example III  (1) "Example III" should be moved down.
(2) Title should be to left as in Examples I and II.

Col. 22, Example IV  Third description should be --Hypochromic Normocytes, with Central Pallor--

In the first vertical column 1, --1-- should be added.

Col. 89, line 36 after "having" delete the word --a--

Signed and Sealed this

Twenty-sixth Day of February 1980

[SEAL]

Attest:

Attesting Officer

SIDNEY A. DIAMOND

Commissioner of Patents and Trademarks